US006878715B1

(12) United States Patent
Klein et al.

(10) Patent No.: US 6,878,715 B1
(45) Date of Patent: *Apr. 12, 2005

(54) THERAPEUTIC COMPOUNDS FOR INHIBITING INTERLEUKIN-12 SIGNALS AND METHOD FOR USING SAME

(75) Inventors: J. Peter Klein, Vashon, WA (US); Stephen J. Klaus, New York, NY (US); Anil M. Kumar, Puyallup, WA (US); Baoqing Gong, Shoreline, WA (US)

(73) Assignee: Cell Therapeutics, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/544,984

(22) Filed: Apr. 7, 2000

Related U.S. Application Data

(63) Continuation-in-part of application No. 09/288,556, filed on Apr. 9, 1999, now Pat. No. 6,774,130, which is a continuation-in-part of application No. 09/008,020, filed on Jan. 16, 1998, now Pat. No. 6,469,017, and a continuation-in-part of application No. 08/486,264, filed on Jun. 7, 1995, now Pat. No. 6,103,730, and a continuation-in-part of application No. 08/483,871, filed on Jun. 7, 1995, now Pat. No. 6,100,271, which is a continuation-in-part of application No. 08/217,051, filed on Mar. 24, 1994, now abandoned, which is a continuation-in-part of application No. 08/199,368, filed on Feb. 18, 1994, now abandoned.

(51) Int. Cl.$^7$ ............................................. A61K 31/522
(52) U.S. Cl. ............................ 514/263.34; 514/263.35; 514/263.36
(58) Field of Search .................. 514/263.34, 263.35, 514/363.36, 266

(56) References Cited

U.S. PATENT DOCUMENTS 4,515,795 A   5/1985   Hinze et al.

(Continued)

FOREIGN PATENT DOCUMENTS

EP   0 389 282 A2   9/1990

(Continued)

OTHER PUBLICATIONS

"Development of T$_h$1 CD4$^+$ T Cells Through IL–12 Pro (Continued)

Primary Examiner—Shengjun Wang
(74) Attorney, Agent, or Firm—Nixon & Vanderhye P.C.

(57) ABSTRACT

Novel heterocyclic compounds having a six membered ring structure fused to a five membered ring structure are found to be useful for the treatment and prevention of symptoms or manifestations associated with disorders affected by Interleukin-12 ("IL-12") intracellular signaling, such as, for example, Th1 cell-mediated disorders. The therapeutic compounds, pharmaceutically acceptable derivatives (e.g., resolved enantiomers, diastereomers, tautomers, salts and solvates thereof) or prodrugs thereof, have the following general formula:

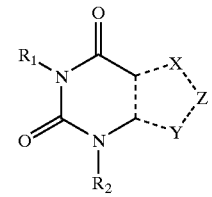

Each X, Y and Z are independently selected from a member of the group consisting of $C(R_3)$, N, $N(R_3)$ and S. Each $R_1$, $R_2$ and $R_3$ is substituted or unsubstituted and is independently selected from a member of the group consisting of hydrogen, halo, oxo, $C_{(1-20)}$alkyl, $C_{(1-20)}$hydroxyalkyl, $C_{(1-20)}$thioalkyl, $C_{(1-20)}$alkylamino, $C_{(1-20)}$alkylaminoalkyl, $C_{(1-20)}$aminoalkyl, $C_{(1-20)}$aminoalkoxyalkenyl, $C_{(1-20)}$aminoalkoxyalkynyl, $C_{(1-20)}$diaminoalkyl, $C_{(1-20)}$triaminoalkyl, $C_{(1-20)}$tetraaminoalkyl, $C_{(5-15)}$aminotrialkoxyamino, $C_{(1-20)}$alkylamido, $C_{(1-20)}$alkylamidoalkyl, $C_{(1-20)}$amidoalkyl, $C_{(1-20)}$acetamidoalkyl, $C_{(1-20)}$alkenyl, $C_{(1-20)}$alkynyl, $C_{(3-8)}$alkoxyl, $C_{(1-11)}$alkoxyalkyl, and $C_{(1-20)}$dialkoxyalkyl.

6 Claims, 3 Drawing Sheets

U.S. PATENT DOCUMENTS

| | | | | |
|---|---|---|---|---|
| 5,039,666 A | * | 8/1991 | Novick, Jr. | |
| 5,629,423 A | | 5/1997 | Klein et al. | |
| 5,648,357 A | | 7/1997 | Bianco et al. | |
| 5,734,051 A | | 3/1998 | Spicer et al. | |
| 5,801,182 A | | 9/1998 | Klein et al. | 514/269 |
| 5,807,861 A | * | 9/1998 | Klein et al. | |
| 6,103,730 A | * | 8/2000 | Klein et al. | |
| 6,133,274 A | * | 10/2000 | Underiner et al. | |

FOREIGN PATENT DOCUMENTS

| | | |
|---|---|---|
| WO | WO94/22449 | 10/1994 |
| WO | WO94/22863 | 10/1994 |
| WO | WO94/24133 | 10/1994 |
| WO | WO95/20589 | 8/1995 |
| WO | WO95/22546 | 8/1995 |

OTHER PUBLICATIONS duced by *Listeria*–Induced Macrophages", by Hsieh et al., Science, vol. 260, Apr. 23, 1993, pp. 547–549.

"Natural Killer Cell Stimulatory Factor (Interleukin 12 [IL–12]) Induces T Helper Type 1 (Th1)– specific Immune Responses and Inhibits the Development of IL–4–producing Th Cells", by Manetti et al., Journal of Exp. Medicine, vol. 177, Apr. 1993, pp. 1199–1204.

"Identification and Purification of Natural Killer Cell Stimulatory Factor (NKSF), A Cytokine with Multiple Biologic Effect on Human Lymphocytes", by Kobayashi et al., Journal of Exp. Medicine, vol. 170, Sep. 1989, pp. 827–846.

"Interleukin 12: A Key Modulator of Immune Function", by Wolf et al., Stem Cells, vol. 12, 1994, pp. 154–168.

"Internleukin–12: A Proinflammatory Cytokine with Immunoregulatory Functions that Bridge Innate Resistance and Antigen–Specific Adaptive Immunity", by Trinchieri, Annu. Rev. Immunol., vol. 13, 1995, pp. 251–276.

"The Role of Cytokines on Various Animal Models of Inflammation", by Heremans et al., Lymphokine Research, vol. 8, No. 3, 1989, pp. 329–333.

"Inducible Cell Contact Signals Regulate Early Activation Gene Expression During B–T Lymphocyte Collaboration", by Klaus et al., The Journal of Immunology, vol. 49, No. 6, Sep. 1992, pp. 1867–1875.

"Generation of Interleukin 4 (IL–4)–producing Cells In Vivo and In Vitro: IL–2 and IL–4 Required for In Vitro Generation of IL–4–producing Cells", by Le Gros, et al., The Journal of Experimental Medicine, vol. 172, Sep. 1990, pp. 921–929.

"Inhibition of Human Interleukin–12 Production by Pentoxifylline", by Moller et al., Immunology, vol. 91, 1997, pp. 197–203.

"The Immunology of Mutliple Sclerosis and its Animal Model, Experimental Allergic Encephalomyelitis", by Owens et al., Neurologic Clinics, vol. 13, No. 1, Feb. 1995.

"Interleukin 12", R& D Systems Catalog, pp. 67–69, 1995.

"Long–term Treatment of Chronic Relapsing Experimental Allergic Encephalomyelitis by Transforming Growth Factor–β2", by Racke et al., Journal of Neuroimmunology, vol. 46, 1993, pp. 175–184.

"Phosphodiesterase Inhibitor Pentoxifylline, a Selective Suppressor of T Helper Type 1– but not Type 2–associated Lymphokine Production, Prevents Induction of Experimental Autoimmune Encephalomyelitis in Lewis Rats", by Rott et al., Eur. J. Immumol., vol. 23, 1993, pp. 1745–1751.

"The Role of IL–12 in the Induction of Organ–Specific Autoimmune Diseases", by Trembleau et al., Immunology Today, vol. 16, No. 8, 1995, pp. 383–386.

Remington Pharmaceutical Sciences, Chapters 83–92, 1990, pp. 1519–1751.

* cited by examiner

THERAPEUTIC COMPOUNDS FOR INHIBITING INTERLEUKIN-12 SIGNALS AND METHOD FOR USING SAME

CROSS REFERENCE TO RELATED APPLICATIONS

This patent application is a (1) continuation-in-part of U.S. application Ser. No. 09/288,556, which was filed Apr. 9, 1999, now U.S. Pat. No. 6,774,130 which in turn is a continuation-in-part of U.S. application Ser. No. 09/008,020, which was filed Jan. 16, 1998, now U.S. Pat. No. 6,469,017; (2) continuation-in-part of allowed U.S. application Ser. No. 08/486,264, which was filed Jun. 7, 1995, now U.S. Pat. No. 6,103,730, which in turn is a continuation-in-part of abandoned U.S. application Ser. No. 08/217,051, which was filed Mar. 24, 1994 now abandoned; and (3) continuation-in-part of allowed U.S. application Ser. No. 08/483,871, which was filed Jun. 7, 1995, now U.S. Pat. No. 6,100,271, which in turn is a continuation-in-part of abandoned U.S. application Ser. No. 08/199,368, which was filed Feb. 18, 1994, now abandoned. The entire disclosures of the above-identified patent applications are incorporated herein by reference and the benefit of each is hereby claimed.

A portion of this invention was made with U.S. government support under grant number R42 NS 35762-03 from the National Institutes of Health (NIGMS). The government may have certain rights in this invention.

FIELD OF THE INVENTION

The present invention generally relates to novel therapeutic compounds, pharmaceutical compositions containing such compounds, methods for preparing such compounds and methods for using these compounds, alone or in combination with other therapeutic agents, for the treatment and prevention of symptoms or manifestations (e.g., inflammation) associated with disorders affected by Interleukin-12 ("IL-12") intracellular signaling, such as, for example, Th1 cell-mediated disorders.

BACKGROUND OF THE INVENTION

Inflammatory responses are a component of the pathogenesis of many vertebrate disorders/diseases, including those in humans. In its broadest meaning, the term "inflammation" denotes local as well as systemic responses. Increased blood flow, vasodilation, fluid transudation from the vessels, infiltration of the tissues by leukocytes and, in some severe cases, intravascular thrombosis, damage to the blood vessels and extravasation of blood characterize local inflammation. The systemic inflammatory response, also denoted as an acute phase response, is characterized by various reactions including, for example, fever, leukocytosis and release of acute phase reactants into the serum. In severe cases, shock and death may occur. See Heremans et al., *Lymphokine Research* 8(3): 329–333 (1989). Diseases involving inflammation are particularly harmful when they afflict the respiratory system, resulting in obstructed breathing, hypoxemia, hypercapnia and lung tissue damage. Obstructive diseases of the airways are characterized by airflow limitation (i.e., airflow obstruction or narrowing) due to constriction of airway smooth muscle, edema and hypersecretion of mucous leading to increased work in breathing, dyspnea, hypoxemia and hypercapnia. While the mechanical properties of the lungs during obstructed breathing are shared between different types of obstructive airway diseases, the pathophysiology can differ.

The inflammatory response is believed to be controlled by a variety of cellular events characterized by the influx of certain cell types and mediators, the presence of which can lead to tissue damage and sometimes death. For example, cytokines are primary factors in the biochemical cascade of events that regulate inflammatory responses. Some cytokines induce or release other known mediators of inflammation. These systems are controlled by related feedback mechanisms. Thus, it is believed that inflammatory responses are not a result of a single cytokine being released in large quantities, but rather to a set of cytokines collectively acting via a network of intercellular signals to incite the inflammatory response.

One particular cytokine, IL-12, also referred to as natural killer cell stimulatory factor ("NKSF") or cytotoxic lymphocyte maturation factor ("CLMF"), is a potent immunoregulatory molecule that plays a role in a wide range of diseases. In particular, IL-12 is a heterodimeric cytokine that is produced by phagocytic cells, e.g., monocytes/macrophages, B-cells and other antigen-presenting cells ("APC") and is believed to act as a proinflammatory cytokine. IL-12 is believed to play a specific role in diseases exhibiting an inflammatory component, namely, diseases that exhibit cell-mediated inflammatory responses, such as, multiple sclerosis, diabetes, chronic inflammatory bowel disease, etc.

IL-12 affects both natural killer cells ("NK cells") and T-lymphocytes ("T cells"), and stimulates IFN-γ production by both of these cell types. For example, in NK cells, IL-12 stimulates: NK cell proliferation, membrane surface antigen up-regulation, LAK cell generation and NK cell activity elevation; induces IFN-γ and TNF-α production and the growth and expansion of either resting or activated NK cells; and increases soluble p55 and soluble p75 TNF receptor production and NK cell cytotoxicity. See *R&D Systems Catalog*, pp. 67–69 (1995). T cells recognize antigens via interaction of a heterodimeric (alpha/beta, or gamma/delta) receptor with short peptide antigenic determinants that are associated with major histocompatibility complex ("MHC") molecules. T cells can be divided broadly into two functional categories by the presence of two mutually exclusive antigens on their cell surface, CD4 (helper) and CD8 (cytotoxic). The CD4 and CD8 antigens regulate T cell interaction with MHC and their mutually exclusive expression derives from their strict specificity for MHC. Class II MHC-restricted T cells are primarily CD4+ and class I MHC-restricted T cells are CD8+. The T cells further differentiate into helper, cytotoxic and suppressor cells.

As mentioned above, IL-12 also affects T cells, including stimulation of T cell IFN-γ production in response to antigen. While CD8+ T cells are associated with cytotoxicity functions, CD4+ T cells are associated with helper function and secrete various cytokines that regulate and modulate immune responses. CD4+ T cells can be further subdivided into T helper 1 (Th1) and T helper 2 (Th2) subsets, according to the profile of cytokines they secrete. Therefore, Th1 cells produce predominantly inflammatory cytokines, including IL-2, TNF-α and IFN-γ, while Th2 cells produce anti-inflammatory cytokines such as IL-4, IL-5, IL-10, and IL-13 that are linked to B cell growth and differentiation.

The Th1 and Th2 CD4+ T cell subsets are derived from a common progenitor cell, termed Th0 cells. During an initial encounter with an antigen, the differentiation into Th1 and Th2 is controlled by the opposing actions of two key cytokines, namely IL-12 and IL-4, which induce the differentiation of Th0 into Th1 and Th2, respectively. The development of Th1 and Th2 cells is primarily influenced by the cytokine milieu during the initial phase of the immune response, in which IL-12 and IL-4, respectively, play decisive roles. The cytokines produced by each Th-cell phenotype are inhibitory for the opposing phenotype. For example, Th1 cytokines enhance cell-mediated immunities and inhibit humoral immunity. Th2 cytokines enhance humoral immunity and inhibit cell-mediated immunities. Trembleau et al., See *Immunology Today* 16(8): 383–386 (1995).

Furthermore, CD4+ Th1 cells play a role in the pathogenesis of immunological disorders. These cells primarily secrete cytokines associated with inflammation such as IFN-γ, TNF-α, TNF-β and IL-2. IFN-γ is an important component of the inflammatory response and resultant pathology of those diseases exhibiting an inflammatory response. Heremans, et al. In addition to its role in inflammatory response, IFN-γ also contributes to phagocytic cell activation (i.e., macrophage activation), and up-regulation of MHC expression on the surface of antigen-presenting cells ("APC") and other cells. Further, this cytokine is implicated generally in inflammatory immune responses, and in autoimmune diseases, such as multiple sclerosis ("MS"), specifically. See Owens et al., *Neurologic Clinics*, 13(1):51–73 (1995). Furthermore, steroid treatment broadly attenuates cytokine production, but it cannot modulate it selectively, e.g., just the Th0, the Th1 or the Th2 pathways.

IL-12 plays a role in the induction of Th1 cell-mediated autoimmunity. Recent evidence points to a critical role for IL-12 in the pathogenesis of rodent models of Th1-mediated autoimmune diseases such as type-1 diabetes, multiple sclerosis, rheumatoid arthritis, inflammatory bowel disease, and acute graft-versus-host disease. Thus, Th1 cells are believed to be involved in the induction of experimental autoimmune diseases, as demonstrated in adoptive transfer experiments demonstrating the CD4+ cells producing Th1-type lymphokines can transfer disease, as shown in models of experimental autoimmune disease, such as experimental allergic encephalomyelitis ("EAE") (also known as experimental allergic encephalitis) and insulin-dependent diabetes mellitus ("IDDM"). See Trinichieri, *Annu. Rev. Immunol.* 13(1):251–276 (1995). For instance, EAE is an inflammatory T cell mediated, paralytic, demyelinating, autoimmune disease that can be induced in a number of rodents as well as primates. Owens et al. One of the ways that EAE can be induced is by immunization of animals with myelin basic protein ("MBP"). Likewise, administration of IL-12 induces rapid onset of IDDM in 100% of NOD female mice. Trinichieri. Thus, one goal of immunotherapy research and development efforts has been to limit inflammatory response while leaving the specificity of the immune system, deemed necessary for host protection, in tact.

For example, steroid therapy is the most common treatment for one such IL-12 mediated disease, MS, particularly, corticosteroids. This suggests that steroids after the trafficking of cells into the brain or reduce the secretion of cytokines by inflammatory cells in areas of inflammation. Although their effect in reversing some of the acute symptoms of autoimmune disease, such as MS, are well known, their side effects have precluded long-term use.

Other treatments that target immune system components include lymphocyte cytotoxic drugs such as cyclophosphamide and azathioprine. These drugs act like "sledgehammers" in that they suppress the entire immune system and raise problems that attend broad-spectrum immunosuppression therapies. The same problems also are likely with newer therapies such as cyclosporine, anti-CD4 monoclonal antibodies, and others. Other treatments for IL-12 mediated diseases, including MS, can involve the administration of anti-IL-12 antagonists such as antibodies. Anti-IL-12 antibodies have been shown to inhibit the development of IDDM and EAE. See Trinichieri. However, antibody based immunotherapy may result in immune complex formation and deposition, thus leading to glomerulonephritis, vasculitis and arthritis.

Moreover, symptomatic treatment with beta-agonists, anticholinergic agents and methyl xanthines have been clinically beneficial for the relief of discomfort but fail to stop the underlying inflammatory processes that cause the disease. The frequently used systemic glucocorticosteroids have numerous side effects, including, but not limited to, weight gain, diabetes, hypertension, osteoporosis, cataracts, atherosclerosis, increased susceptibility to infection, increased lipids and cholesterol, and easy bruising. Aerosolized glucocorticosteroids have fewer side effects but can be less potent and have side effects, such as thrush.

The use of anti-inflammatory and symptomatic relief reagents is a serious problem because of their side effects or their failure to attack the underlying cause of an inflammatory response. Other anti-inflammatory agents, such as cromolyn and nedocromil are much less potent and have fewer side effects. Anti-inflammatory agents that are primarily used as immunosuppressive agents and anti-cancer agents (i.e., cytoxan, methotrexate and Immuran) have also been used to treat inflammation. These agents, however, have serious side effect potential, including, but not limited to, increased susceptibility to infection, liver toxicity, drug-induced lung disease, and bone marrow suppression. Thus, such drugs have found limited clinical use, for example, in the treatment of most airway hyperresponsiveness lung diseases.

Accordingly, there remains a need for novel therapeutic compounds and methods that inhibit the deleterious effects of inflammatory responses mediated by specific cytokines, such as IL-12, without adversely affecting the other components of the immune system that are deemed necessary for protecting the host and without the attendant disadvantages of conventionally available compounds and methods.

SUMMARY OF THE INVENTION

It is an object of the present invention to provide novel therapeutic compounds, including pharmaceutical compositions thereof and methods useful for inhibiting IL-12 signaling in a mammal having, for example, an inflammatory response.

It is another object of the present invention to provide novel therapeutic compounds, pharmaceutical compositions thereof and methods that are capable of limiting the inflammatory response of a subject without adversely affecting the specificity of the immune system deemed necessary for protecting the subject.

The above and other objects are accomplished by a compound, pharmaceutically acceptable derivatives (e.g., racemic mixtures, resolved enantiomers, diastereomers, tautomers, salts and solvates thereof) or prodrugs thereof, having the following Formula I:

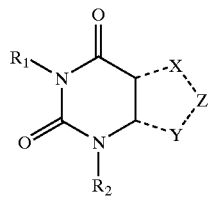

wherein:
the dashed lines, i.e., "‒ ‒ ‒", in Formula I represent either a single or double bond;

X, Y and Z are independently selected from a member of the group consisting of $C(R_3)$, N, $N(R_3)$ and S;

$R_1$ is selected from a member of the group consisting of hydrogen, methyl, substituted alkyl (as defined herein, which includes without limitation substituted $C_{(5-9)}$ alkyl), $C_{(5-9)}$alkenyl, $C_{(5-9)}$alkynyl, $C_{(5-9)}$hydroxyalkyl, $C_{(3-8)}$alkoxyl, $C_{(5-9)}$alkoxyalkyl; and $R_2$ and $R_3$ are independently selected from a member of the group consisting of hydrogen, halo, oxo (keto), $C_{(1-20)}$alkyl, $C_{(1-20)}$hydroxyalkyl, $C_{(1-20)}$thioalkyl, $C_{(1-20)}$alkylamino, $C_{(1-20)}$alkylaminoalkyl, $C_{(1-20)}$ aminoalkyl, $C_{(1-20)}$aminoalkoxyalkenyl, $C_{(1-20)}$ aminoalkoxyalkynyl, $C_{(1-20)}$diaminoalkyl, $C_{(1-20)}$ triaminoalkyl, $C_{(1-20)}$tetraaminoalkyl, $C_{(5-15)}$ aminotrialkoxyamino, $C_{(1-20)}$alkylamido, $C_{(1-20)}$ alkylamidoalkyl, $C_{(1-20)}$amidoalkyl, $C_{(1-20)}$ acetamidoalkyl, $C_{(1-20)}$alkenyl, $C_{(1-20)}$alkynyl, $C_{(3-8)}$ alkoxyl, $C_{(1-11)}$alkoxyalkyl, and $C_{(1-20)}$dialkoxyalkyl.

$R_1$ is optionally substituted with a member of the group consisting of N—OH, acylamino, cyano (e.g., NC—), cyanamido (e.g., (NCNH—), cyanato (e.g., (NCO—), sulfo, sulfonyl, sulfinyl, sulfhydryl (mercapto), sulfeno, sulfanilyl, sulfamyl, sulfamino, and phosphino, phosphinyl, phospho, phosphono and —$NR^aR^b$, wherein each of $R^a$ and $R^b$ may be the same or different and each is independently selected from the group consisting of hydrogen, optionally substituted alkyl, cycloalkyl, alkenyl, cycloalkenyl, alkynyl, aryl, heteroaryl and heterocyclic group.

Each $R_2$ and $R_3$ is optionally substituted with one or more members of the group consisting of hydroxyl, methyl, carboxyl, furyl, furfuryl, biotinyl, phenyl, naphthyl, amino group (e.g., —$NH_2$), amido group (e.g., —C(=O)N—), carbamoyl group (e.g., $H_2NCO$—), cyano (e.g., NC—), cyanamido (e.g., NCNH—), cyanato (e.g., NCO—), sulfo, sulfonyl, sulfinyl, sulfhydryl (mercapto), sulfeno, sulfanilyl, sulfamyl, sulfamino, phosphino, phosphinyl, phospho, phosphono, N—OH, —$Si(CH_3)_3$, $C_{(1-3)}$alkyl, $C_{(1-3)}$ hydroxyalkyl, $C_{(1-3)}$thioalkyl, $C_{(1-3)}$alkylamino, benzyldihydrocinnamoyl group, benzoyldihydrocinnamido group, heterocyclic group and carbocyclic group.

The heterocyclic group or carbocyclic group is optionally substituted with one or more members of the group consisting of halo, hydroxyl, nitro (e.g., —$NO_2$), $SO_2NH_2$, $C_{(1-6)}$ alkyl, $C_{(1-6)}$haloalkyl, $C_{(1-8)}$alkoxyl, $C_{(1-11)}$alkoxyalkyl, $C_{(1-6)}$alkylamino, and $C_{(1-6)}$aminoalkyl.

Preferably, both X and Y are not $N(R_3)$ when Z is $C(R_3)$ and $R_3$ is H or $C_{(1-3)}$alkyl.

More preferably, $R_1$ is not an ω-1 secondary alcohol substituted $C_{(5-8)}$alkyl when both X and Y are $N(R_3)$, Z is $C(R_3)$ and $R_3$ is H or $C_{(1-3)}$alkyl.

In a further aspect, the present invention is directed to a method for inhibiting a cellular process or activity mediated by IL-12, the method comprising:

(a) contacting IL-12 responsive cells with a compound of the present invention, as described herein; and
(b) determining that the cellular process or activity mediated by IL-12 is inhibited.

In a still further aspect, the present invention is directed to a method for treating a Th1 cell-mediated inflammatory response in a mammal in need of such treatment, the method comprising:

administering to the mammal a therapeutically effective amount of the compound of the present invention, wherein said compound is capable of inhibiting an IL-12 mediated cellular process or activity, thereby inhibiting the inflammatory response.

In accomplishing the above and other objects, the present invention provides novel therapeutic compounds and methods for affecting, inter alia, the inflammatory response associated with Th1 cell-mediated diseases, without affecting the other components of the immune system that are deemed necessary for host protection. The compounds and methods of the present invention are characterized by their ability to inhibit IL-12 signaling. Without wishing to be bound by theory, it is believed that the therapeutic compounds of the present invention short-circuit the inflammatory cascade by inhibiting IL-12 dependent Th1 development, emphasizing the present invention's importance in disease therapy by inhibiting IL-12 signaling in the regulation of Th1-mediated inflammatory disorders. Inhibition of IL-12 signaling decreases the production of IFN-γ, thus mitigating the inflammatory response in disease conditions mediated by Th1 cells. Specifically, the present invention may impede signaling that induces differentiation of T cells to Th1 cells. In general, differentiated Th1 cells produce high levels of IFN-γ, which provokes inflammation, a component of many disease conditions that the inventive compounds and methods target.

The present invention achieves the above and other objects by, inter alia, providing novel therapeutic compounds and methods for treating or preventing IL-12 or Th1 mediated symptoms (e.g. inflammation) of diseases that include, without limitation, (1) inflammatory diseases or disorders, such as, for example, arthritis, asthma, chronic inflammatory diseases, chronic intestinal inflammation, psoriasis, septic shock, septicemia, and adult respiratory distress syndrome; (2) autoimmune diseases or disorders, such as, for example, acute and chronic graft-versus-host disease, autoimmune gastritis, autoimmune hemolytic anemia, autoimmune neutropenia, chronic active hepatitis, chronic thyroiditis, inflammatory bowel disease (e.g., Crohn's Disease and ulcerative colitis), lupus disorders (e.g., systemic lupus erythematosus), multiple sclerosis, myasthenia gravis, rheumatoid arthritis, scleroderma, thrombocytopenia, thyroid diseases (e.g., Graves' and Hashimoto's disease), type-1-IDDM, and uveitis; and (3) neurodegenerative diseases such as, for example, amyotrophic lateral sclerosis, Alzheimer's disease, Parkinson's disease, and primary lateral sclerosis. The compounds of the present invention may be employed in any suitable conventional manner for the treatment of the above diseases. Such methods of treatment, their dosage levels and requirements may be selected by those of skill in the art from available methods and techniques that are further described below, that are known in the art or that are readily determinable using routine experimentation.

The compounds of the present invention will also be useful for inhibiting IL-12 mediated signaling in other applications such as in vitro systems and in vivo animal models of IL-12 mediated diseases. Accordingly, the present invention encompasses a kit comprising a compound of the present invention, as described herein, for use in such applications.

Additional aspects, embodiments and advantages of the present invention will be set forth, in part, in the description that follows, or may be learned from practicing or using the present invention. The objects and advantages may be realized and attained by means of the features and combinations particularly pointed out throughout this description and the appended claims. It is to be understood that the foregoing general description and the following detailed description are exemplary and explanatory only and are not to be viewed as being restrictive of the invention as claimed.

BRIEF DESCRIPTION OF THE DRAWING

The accompanying drawing, which is incorporated in and constitutes a part of the specification, illustrates an embodiment of the present invention and, together with the description, serves to exemplify the principles of the present invention.

DETAILED DESCRIPTION OF PREFERRED EMBODIMENTS

Figure 1:
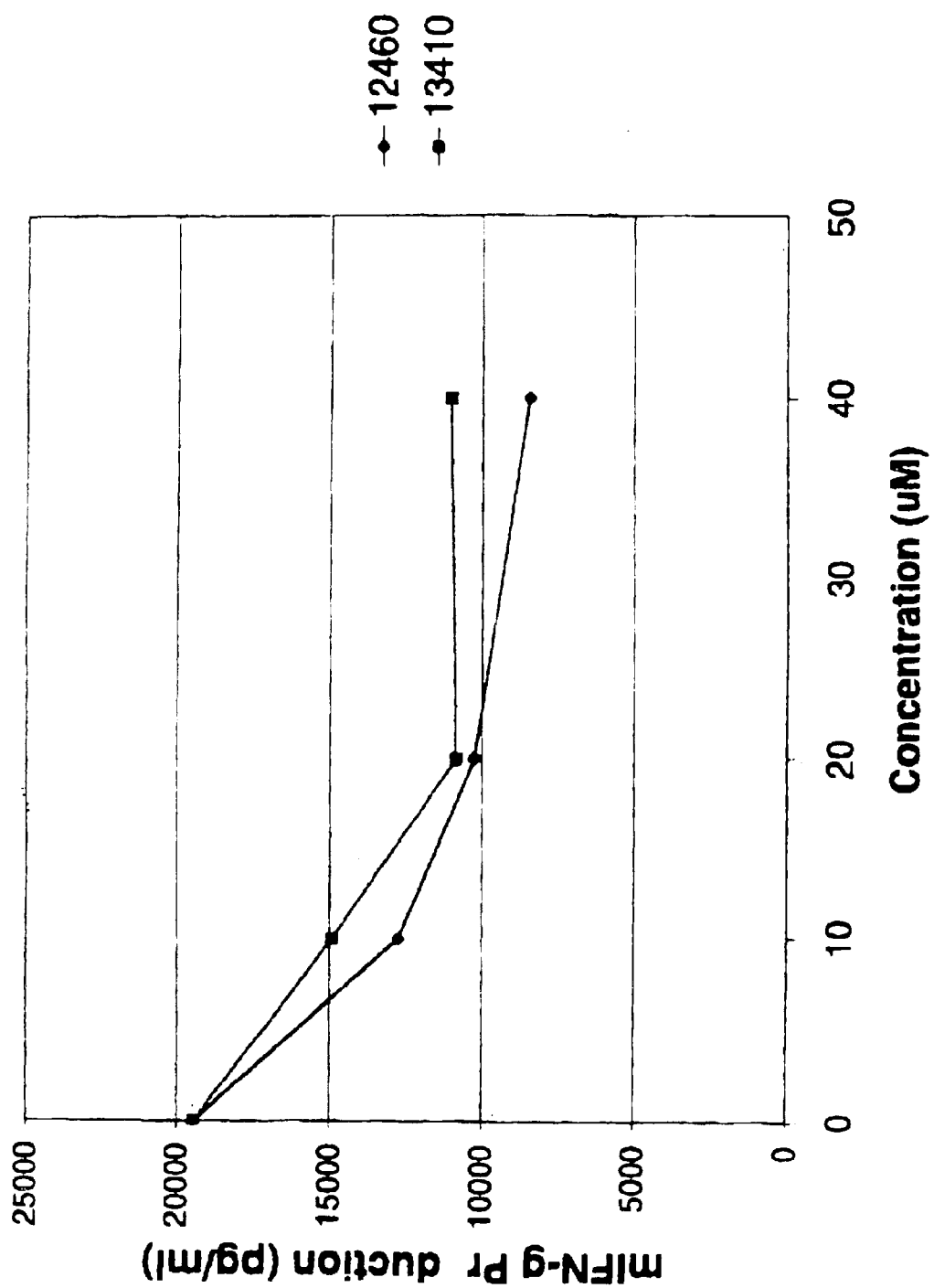
FIG. 1 shows the ability of (R)-3-(6-biotinylamidohexyl)-1-(5-hydroxyhexyl)-7-methylxanthine (CT 12460) and (R)-3-(6-biotinylamidoethyl)-1-(5-hydroxyhexyl)-7-methylxanthine (CT 13410) to interfere with IL-12 signaling in an IL-12 induced IFN-γ secretion assay.

All patents, patent applications and publications cited in this description are incorporated herein by reference in their entirety. In the case of inconsistencies, the present disclosure, including definitions, will prevail.

The present invention relates to a new class of heterocyclic compounds having a six membered ring structure fused to a five membered ring structure. In particular, the present invention provides a compound, pharmaceutically acceptable derivatives (e.g., racemic mixtures, resolved enantiomers, diastereomers, tautomers, salts and solvates thereof) or prodrugs thereof, having the following Formula I:

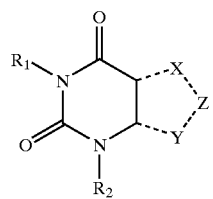

wherein:
the dashed lines, i.e., "———", in Formula I represent a single or double bond;
X, Y and Z are independently selected from a member of the group consisting of $C(R_3)$, N, $N(R_3)$ and S;
$R_1$ is selected from a member of the group consisting of hydrogen, methyl, substituted alkyl (as defined herein, which includes without limitation substituted $C_{(5-9)}$ alkyl), $C_{(5-9)}$alkenyl, $C_{(5-9)}$alkynyl, $C_{(5-9)}$hydroxyalkyl, $C_{(3-8)}$alkoxyl, $C_{(5-9)}$alkoxyalkyl; and
$R_2$ and $R_3$ are independently selected from a member of the group consisting of hydrogen, halo, oxo, $C_{(1-20)}$alkyl, $C_{(1-20)}$hydroxyalkyl, $C_{(1-20)}$thioalkyl, $C_{(1-20)}$alkylamino, $C_{(1-20)}$alkylaminoalkyl, $C_{(1-20)}$aminoalkyl, $C_{(1-20)}$aminoalkoxyalkenyl, $C_{(1-20)}$aminoalkoxyalkynyl, $C_{(1-20)}$diaminoalkyl, $C_{(1-20)}$triaminoalkyl, $C_{(1-20)}$tetraaminoalkyl, $C_{(5-15)}$aminotrialkoxyamino, $C_{(1-20)}$alkylamido, $C_{(1-20)}$alkylamidoalkyl, $C_{(1-20)}$amidoalkyl, $C_{(1-20)}$acetamidoalkyl, $C_{(1-20)}$alkenyl, $C_{(1-20)}$alkynyl, $C_{(3-8)}$alkoxyl, $C_{(1-11)}$alkoxyalkyl, and $C_{(1-20)}$dialkoxyalkyl.

$R_1$ is optionally substituted with a member selected from the group consisting of N—OH, acylamino, cyano (e.g., NC—), cyanamido (e.g., (NCNH—), cyanato (e.g., (NCO—), sulfo, sulfonyl, sulfinyl, sulfhydryl (mercapto), sulfeno, sulfanilyl, sulfamyl, sulfamino, and phosphino, phosphinyl, phospho, phosphono and —$NR^aR^b$, wherein each of $R^a$ and $R^b$ may be the same or different and each is independently selected from the group consisting of hydrogen, optionally substituted alkyl, cycloalkyl, alkenyl, cycloalkenyl, alkynyl, aryl, heteroaryl and heterocyclic group.

Each $R_2$ and $R_3$ is optionally substituted with one or more members of the group consisting of hydroxyl, methyl, carboxyl, furyl, furfuryl, biotinyl, phenyl, naphthyl, amino group, amido group, carbamoyl group, cyano (e.g., NC—), cyanamido (e.g., NCNH—), cyanato (e.g., NCO—), sulfo, sulfonyl, sulfinyl, sulfhydryl (mercapto), sulfeno, sulfanilyl, sulfamyl, sulfamino, phosphino, phosphinyl, phospho, phosphono, N—OH, —Si(CH$_3$)$_3$ (a.k.a. SiMe$_3$), $C_{(1-3)}$alkyl, $C_{(1-3)}$hydroxyalkyl, $C_{(1-3)}$thioalkyl, $C_{(1-3)}$alkylamino, benzyldihydrocinnamoyl group, benzoyldihydrocinnamido group, heterocyclic group and carbocyclic group.

The heterocyclic group or carbocyclic group is optionally substituted with one or more members of the group consisting of halo, hydroxyl, nitro (e.g., —NO$_2$), SO$_2$NH$_2$, $C_{(1-6)}$alkyl, $C_{(1-6)}$haloalkyl, $C_{(1-8)}$alkoxyl, $C_{(1-11)}$alkoxyalkyl, $C_{(1-6)}$alkylamino, and $C_{(1-6)}$aminoalkyl.

Preferably, both X and Y are not $N(R_3)$ when Z is $C(R_3)$ and $R_3$ is H or $C_{(1-3)}$alkyl.

More preferably, $R_1$ is not an ω-1 secondary alcohol substituted $C_{(5-8)}$alkyl when both X and Y are $N(R_3)$, Z is $C(R_3)$ and $R_3$ is H or $C_{(1-3)}$alkyl.

In a another preferred embodiment, the present invention is directed to a therapeutic compound, pharmaceutically acceptable derivatives (e.g., racemic mixtures, resolved enantiomers, diastereomers, tautomers, salts and solvates thereof) or prodrugs thereof, having the following Formula II:

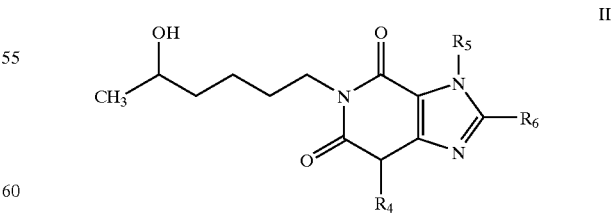

wherein $R_4$, $R_5$ and $R_6$ are independently selected from a member of the group consisting of hydrogen, halo, oxo, $C_{(1-20)}$alkyl, $C_{(1-20)}$hydroxyalkyl, $C_{(1-20)}$thioalkyl, $C_{(1-20)}$alkylamino, $C_{(1-20)}$alkylaminoalkyl, $C_{(1-20)}$aminoalkyl, $C_{(1-20)}$aminoalkoxyalkenyl, $C_{(1-20)}$aminoalkoxyalkynyl, $C_{(1-20)}$diaminoalkyl, $C_{(1-20)}$triaminoalkyl, $C_{(1-20)}$tetraaminoalkyl, $C_{(3-15)}$aminodialkoxyamino, $C_{(5-15)}$aminotrialkoxyamino, $C_{(1-20)}$alkylamido, $C_{(1-20)}$alkylamidoalkyl, $C_{(1-20)}$amidoalkyl, $C_{(1-20)}$acetamidoalkyl, $C_{(1-20)}$alkenyl, $C_{(1-20)}$alkynyl, $C_{(3-8)}$alkoxyl, $C_{(1-11)}$alkoxyalkyl, and $C_{(1-20)}$dialkoxyalkyl.

Each $R_4$, $R_5$ and $R_6$ is optionally substituted with one or more members of the group consisting of hydroxyl, methyl, carboxyl, furyl, furfuryl, biotinyl, phenyl, naphthyl, amino group, amido group, carbamoyl group, cyano (e.g., NC—), cyanamido (e.g., NCNH—), cyanato (e.g., NCO—), sulfo, sulfonyl, sulfinyl, sulfhydryl (mercapto), sulfeno, sulfanilyl, sulfamyl, sulfamino, phosphino, phosphinyl, phospho, phosphono, N—OH, —Si(CH$_3$)$_3$, $C_{(1-3)}$alkyl, $C_{(1-3)}$hydroxyalkyl, $C_{(1-3)}$thioalkyl, $C_{(1-3)}$alkylamino, benzyldihydrocinnamoyl group, benzoyldihydrocinnamido group, heterocyclic group and carbocyclic group.

The heterocyclic group or carbocyclic group is optionally substituted with one or more members of the group consisting of halo, hydroxyl, nitro (e.g., —NO$_2$), SO$_2$NH$_2$, $C_{(1-6)}$alkyl, $C_{(1-6)}$haloalkyl, $C_{(1-8)}$alkoxyl, $C_{(1-11)}$alkoxyalkyl, $C_{(1-6)}$alkylamino, and $C_{(1-6)}$aminoalkyl. In a preferred embodiment, each $R_4$, $R_5$ and $R_6$ are not simultaneously methyl.

In a preferred embodiment, both $R_4$ and $R_5$ are not methyl when $R_6$ is H.

In another preferred embodiment, $R_6$ is not methyl when $R_4$ is methylfuryl and $R_5$ is H.

In a further preferred embodiment, $R_6$ is not propyl or isopropyl when $R_4$ is methyl and $R_5$ is H.

In a still further preferred embodiment, $R_4$ is not acetamidohexyl when $R_5$ is methyl and $R_6$ is H.

Suitable examples of $R_2$, and $R_3$ groups of Formula I and $R_4$, $R_5$ and $R_6$ groups of Formula II include, without limitation, members selected from the group consisting of 1-adamantanemethyl, 1-phenylcyclopropyl, 1-phenylproply, 1-propenyl, 2-bromopropyl, 2-buten-2-yl, 2-butyl, 2-cyclohexylethyl, 2-cyclopentylethyl, 2-furyl, 2-hydroxyethyl, 2-hydroxystyryl, 2-methoxyethyl, 2-methoxysytryl, 2-methylbutyl, 2-methylcyclopropyl, 2-norboranemethyl, 2-phenylpropyl, 2-propenyl, 2-propenyl, 2-propyl, 2-thienyl, 2-trifluoromethylstyryl, 3,4,5-triethoxyphenyl, 3,4,5-trimethoxyphenyl, 3,4-dichlorobenzyl, 3,4-dichlorophenyl, 3,4-difluorophenyl, 3,4-difluorobenzyl, 3,4-dihydroxybenzyl, 3,4-dihydroxystyryl, 3,4-dimethoxybenzyl, 3,4-dimethoxyphenethyl, 3,4-dimethoxyphenyl, 3,4-dimethoxystyryl, 3,4-dimethylphenyl, 3,5-bis(trifluoromethyl)-benzyl, 3,5-dimethylphenyl, 3-bromo-4-methylphenyl, 3-bromobenzyl, 3-cyclohexylpropyl, 3-dimethylaminobutyl, 3-fluoro-4-methylphenyl, 3-fluorobenzyl, 3-hepten-3-yl, 3-hydroxy-n-butyl, 3-hydroxypropyl,3-iodo-4-methylphenyl, 3-methoxy-4-methylphenyl, 3-methoxybenzyl, 3-methylbenzyl, 3-phenylpropyl, 3trifluoromethylbenzyl, 4'-ethyl-4-biphenyl, 4-biphenyl, 4-bromobenzyl, 4-bromophenyl, 4-butylphenyl, 4-chloropentyl, 4-chlorostyryl, 4-ethoxybenzyl, 4-fluorobenzyl, 4-fluorophenyl, 4-hydroxyphenyl, 4-isobutylphenethyl, 4-isopropylphenyl, 4-methoxybenzyl, 4-methoxy-n-butyl, 4-methylbenzyl, 4-methylcyclohexanemethyl, 4-methylcyclohexyl, 4-phenylbenzyl, 4-t-butylcyclohexyl, 4-vinylphenyl, 5-hydroxyhexyl, alpha-methylstyryl, benzyl, cyclobutyl, cycloheptyl, cyclohexyl, cyclohexylmethyl, cyclopentyl, ethyl, hexyl, isobutyl, isopropyl, isovaleryl, m-anisyl, methyl, m-tolyl, n-butyl, n-propyl, p-anisyl, phenethyl, phenyl, propyl, p-tolyl, styryl, t-butyl, and the like.

Preferred $R_2$, $R_3$, $R_4$, and $R_5$ and $R_6$ groups include, without limitation, members selected from the group consisting of methyl, ethyl, oxo, isopropyl, n-propyl, isobutyl, n-butyl, t-butyl, 2-hydroxyethyl, 3-hydroxypropyl, 3-hydroxy-n-butyl, 2methoxyethyl, 4-methoxy-n-butyl, 5-hydroxyhexyl, 2-bromopropyl, 3-dimethylaminobutyl, 4-chloropentyl, methylamino, aminomethyl, methylphenyl, and the like.

In accordance with the principles of the present invention, the novel therapeutic compounds disclosed herein may contain one or more asymmetrically substituted carbon atoms and, thus, may occur as racemates and racemic mixtures, single enantiomers, diastereomeric mixtures and individual diastereomers. Each stereogenic carbon may be of the R or S configuration. Many geometric isomers of olefins, C—N double bonds, and the like can also be present in the compounds described herein, and all such stable isomers are contemplated in the present invention. It is well known in the art how to prepare optically active forms, such as by resolution of racemic forms or by synthesis from optically active starting materials. All chiral, diastereomeric, racemic forms and all geometric forms of a structure are intended to be encompassed within the present invention unless a specific stereochemistry or isomer form is specifically indicated.

The compounds of the present invention may be modified by appending appropriate functionalites to enhance selective biological properties. Such modifications are known in the art and include, without limitation, those which increase penetration into a given biological compartment (e.g., blood, lymphatic system, central nervous system), increase oral or intravenous bioavailability, increase solubility to allow administration by injection, alter metabolism, alter rate of excretion, etc.

DEFINITIONS

"Stable compound", as used herein, is a compound that is sufficiently robust to survive isolation to a useful degree of purity from a reaction mixture, and formulation into an efficacious therapeutic agent, i.e., possesses stability that is sufficient to allow manufacture and that maintains the integrity of the compound for a sufficient period of time to be useful for the purposes detailed herein (e.g., therapeutic or prophylactic administration to a mammal or for use in affinity chromatography applications). Typically, such compounds are stable at a temperature of 40° C. or less, in the absence of moisture or other chemically reactive conditions, for at least a week. "Metabolically stable compound" denotes a compound that remains bioavailable when orally ingested by a mammal.

"Substituted", as used herein, whether express or implied and whether preceded by "optionally" or not, means that any one or more hydrogen on the designated atom (C, N, etc.) is replaced with a selection from the indicated group, provided that the designated atom's normal valency is not exceeded, and that the substitution results in a stable compound. For instance, when a CH$_2$ is substituted by a keto substituent (=O), then 2 hydrogens on the atom are replaced. It should be noted that when a substituent is listed without indicating the atom via which such substituent is bonded, then such substituent may be bonded via any atom in such substituent. For example, when the substituent is piperazinyl, piperidinyl, or tetrazolyl, unless specified otherwise, said piperazinyl, piperidinyl, tetrazolyl group may be bonded to the rest of the compound of Formula I or II, as well as the $R_2$, $R_3$, $R_4$, $R_5$ and $R_6$ groups substituted thereon, via any atom in such piperazinyl, piperidinyl, tetrazolyl group.

Combinations of substituents and/or variables are permissible only if such combinations result in stable compounds. Further, when more than one position in a given structure may be substituted with a substituent selected from a specified group, the substituents may be either the same or different at every position. Typically, when a structure may be optionally substituted, 0–15 substitutions are preferred, 0–5 substitutions are more preferred, and 0–1 substitution is most preferred.

"Optional" or "optionally" means that the subsequently described event or circumstance may or may not occur, and that the description includes, without limitation, instances where said event or circumstance occurs and instances in which it does not. For example, optionally substituted alkyl means that alkyl may or may not be substituted by those groups enumerated in the definition of substituted alkyl.

"Acyl" denotes a radical provided by the residue after removal of hydroxyl from an organic acid. Examples of such acyl radicals include, without limitation, alkanoyl and aroyl radicals. Examples of such lower alkanoyl radicals include, without limitation, formyl, acetyl, propionyl, butyryl, isobutyryl, valeryl, isovaleryl, pivaloyl, hexanoyl, trifluoroacetyl.

"Acylamino" denotes an N-substituted amide, i.e., RC(O)—NH and RC(O)—NR'—. A non-limiting example is acetamido.

"Acyloxy" means 1 to about 4 carbon atoms. Suitable examples include, without limitation, alkanoyloxy, benzoyloxy and the like.

"Alkyl" or "lower alkyl" is intended to include both branched and straight-chain saturated aliphatic hydrocarbon radicals/groups having the specified number of carbon atoms. In particular, "alkyl" refers to a monoradical branched or unbranched saturated hydrocarbon chain, preferably having from 1 to 40 carbon atoms, more preferably 1 to 10 carbon atoms, even more preferably 1 to 6 carbon atoms, such as methyl, ethyl, n-propyl, isopropyl, n-butyl, secondary butyl, tert-butyl, n-hexyl, n-octyl, n-decyl, n-dodecyl, 2-ethyldodecyl, tetradecyl, and the like, unless otherwise indicated.

"Substituted alkyl" refers to an alkyl group as defined above having from 1 to 5 substituents selected, without limitation, from the group consisting of alkoxyl, substituted alkoxyl, cycloalkyl, substituted cycloalkyl, cycloalkenyl, substituted cycloalkenyl, acyl, acylamino, acyloxyl, aminoacyl, aminoacyloxyl, oxyaminoacyl, azido, cyano, halogen, hydroxyl, keto, thioketo, carboxyl, carboxylalkyl, thioaryloxyl, thioheteroaryloxyl, thioheterocyclooxyl, thiol, thioalkoxyl, substituted thioalkoxyl, aryl, aryloxyl, heteroaryl, heteroaryloxyl, heterocyclic, heterocyclooxyl, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic group.

"Alkylamino" denotes amino groups which have been substituted with one or two alkyl radicals. Preferred are "lower N-alkylamino" radicals having alkyl portions having 1 to 6 carbon atoms. Suitable lower alkylamino may be mono or dialkylamino such as N-methylamino, N-ethylamino, N,N-dimethylamino, N,N-diethylamino or the like.

"Alkylaminoalkyl" embraces radicals having one or more alkyl radicals attached to an aminoalkyl radical.

"Alkylaminocarbonyl" denotes an aminocarbonyl group which has been substituted with one or two alkyl radicals on the amino nitrogen atom. Preferred are "N-alkylaminocarbonyl" "N,N-dialkylaminocarbonyl" radicals. More preferred are "lower N-alkylaminocarbonyl" "lower N,N-dialkylaminocarbonyl" radicals with lower alkyl portions as defined above.

"Alkylcarbonyl", "arylcarbonyl" and "aralkylcarbonyl" include radicals having alkyl, aryl and aralkyl radicals, as defined above, attached via an oxygen atom to a carbonyl radical. Examples of such radicals include, without limitation, substituted or unsubstituted methylcarbonyl, ethylcarbonyl, phenylcarbonyl and benzylcarbonyl.

"Alkylsulfinyl" embraces radicals containing a linear or branched alkyl radical, of one to ten carbon atoms, attached to a divalent —S(=O)— radical. More preferred alkylsulfinyl radicals are "lower alkylsulfinyl" radicals having alkyl radicals of one to six carbon atoms. Examples of such lower alkylsulfinyl radicals include, without limitation, methylsulfinyl, ethylsulfinyl, butylsulfinyl and hexylsulfinyl.

"Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include, without limitation, methylsulfonyl, ethylsulonyl and propylsulfonyl. The "alkylsulfonyl" radicals may be further substituted with one or more halo atoms, such as fluoro, chloro or bromo, to provide haloalkylsulfonyl radicals.

"Alkylthio" embraces radicals containing a linear or branched alkyl radical, of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio.

"Alkylthioalkyl" embraces radicals containing an alkylthio radical attached through the divalent sulfur atom to an alkyl radical of one to about ten carbon atoms. More preferred alkylthioalkyl radicals are "lower alkylthioalkyl" radicals having alkyl radicals of one to six carbon atoms. Examples of such lower alkylthioalkyl radicals include, without limitation, methylthiomethyl.

"Alkylene" refers to a diradical of a branched or unbranched saturated hydrocarbon chain, preferably having from 1 to 40 carbon atoms, more preferably 1 to 10 carbon atoms, even more preferably 1 to 6 carbon atoms. This term is exemplified by groups such as methylene (—CH$_2$—), ethylene (—CH$_2$CH$_2$—), the propylene isomers (e.g.—CH$_2$CH$_2$CH$_2$— and —CH(CH$_3$)CH$_2$—), and the like.

"Substituted alkylene" refers to: (1) an alkylene group as defined above having from 1 to 5 substituents selected from a member of the group consisting of alkoxyl, substituted alkoxyl, cycloalkyl, substituted cycloalkyl, cycloalkenyl, substituted cycloalkenyl, acyl, acylamino, acyloxyl, aminoacyl, aminoacyloxyl, oxyacylamino, azido, cyano, halogen, hydroxyl, keto, thioketo, carboxyl, carboxylalkyl, thiol, thioalkoxyl, substituted thioalkoxyl, aryl, aryloxyl, thioaryloxyl, heteroaryl, heteroaryloxyl, thioheteroaryloxyl, heterocyclic, heterocyclooxyl, thioheterocyclooxyl, nitro, and —NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic. Additionally, such substituted alkylene groups include, without limitation, those where 2 substituents on the alkylene group are fused to form one or more cycloalkyl, substituted cycloalkyl, cycloalkenyl, substituted cycloalkenyl, aryl, heterocyclic or heteroaryl groups fused to the alkylene group; (2) an alkylene group as defined above that is interrupted by 1–20 atoms independently chosen from oxygen, sulfur and NR$^a$, where R$^a$ is chosen from hydrogen, optionally substituted alkyl, cycloalkyl, alkenyl, cycloalkenyl, alkenyl, cycloalkenyl, alkynyl, aryl, heteroaryl and heterocyclic, or groups selected from carbonyl, carboxyester, carboxyamide and sulfonyl; or (3) an alkylene group as defined above that has both from 1 to 5 substituents as defined above and is also interrupted by 1 to 20 atoms as defined above. Examples of substituted alkylenes are chloromethylene (—CH(Cl)—), aminoethylene (—CH(NH$_2$)CH$_2$—), 2-carboxypropylene isomers (—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), 1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

"Alkynyl" is intended to include hydrocarbon chains of either a straight or branched configuration and one or more triple carbon-carbon bonds which may occur in any stable point along the chain, such as ethynyl, propynyl and the like. For example, alkynyl refers to an unsaturated acyclic hydrocarbon radical in so much as it contains one or more triple bonds, such radicals containing about 2 to about 40 carbon atoms, preferably having from about 2 to about 10 carbon atoms and more preferably having 2 to about 6 carbon atoms. Non-limiting examples of suitable alkynyl radicals include, ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

"Alicyclic hydrocarbon" means a aliphatic radical in a ring with 3 to about 10 carbon atoms, and preferably from 3 to about 6 carbon atoms. Examples of suitable alicyclic radicals include, without limitation, cyclopropyl, cyclopropylenyl, cyclobutyl, cyclopentyl, cyclohexyl, 2-cyclohexen-1-ylenyl, cyclohexenyl and the like.

"Alkoxyalkyl" embraces alkyl radicals having one or more alkoxy radicals attached to the alkyl radical, that is, to form monoalkoxyalkyl and dialkoxyalkyl radicals. The "alkoxy" radicals may be further substituted with one or more halo atoms, such as fluoro, chloro or bromo, to provide haloalkoxy radicals. More preferred haloalkoxy radicals are "lower haloalkoxy" radicals having one to six carbon atoms and one or more halo radicals. Examples of such radicals include, without limitation, fluoromethoxy, chloromethoxy, trifluoromethoxy, trifluoromethoxy, fluoroethoxy and fluoropropoxy. Further "alkoxycarbonyl" means a radical containing an alkoxy radical, as defined above, attached via an oxygen atom to a carbonyl radical. More preferred are "lower alkoxycarbonyl" radicals with alkyl portions having 1 to 6 carbons. Examples of such lower alkoxycarbonyl (ester) radicals include, without limitation, substituted or unsubstituted methoxycarbonyl, ethoxycarbonyl, propoxycarbonyl, butoxycarbonyl and hexyloxycarbonyl.

"Aminoalkyl" embraces alkyl radicals substituted with amino radicals. More preferred are "lower aminoalkyl" radicals. Examples of such radicals include, without limitation, aminomethyl, aminoethyl, and the like.

"Aminocarbonyl" denotes an amide group of the formula —C(=O)NH$_2$.

"Aralkoxy" embraces aralkyl radicals attached through an oxygen atom to other radicals.

"Aralkoxyalkyl" embraces aralkoxy radicals attached through an oxygen atom to an alkyl radical.

"Aralkyl" embraces aryl-substituted alkyl radicals such as benzyl, diphenylmethyl, triphenylmethyl, phenylethyl, and diphenylethyl. The aryl in said aralkyl may be additionally substituted with halo, alkyl, alkoxy, halkoalkyl and haloalkoxy.

"Aralkylamino" embraces aralkyl radicals attached through an nitrogen atom to other radicals.

"Aralkylthio" embraces aralkyl radicals attached to a sulfur atom.

"Aralkylthioalkyl" embraces aralkylthio radicals attached through a sulfur atom to an alkyl radical.

"Aromatic hydrocarbon radical" means 4 to about 16 carbon atoms, preferably 6 to about 12 carbon atoms, more preferably 6 to about 10 carbon atoms. Example of suitable aromatic hydrocarbon radicals include, without limitation, phenyl, naphthyl, and the like.

"Aroyl" embraces aryl radicals with a carbonyl radical as defined above. Examples of aroyl include, without limitation, benzoyl, naphthoyl, and the like and the aryl in said aroyl may be additionally substituted.

"Arylamino" denotes amino groups which have been substituted with one or two aryl radicals, such as N-phenylamino. Arylamino radicals may be further substituted on the aryl ring portion of the radical.

"Aryloxyalkyl" embraces radicals having an aryl radical attached to an alkyl radical through a divalent oxygen atom.

"Arylthioalkyl" embraces radicals having an aryl radical attached to an alkyl radical through a divalent sulfur atom.

"Carbonyl", whether used alone or with other terms, such as "alkoxycarbonyl", denotes —(C=O)—.

"Carboxy" or "carboxyl", whether used alone or with other terms, such as "carboxyalkyl", denotes —CO$_2$H.

"Carboxyalkyl" embraces alkyl radicals substituted with a carboxy radical. More preferred are "lower carboxyalkyl" which embrace lower alkyl radicals as defined above, and may be additionally substituted on the alkyl radical with halo. Examples of such lower carboxyalkyl radicals include, without limitation, carboxymethyl, carboxyethyl and carboxypropyl.

"Cycloalkenyl" embraces partially unsaturated carbocyclic radicals having three to twelve carbon atoms. More preferred cycloalkenyl radicals are "lower cycloalkenyl" radicals having four to about eight carbon atoms. Examples of such radicals include, without limitation, cyclobutenyl, cyclopentenyl and cyclohexenyl.

"Cycloalkyl" embraces saturated carbocyclic radicals having three to twelve carbon atoms. More preferred cycloalkyl radicals are "lower cycloalkyl" radicals having three to about eight carbon atoms. Examples of such radicals include, without limitation, cyclopropyl, cyclobutyl, cyclopentyl and cyclohexyl.

"Hydroxyalkyl" embraces linear or branched alkyl radicals having one to about twenty carbon atoms any one of which may be substituted with one or more hydroxyl radicals. Preferred hydroxyalkyl radicals are "lower hydroxyalkyl" radicals having one to six carbon atoms and one or more hydroxyl radicals. Non-limiting examples of such radicals include hydroxymethyl, hydroxyethyl, hydroxypropyl, hydroxybutyl and hydroxyhexyl.

"Sulfamyl", "aminosulfonyl" and "sulfonamidyl" denote NH$_2$O$_2$S—.

"Sulfonyl", whether used alone or linked to other terms such as alkylsulfonyl, denotes respectively divalent radicals —SO$_2$—.

"Alkenyl" is intended to include hydrocarbon chains of either a straight or branched configuration and one or more unsaturated carbon-carbon bonds which may occur in any stable point along the chain. For example, alkenyl refers to an unsaturated acyclic hydrocarbon radical in so much as it contains at least one double bond. Such radicals containing from about 2 to about 40 carbon atoms, preferably from about 2 to about 10 carbon atoms and more preferably about 2 to about 6 carbon atoms. Non-limiting examples of suitable alkenyl radicals include propylenyl, buten-1-yl, isobutenyl, penten-1-yl, 2-2-methylbuten-1-yl, 3-methylbuten-1-yl, hexen-1-yl, hepten-1-yl, and octen-1-yl, and the like.

"Alkoxyl" represents an alkyl group of indicated number of carbon atoms attached through an oxygen bridge. "Alkoxy" and "alkyloxy" embrace linear or branched oxy-containing radicals each having alkyl portions of one to about ten carbon atoms. More preferred alkoxy radicals are "lower alkoxy" radicals having one to six carbon atoms. Examples of such radicals include, without limitation, methoxy, ethoxy, propoxy, butoxy and tert-butoxy.

"Aryl" refers to an unsaturated aromatic carbocyclic group of from 6 to 20 carbon atoms having a single ring (e.g., phenyl) or multiple condensed (fused) rings (e.g., naphthyl or anthryl). "aryl" embraces aromatic radicals such as phenyl, naphthyl, tetrahydronaphthyl, indane and biphenyl. Unless otherwise constrained by the definition for the aryl substituent, such aryl groups can optionally be substituted with from 1 to 5 substituents selected from a member of the group consisting of acyloxyl, hydroxyl, thiol, acyl, alkyl, alkoxyl, alkenyl, alkynyl, cycloalkyl, cycloalkenyl, substituted alkyl, substituted alkoxyl, substituted alkenyl, substituted alkynyl, substituted cycloalkyl, substituted cycloalkenyl, aminoacyl, acylamino, alkaryl, aryl, aryloxyl, azido, carboxyl, carboxylalkyl, cyano, halo, nitro, heteroaryl, heteroaryloxyl, heterocyclic, heterocyclooxyl, aminoacyloxyl, oxyacylamino, thioalkoxyl, substituted thioalkoxyl, thioaryloxyl, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, trihalomethyl, NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic. Preferred aryl substituents include, without limitation, without limitation, alkyl, alkoxyl, halo, cyano, nitro, trihalomethyl, and thioalkoxy (i.e., —S-alkyl).

"N-arylaminoalkyl" and "N-aryl-N-alkyl-aminoalkyl" denote amino groups which have been substituted with one aryl radical or one aryl and one alkyl radical, respectively, and having the amino group attached to an alkyl radical. Examples of such radicals include, without limitation, N-phenylaminomethyl and N-phenyl-N-methylaminomethyl.

"Carbocycle" or "carbocyclic group" is intended to mean any stable 3 to 7 membered monocyclic or bicyclic or 7 to 14 membered bicyclic or tricyclic or an up to 26 membered polycyclic carbon ring, any of which may be saturated, partially unsaturated, or aromatic.

"Substituted carbocycle" or "substituted carbocyclic group" refers to carbocyclic groups having from 1 to 5 substituents selected from a member of the group consisting of alkoxyl, substituted alkoxyl, cycloalkyl, cycloalkenyl, substituted cycloalkenyl, acyl, acylamino, acyloxyl, amino, aminoacyl, aminoacyloxyl, oxyaminoacyl, azido, cyano, halogen, hydroxyl, keto, thioketo, carboxyl, carboxylalkyl, thioaryloxyl, thioheteroaryloxyl, thioheterocyclooxyl, thiol, thioalkoxyl, substituted thioalkoxyl, aryl, aryloxyl, heteroaryl, heteroaryloxyl, heterocyclic, heterocyclooxyl, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic. Preferred examples of carbocyclic groups include, without limitation, members selected from the group consisting of adamantyl, anthracenyl, benzamidyl, benzyl, bicyclo[2.2.1]heptanyl, bicyclo[2.2.1]hexanyl, bicyclo[2.2.2]octanyl, bicyclo[3.2.0]heptanyl, bicyclo[4.3.0]nonanyl, bicyclo[4.4.0]decanyl, biphenyl, biscyclooctyl, cyclobutanyl (cyclobutyl), cyclobutenyl, cycloheptanyl (cycloheptyl), cycloheptenyl, cyclohexanedionyl, cyclohexenyl, cyclohexyl, cyclooctanyl, cyclopentadienyl, cyclopentanedionyl, cyclopentenyl, cyclopentyl, cyclopropyl, decalinyl, 1,2-diphenylethanyl, indanyl, 1-indanonyl, indenyl, naphthyl, naphthlalenyl, phenyl, resorcinolyl, stilbenzyl, tetrahydronaphthyl (tetralin), tetralinyl, tetralonyl, tricyclododecanyl, and the like.

"Cycloalkyl" is intended to include saturated ring groups, including mono-, bi- or poly-cyclic ring systems, such as, without limitation, cyclopropyl, cyclobutyl, cyclopentyl, cyclohexyl, cycloheptyl, cyclooctyl, and adamantyl. "Bicycloalkyl" is intended to include saturated bicyclic ring groups such as, without limitation, [3.3.0]bicyclooctane, [4.3.0]bicyclononane, [4.4.0]bicyclodecane (decalin), [2.2.2]bicyclooctane, and so forth.

"Halo" or "halogen" as used herein refers to fluoro, chloro, bromo and iodo; and "counterion" is used to represent a small, negatively charged species such as chloride, bromide, hydroxide, acetate, sulfate and the like.

"Haloalkyl" is intended to include both branched and straight-chain saturated aliphatic hydrocarbon groups having the specified number of carbon atoms, substituted with 1 or more halogen. Haloalkyl embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Non-limiting examples of haloalkyl radicals include fluoromethyl, difluoromethyl, trifluoromethyl, chloromethyl, dichloromethyl, trichloromethyl, pentafluoroethyl, heptafluoropropyl, diflurochloromethyl, dichlorofluoromethyl, difluoroethyl, difluoropropyl, dichloroethyl and dichloropropyl.

"Heterocycle" or "heterocyclic group" refers to a saturated or unsaturated group having a single ring, multiple condensed rings or multiple covalently joined rings, from 1 to 40 carbon atoms and from 1 to 10 hetero ring atoms, preferably 1 to 4 hetero ring atoms, selected from nitrogen, sulfur, phosphorus, and/or oxygen. Preferably, "heterocycle" or "heterocyclic group" means a stable 5 to 7 membered monocyclic or bicyclic or 7 to 10 membered bicyclic heterocyclic ring that may be saturated, partially unsaturated, or aromatic, and that comprises carbon atoms and from 1 to 4 heteroatoms independently selected from a member of the group consisting of nitrogen, oxygen and sulfur and wherein the nitrogen and sulfur heteroatoms are optionally be oxidized and the nitrogen heteroatom may optionally be quaternized, and including any bicyclic group in which any of the above define heterocyclic rings is fused to a benzene ring. The heterocyclic groups may be substituted on carbon or on a nitrogen, sulfur, phosphorus, and/or oxygen heteroatom so long as the resulting compound is stable. Unless otherwise constrained by the definition for the heterocyclic substituent, such heterocyclic groups can be optionally substituted with 1 to 5, and preferably 1 to 3 substituents. Suitable, but non-limiting, examples of such substituents include members selected from the group consisting of alkoxy, substituted alkoxy, cycloalkyl, substituted cycloalkyl, cycloalkenyl, substituted cycloalkenyl, acyl, acylamino, acyloxyl, aminoacyl, aminoacyloxyl, oxyaminoacyl, cyano, halogen, hydroxyl, keto, thioketo, carboxyl, carboxylalkyl, thioaryloxyl, thioheteroaryloxyl, thioheterocyclooxyl, thiol, thioalkoxyl, substituted thioalkoxy, aryl, aryloxyl, heteroaryl, heteroaryloxyl, heterocyclic, heterocyclooxyl, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO,-heteroaryl, and NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic.

Suitable examples of such heterocyclic groups include, without limitation, acridinyl, acridonyl, adeninyl, alkylpyridinyl, alloxanyl, alloxazinyl, anthracenyl, anthranilyl, anthraquinonly, anthrenyl, ascorbyl, azaazulenyl, azabenzanthracenyl, azabenzanthrenyl, azabenzonaphthenyl, azabenzophenanthrenyl, azachrysenyl, azacyclazinyl, azaindolyl, azanaphthacenyl, azanaphthalenyl, azaphenoxazinyl, azapinyl, azapurinyl, azapyrenyl, azatriphenylenyl, azepinyl, azetidinedionyl, azetidinonyl, azetidinyl, azinoindolyl, azinopyrrolyl, azinyl, aziridinoyl, aziridinyl, azirinyl, azocinyl, azoloazinyl, azolyl, barbituric acid, benzacridinyl, benzazapinyl, benzazinyl, benzimidazolethionyl, benzimidazolonyl, benzimidazolyl, benzisothiazolyl, benzisoxazolyl, benzocinnolinyl, benzodiazocinyl, benzodioxanyl, benzodioxolanyl, benzodioxolyl, benzofuranyl (benzofuryl), benzofuroxanyl, benzonaphthyridinyl, benzopyranoyl (benzopyranyl), benzopyidazinyl, benzopyronyl, benzoquinolinyl, benzoquinolizinyl, benzothiadiazinyl, benzothiazepinyl, benzothiazinyl, benzothiazolyl, benzothiepinyl, benzothiophenyl, benzotriazepinonyl, benzotriazolyl, benzoxadizinyl, benzoxazinyl, benzoxazolinonyl, benzoxazolyl, benzylisoquinolinyl, beta-carbolinyl, biotinyl, bipyridinyl, butenolidyl, butyrolactonyl, caprolactamyl, carbazolyl, 4a H-carbazoyl, carbolinyl, catechinyl, chromanyl, chromemopyronyl, chromonopyranyl, chromylenyl, cinnolinyl, coumarinyl, coumaronyl, decahydroquinolinyl, decahydroquinolonyl, depsidinyl, diazaanthracenyl, diazaphenanthrenyl, diazepinyl, diazinyl, diaziridinonyl, diaziridinyl, diazirinyl, diazocinyl, dibenzazepinyl, dibenzofuranyl, dibenzothiophenyl, dibenzoxazepinyl, dichromylenyl, dihydrobenzimidazolyl, dihydrobenzothiazinyl, dihydrofuranyl, dihydroisocoumarinyl, dihydroisoquinolinyl, dihydrooxazolyl, dihydropyranyl, dihydropyridazinyl, dihydropyridinyl, dihydropyridonyl, dihydropyrimidinyl, dihydropyronyl, dihydrothiazinyl, dihydrothiopyranyl, dihydroxybenzenyl, dimethoxybenzenyl, dimethylxanthinyl, dioxadiazinyl, dioxanthylenyl, dioxanyl, dioxenyl, dioxepinyl, dioxetanyl, dioxinonyl, dioxonyl, dioxiranyl, dioxolanyl, dioxolonyl, dioxolyl, dioxopiperazinyl, diprylenyl, dipyrimidopyrazinyl, dithiadazolyl, dithiazolyl, 2H,6H-1,5,2-dithiazinyl, dithietanyl, dithiolanyl, dithiolenyl, dithiolyl, enantholactamyl, episulfonyl, flavanyl, flavanvl, flavinyl, flavonyl, fluoranyl, fluorescienyl, furandionyl, furanochromanyl, furanonyl, furanoquinolinyl, furanyl (furyl), furazanyl, furfuryl, furopyranyl, furopyrimidinyl, furopyronyl, furoxanyl, glutarimidyl, glycocyamidinyl, guaninyl, heteroazulenyl, hexahydropyrazinoisoquinolinyl, hexahydropyridazinyl, homophthalimidyl, hydrantoinyl, hydrofuranyl, hydrofumanonyl, hydroimidazolyl, hydroindolyl, hydropyranyl, hydropyrazinyl, hydropyrazolyl, hydropyridazinyl, hydropyridinyl, hydropyrimidinyl, hydropyrrolyl, hydroquinolinyl, hydrothiochromenyl, hydrothiophenyl, hydrotriazolyl, hydroxytrizinyl, imidazolethionyl, imidazolindinyl, imidazolinyl, imidazolonyl, imidazolyl, imidazoquinazolinyl, imidazothiazolyl, indazolebenzopyrazolyl, indazolyl, 1H-indazoyl, indolenyl, indolinyl, indolizidinyl, indolizinyl, indolonyl, indolyl, 3H-indolyl, indoxazenyl, inosinyl, isatinyl, isatogenyl, isoalloxazinyl, isobenzofurandionyl, isobenzofuranyl, isochromanyl, isoflavonyl, isoindolinyl (isoindolyl), isoindolobenzazepinyl, isoquinolinyl, isoquinuclidinyl, isothiazolyl, isoxazolidinyl, isoxazolinonyl, isoxazolinyl, isoxazolonyl, isoxazolyl, lactamyl, lactonyl, lumazinyl, maleimidyl, methylbenzamidyl, methylbenzoyleneureayl, methyldihydrouracilyl, methyldioxotetrahydropteridinyl, methylpurinyl, methylthyminyl, methylthyminyl, methyluracilyl, methylxanthinyl, monoazabenzonaphthenyl, morpholinyl (morpholino), naphthacenyl, naphthalenyl, naphthimidazolyl, naphthimidazopyridinedionyl, naphthindolizinedionyl, naphthodihydropyranyl, naphthofuranyl, naphthothiophenyl, naphthylpyridinyl, naphthyridinyl, octahydroisoquinolinyl, octylcarboxamidobenzenyl, oroticyl, oxadiazinyl, oxadiazolyl, oxathianyl, oxathiazinonyl, oxathietanyl, oxathiiranyl, oxathiolanyl, oxatriazolyl, oxazinonyl, oxaziranyl, oxaziridinyl, oxazolidinonyl, oxazolidinyl, oxazolidonyl, oxazolinonyl, oxazolinyl, oxazolonyl, oxazolopyrimidinyl, oxazolyl, oxepinyl, oxetananonyl, oxetanonyl, oxetanyl, oxindolyl, oxiranyl, oxolenyl, pentazinyl, pentazolyl, perhydroazolopyridinyl, perhydroicinnolinyl, perhydroindolyl, perhydropyrroloazinyl, perhydropyrrolooxainyl, perhydropyrrolothiazinyl, perhydrothiazinonyl, perimidinyl, petrazinyl, phenanthraquinonyl, phenanthridinyl, phenanthrolinyl, phenarsazinyl, phenazinyl, phenothiazinyl, phenoxanthinyl, phenoxazinyl, phenoxazonyl, phthalazinyl, phthalideisoquinolinyl, phthalimidyl, phthalonyl, piperazindionyl, piperazinodionyl, piperazinyl, piperidinyl, piperidonyl, 4-piperidonyl, polyoxadiazolyl, polyquinoxalinyl, prolinyl, prylenyl, pteridinyl, pterinyl, purinyl, pyradinyl, pyranoazinyl, pyranoazolyl, pyranonyl, pyranopyradinyl, pyranopyrandionyl, pyranopyridinyl, pyranoquinlinyl, pyranyl, pyrazinyl, pyrazolidinyl, pyrazolidonyl, pyrazolinonyl, pyrazolinyl, pyrazolobenzodiazepinyl, pyrazolonyl, pyrazolopyridinyl, pyrazolopyrimidinyl, pyrazolotriazinyl, pyrazolyl, pyrenyl, pyridazinyl, pyridazonyl, pyridinethionyl, pyridinonanphthalenyl, pyridinopyridinyl, pyridocolinyl, pyridoindolyl, pyridopyraziyl, pyridopyridinyl, pyridopyrimidinyl, pyridopyrrolyl, pyridoquinolinyl, pyridyl (pyridinyl), pyrimidinethionyl, pyrimidinyl, pyrimidionyl, pyrimidoazepinyl, pyrimidopteridinyl, pyronyl, pyrrocolinyl, pyrrolidinyl, 2-pyrrolidinyl, pyrrolinyl, pyrrolizidinyl, pyrrolizinyl, pyrrolobenzodiazepinyl, pyrrolodiazinyl, pyrrolonyl, pyrrolopyrimidinyl, pyrroloquinolonyl, pyrrolyl, 2H-pyrrolyl, quinacridonyl, quinazolidinyl, quinazolinonyl, quinazolinyl, quinolinyl, quinolizidinyl, quinolizinyl, 4H-quinolizinyl, quinolonyl, quinonyl, quinoxalinyl, quinuclidinyl, quinuclidinyl, rhodaminyl, spirocoumaranyl, succinidimiyl, sulfolanyl, sulfolenyl, sultamyl, sultinyl, sultonyl, sydononyl, tetrahydrofuranyl, tetrahydroisoquinolinyl, tetrahydrooxazolyl, tetrahydropyranyl, tetrahydropyrazinyl, tetrahydropyridazinyl, tetrahydropyridinyl, tetrahydroquinolinyl, tetrahydroquinoxalinyl, tetrahydrothiapyranyl, tetrahydrothiazolyl, tetrahydrothiophenyl, tetrahydrothiopyranonyl, tetrahydrothiopyranyl, tetraoxanyl, tetrazepinyl, tetrazinyl, tetrazolyl, tetronyl, thiabenzenyl, thiachromanyl, thiadecalinyl, thiadiazinyl, 6H-1,2,5-thiadiazinyl, thiadiazolinyl, thiadiazolyl, thiadioxazinyl, thianaphthenyl, thianthrenyl, thiapyranyl, thiapyronyl, thiatriazinyl, thiatriazolyl, thiazepinyl, thiazetidinyl, thiazinyl, thiaziridinyl, thiazolidinonyl, thiazolidinyl, thiazolinonyl, thiazolinyl, thiazolobenzimidazolyl, thiazolopyridinyl, thiazolyl, thienopyridinyl, thienopyrimidinyl, thienopyrrolyl, thienothiophenyl, thienyl, thiepinyl, thietanyl, thiiranyl, thiochromenyl, thiocoumarinyl, thiolanyl, thiolenyl, thiolyl, thiophenyl, thiopyranyl, thyminyl, triazaathracenyl, triazepinonyl, triazepinyl, triazinoindolyl, triazinyl, triazolinedionyl, triazolinyl, triazolopyridinyl, triazolopyrimidinyl, triazolyl, trioxanyl, triphenodioxazinyl, triphenodithiazinyl, trithiadiazepinyl, trithianyl, trixolanyl, trizinyl, tropanyl, uracilyl, xanthenyl, xanthinyl, xanthonyl, xanthydrolyl, xyliolyl, and the like as well as N-alkoxy-nitrogen containing heterocycles. Preferred heterocyclic groups include, without limitation, members of the group consisting of acridinyl, aziridinyl, azocinyl, azepinyl, benzimidazolyl, benzodioxolanyl, benzofuranyl, benzothiophenyl, carbazole, 4a H-carbazole, chromanyl, chromenyl, cinnolinyl, decahydroquinolinyl, dioxoindolyl, furazanyl, furyl, furfuryl, imidazolidinyl, imidazolinyl, imidazolyl, 1H-indazolyl, indolenyl, indolinyl, indolizinyl, indolyl, 3H-indolyl, isobenzofuranyl, isochromanyl, isoindolinyl, isoindolyl, isoquinolinyl, isothiazolyl, isoxazolyl, morpholinyl, naphthalenyl, naphthyridinyl, norbomanyl, norpinanyl, octahydroisoquinolinyl, oxazolidinyl, oxazolyl, oxiranyl, perimidinyl, phenanthridinyl, phenanthrolinyl, phenaraszinyl, phenazinyl, phenothiazinyl, phenoxathiinyl, phenoxazinyl, phenyl, phthalazinyl, piperazinyl, piperidinyl, 4-piperidonyl, piperidyl, pteridinyl, pyrinyl, pyranyl, pyrazinyl, pyrazolidinyl, pyrazolinyl, pyrazolyl, pyrenyl, pyridazinyl, pyridinyl, pyridyl, pyridyl, pyrimidinyl, pyrrolidinyl, 2-pyrrolidonyl, pyrrolonyl, pyrrolyl, 2H-pyrrolyl, quinazolinyl, 4H-quinolizinyl, quinolinyl, quinoxalinyl, quinuclidinyl, β-carbolinyl, tetrahydrofuranyl, tetrahydroisoquinolinyl, tetrahydroquinolinyl, tetrazolyl, 6H-1,2,5-thiadiazinyl, 2H-1,5,2-dithiazinyl, thianthrenyl, thiazolyl, thienyl, thiophenyl, triazinyl, xanthenyl, xanthinyl, and the like.

"Pharmaceutically acceptable derivative" or "prodrug" means any pharmaceutically acceptable salt, ester, salt of an ester, or other derivative of a compound of the present invention which, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood) or that enhance delivery of the parent compound to a biological compartment (e.g., the brain or lymphatic system) relative to the parent species. Prodrugs are considered to be any covalently bonded carriers which release the active parent drug according to Formula I or II in vivo when such prodrug is administered to a mammalian subject. Preferred prodrugs include, without limitation, derivatives where a group that enhances aqueous solubility or active transport through the gut membrane is appended to the structure of Formula I or II. Prodrugs of the compounds of Formula I or II are prepared by modifying functional groups present in the compounds in such a way that the modifications are cleaved, either in routine manipulation or in vivo, to the parent compounds. Prodrugs include compounds of Formula I or II wherein hydroxyl, amino, sulfhydryl, or carboxyl groups are bonded to any group that, when administered to a mammalian subject, cleaves to form a free hydroxyl, amino, sulfhydryl, or carboxyl group, respectively. Examples of prodrugs include, but are not limited to, acetate, formate and benzoate derivatives of alcohol and amine functional groups in the compounds of Formula I or II, and the like.

"Pharmaceutically acceptable salts" refer to derivatives of the disclosed compounds wherein the parent compound of Formula I or II is modified by making acid or base salts of the compound of Formula I or II. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the compounds of Formula I or II include the conventional nontoxic salts or the quaternary ammonium salts of the compounds of Formula I or II formed, for example, from nontoxic inorganic or organic acids. For example, such conventional non-toxic salts include, without limitation, those derived from inorganic acids such as acetic, 2-acetoxybenzoic, adipic, aliginic, ascorbic, aspartic, benzoic, benzenesulfonic, bisulfic, butyric, citric, camphoric, camphorsulfonic, cyclopentanepropionic, digluconic, dodecylsulfanilic, ethane disulfonic, ethanesulfonilic, fumaric, glucoheptanoic, glutamic, glycerophosphic, glycolic, hemisulfanoic, heptanoic, hexanoic, hydrochloric, hydrobromic, hydroiodic, 2-hydroxyethanesulfonic, hydroxymaleic, isethionic, lactic, malic, maleic, methanesulfonic, 2-naphthalenesulfonic, nicotinic, nitric, oxalic, palmic, pamoic, pectinic, persulfanilic, phenylacetic, phosphoric, propionic, pivalic, propionate, salicyclic, succinic, stearic, sulfuric, sulfamic, sulfanilic, tartaric, thiocyanic, toluenesulfonic, tosylic, undecanoatehydrochloric, and the like. The pharmaceutically acceptable salts of the present invention can be synthesized from the compounds of Formula I or II which contain a basic or acidic moiety by conventional chemical methods, for example, by reacting the free base or acid with stoichiometric amounts of the appropriate base or acid, respectively, in water or in an organic solvent, or in a mixture of the two (nonaqueous media like ether, ethyl acetate, ethanol, isopropanol, or acetonitrile are preferred) or by reacting the free base or acid with an excess of the desired salt-forming inorganic or organic acid or base in a suitable solvent or various combinations of solvents. Lists of suitable salts are found in *Remington's Pharmaceutical Sciences*, 17th ed., Mack Publishing Company, Easton, Pa. 1985, p. 1418, et al., the entire disclosure of which is incorporated herein by reference.

"Pharmaceutically effective" or "therapeutically effective" amount of a compound of the present invention is an amount that is sufficient to effect treatment, as defined above, when administered to a mammal in need of such treatment. The amount will vary depending upon the subject and disease condition being treated, the weight and age of the subject, the severity of the disease condition, the manner of administration and the like, which can be readily determined by one of skill in the art.

"Cellular process or activity mediated by IL-1" and "IL-12 mediated processes and activities," as used herein includes IL-12 initiated cellular processes and activities, for example, the direct stimulation of IFN-γ production by resting T cells and NK cells. This term also includes the IL-12 modulation of ongoing processes and activities, for example, the enhancement of anti-CD3 induced IFN-γ secretion. Various other IL-12-mediated processes and activities are intended to be encompassed by this term, for example, the differentiation of naive T cells into Th1 cells; maintenance of the Th1 phenotype (e.g., high IFN-γ production, low IL-4 production); proliferation of T cell blasts; enhancement of NK cell and CTL cytolytic activity, and the like. For additional examples, see Trichieri, *Annu. Rev. Immunol.* 13: 251–76 (1995).

"Treatment" refers to any treatment of an IL-12 mediated disease or condition in a mammal, particularly a human, and includes, without limitation: (i) preventing the disease or condition from occurring in a subject which may be predisposed to the condition but has not yet been diagnosed with the condition and, accordingly, the treatment constitutes prophylatic treatment for the pathologic condition; (ii) inhibiting the disease or condition, i.e., arresting its development; (iii) relieving the disease or condition, i.e., causing regression of the disease or condition; or (iv) relieving the symptoms resulting from the disease or condition, e.g., relieving an inflammatory response without addressing the underlining disease or condition.

The present invention also envisions the quaternization of any basic nitrogen-containing groups of the compounds disclosed herein. The basic nitrogen can be quaternized with any agents known to those of ordinary skill in the art including, without limitation, lower alkyl halides, such as methyl, ethyl, propyl and butyl chlorides, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

In addition to their structural characteristics, the compounds of the present invention share an ability to inhibit IL-12 signaling. A skilled artisan or scientist using routine protocols or assays, such as the assays disclosed in the Examples below or in the literature, may readily confirm the utility of the compounds disclosed herein.

Without being bound by the above general structural descriptions/definitions, preferred compounds of the present invention having utility for inhibiting IL-12 signaling according to the present invention, include, but are not limited to the following compounds. It will be appreciated, as noted above, that where an R or S enantiomer is exemplified for each particular compound, the corresponding S or R enantiomer, respectively, is also intended even though it may not be specifically shown below.

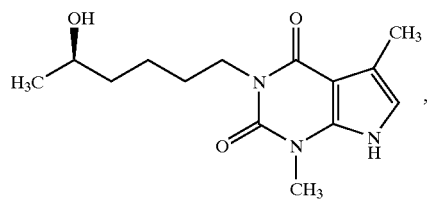

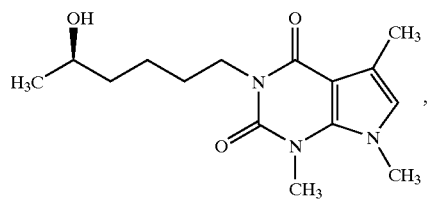

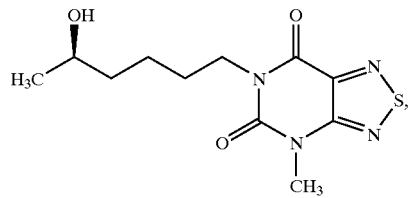

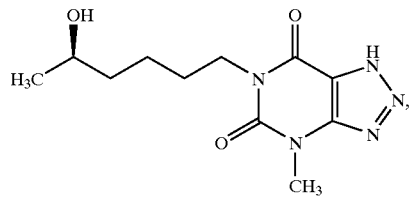

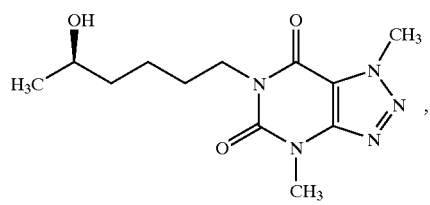

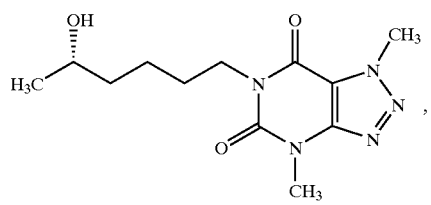

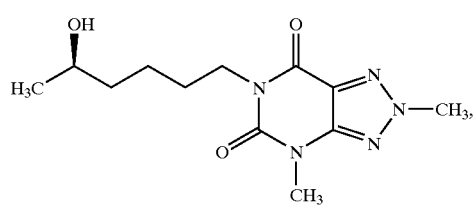

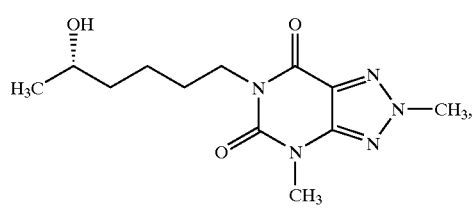

23
24
-continued
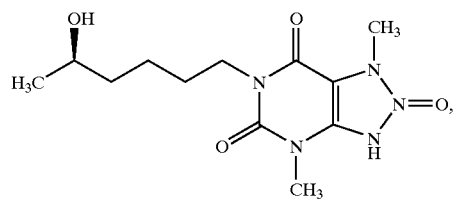
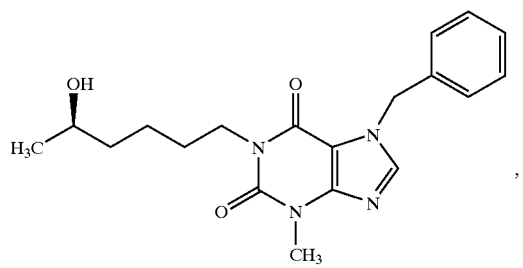
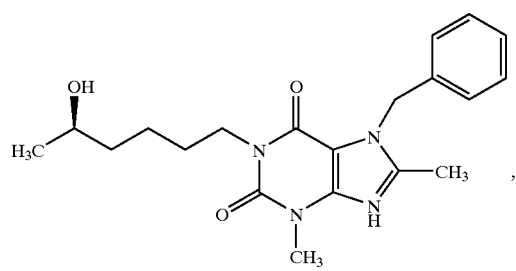
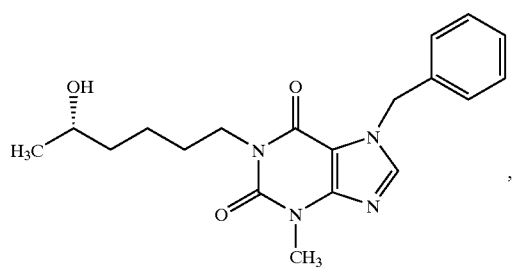
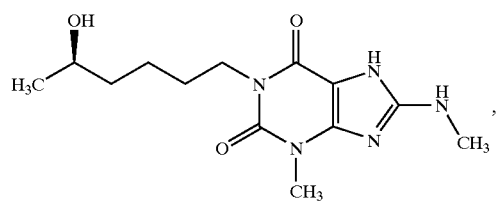
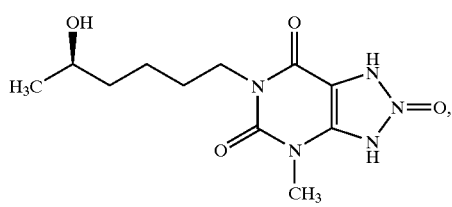
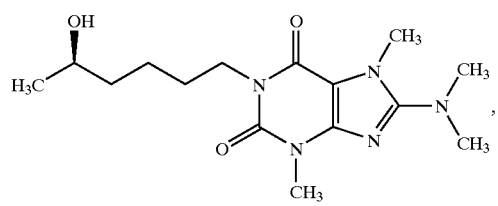
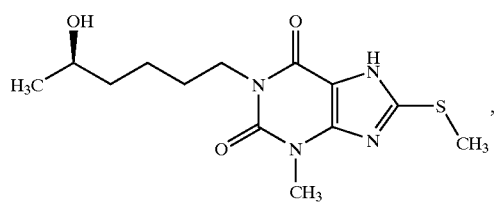
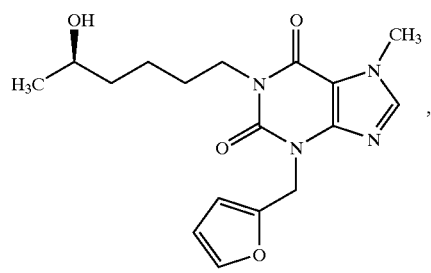
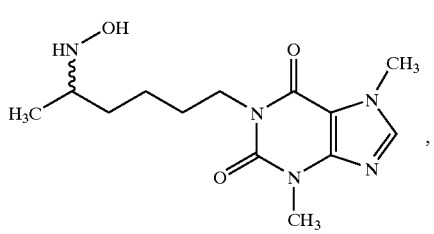
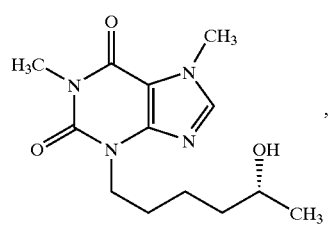
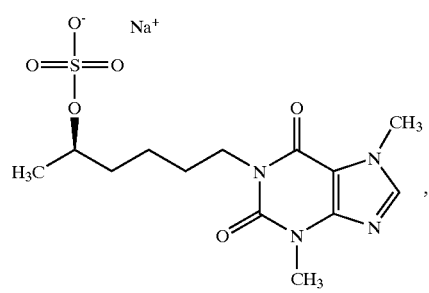

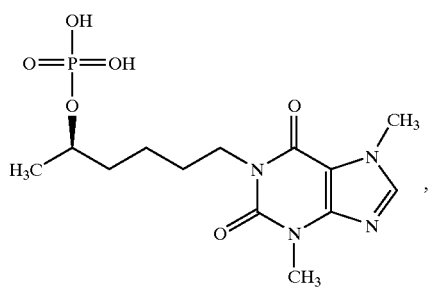
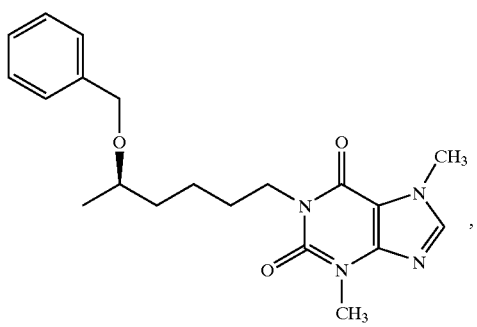
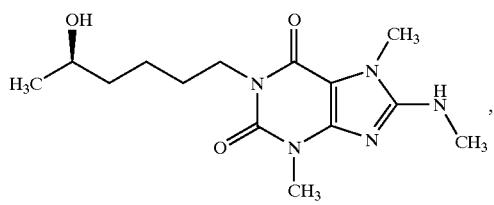
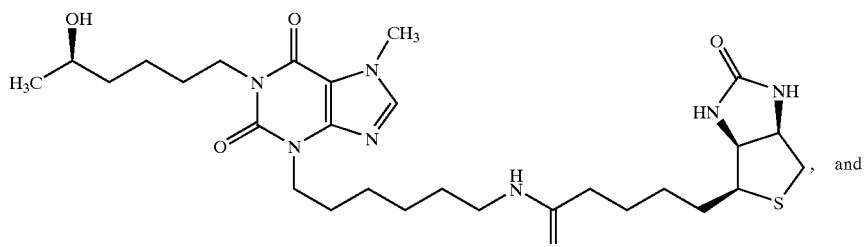
, and
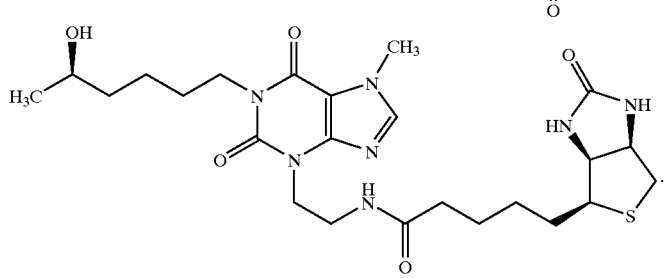
More preferred compounds of the present invention having utility for inhibiting IL-12 signaling include without limitation, the following:
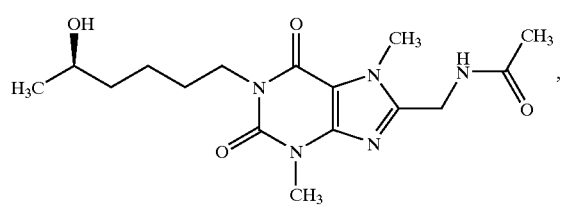
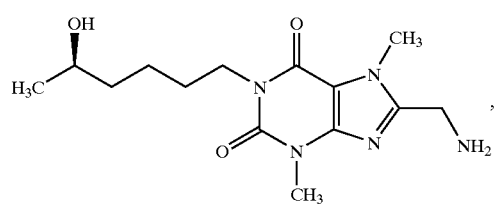
-continued
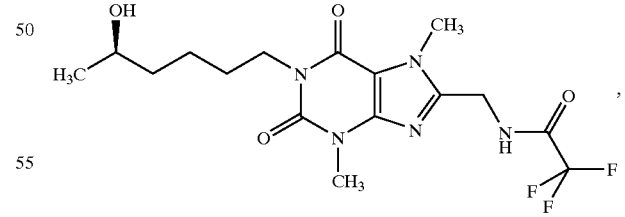
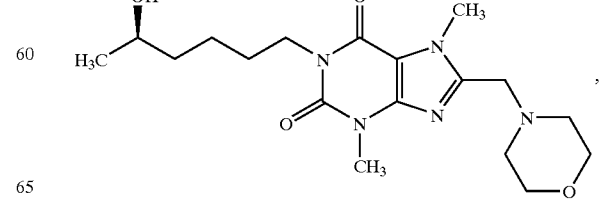

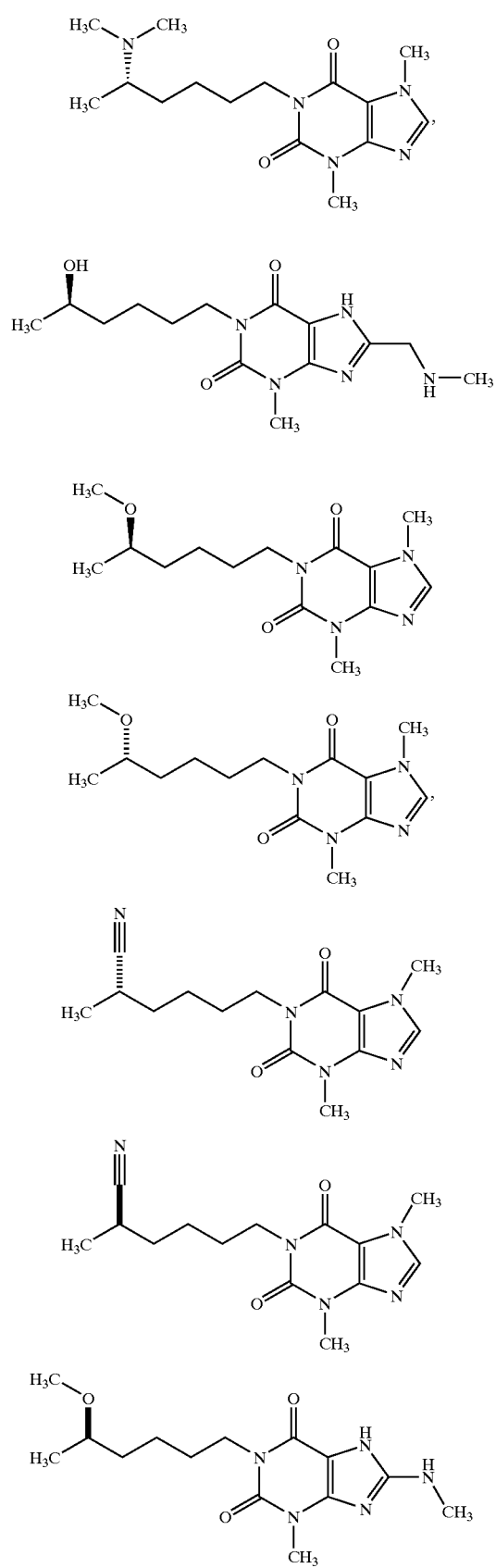
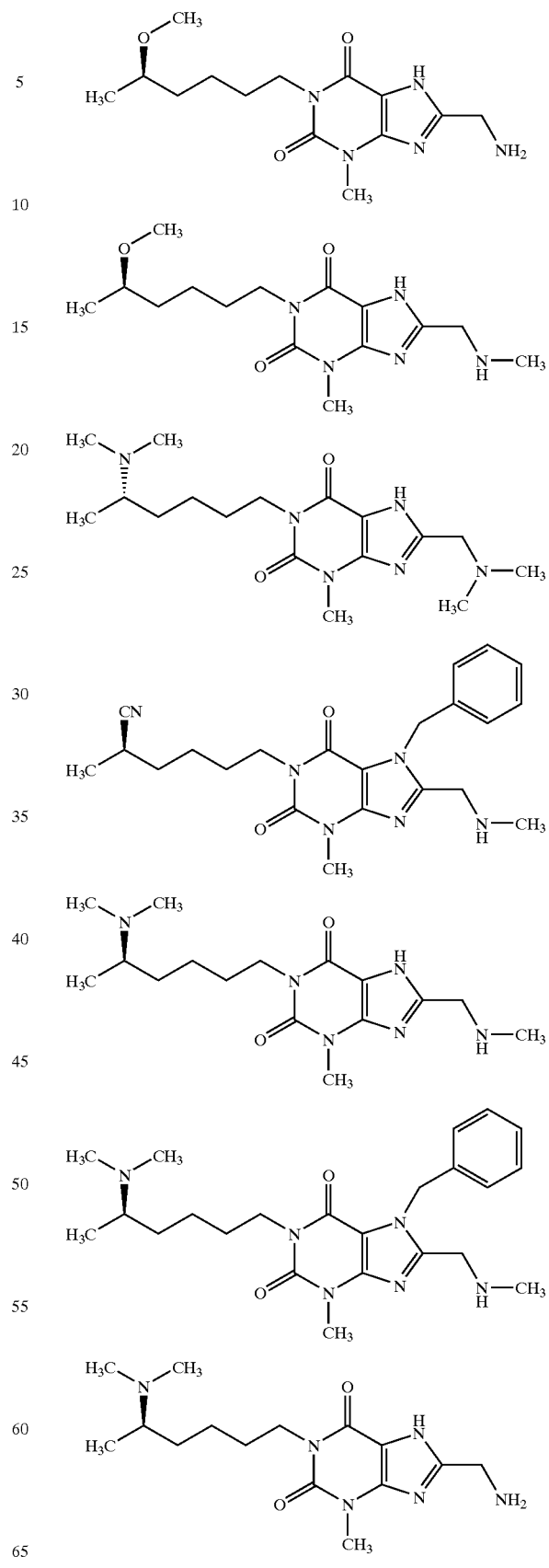

29
-continued

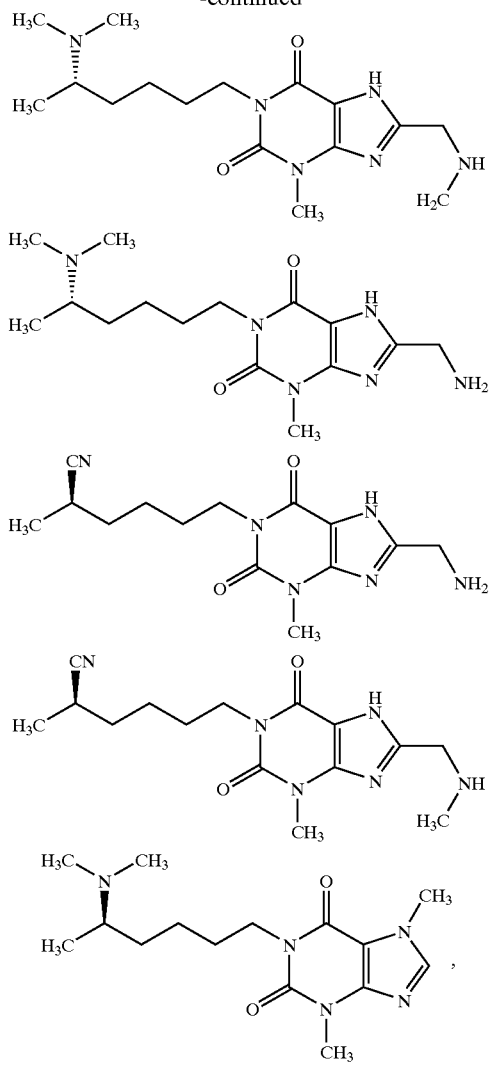

30
-continued

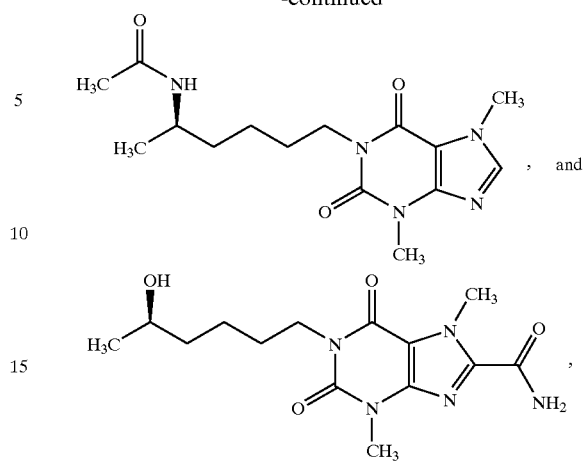

Further representative compounds of the present invention having utility for inhibiting IL-12 signaling in accordance with the present invention are set forth below in Table 1. The compounds in Table 1 have the following general structure of Formula II:

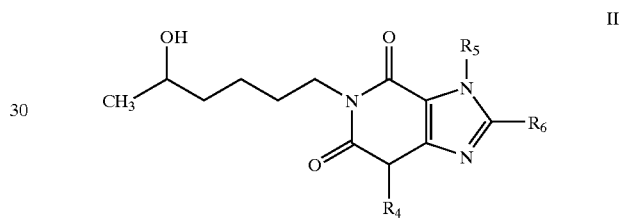

II

It is noted that in Table 1, "Me" represents "—$CH_3$," and "Et" represents "—$CH_2CH_3$." In addition, although the below-exemplified moieties in Table 1 are representative of $R_4$, $R_5$ and $R_6$ in Formula II, it will be understood that the exemplified moieties, without being limited by the above description/definitions, are also representative of $R_2$ and $R_3$ in Formula I.

TABLE 1

| $R_4$ | $R_5$ | $R_6$ |
|---|---|---|
| Me | H | —NH—CH₂-(3-pyridyl) |
| Me | H | —NH—CH₂-(2-pyridyl) |
| Me | H | —NH—CH₂—CH(OH)—CH₃ |

TABLE 1-continued
| | | |
|---|---|---|
| Me | H | 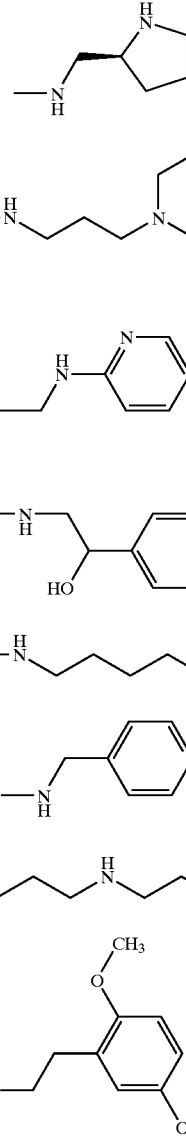 |
| Me | H | 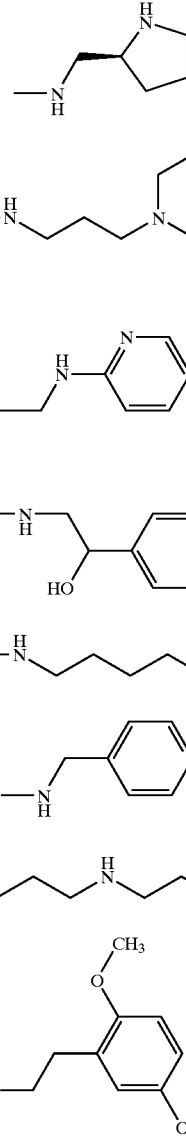 |
| Me | H | 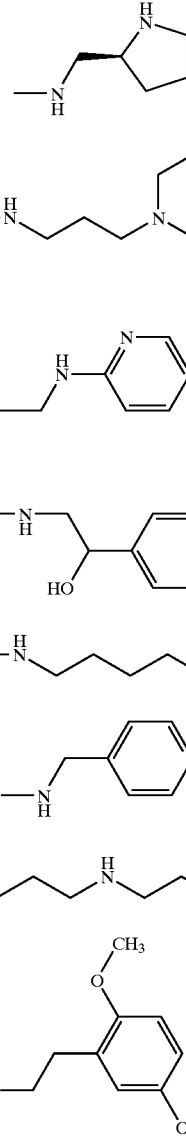 |
| Me | H | 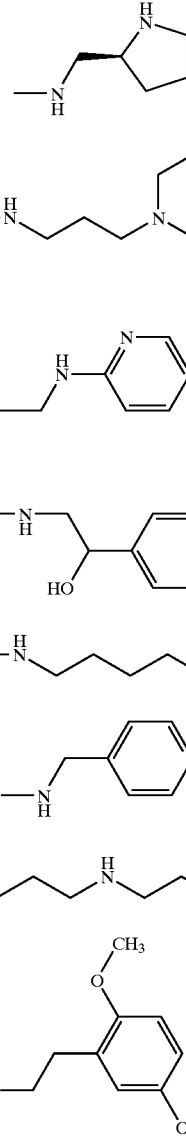 |
| Me | H | 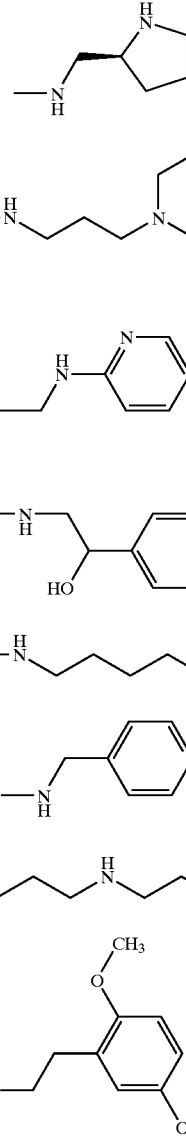 |
| Me | H | 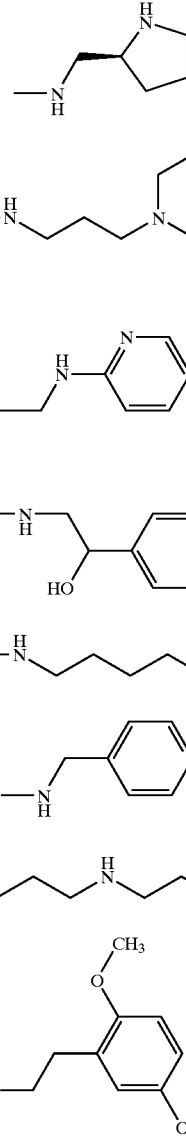 |
| Me | H | 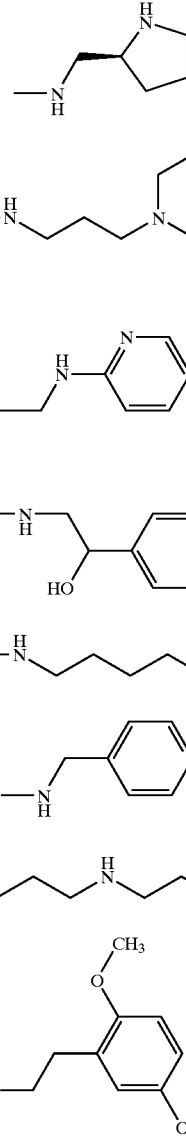 |
| Me | H | 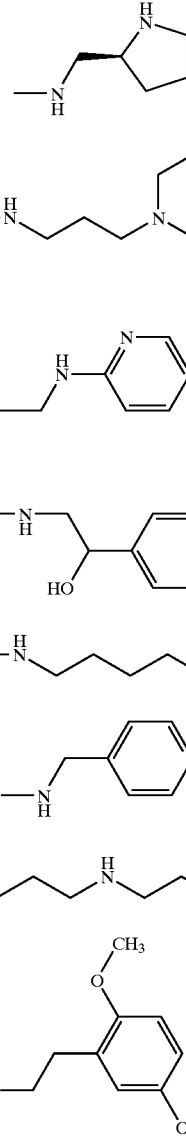 |
| Me | H | 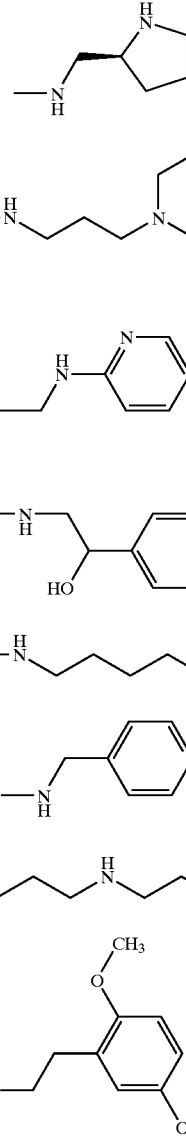 |
| Me | H | 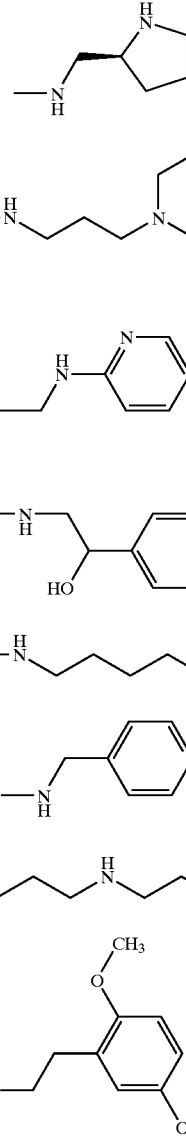 |
| Me | H | 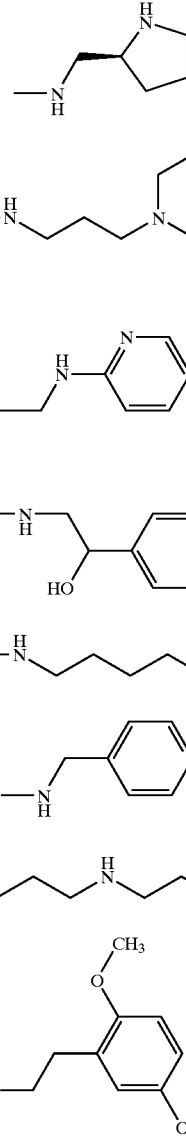 |

TABLE 1-continued
| Me | H | 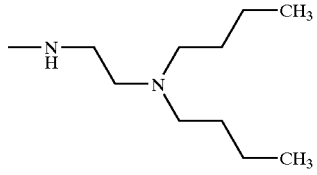 |
| Me | H | 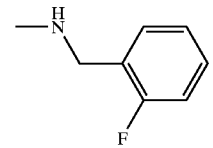 |
| Me | H | 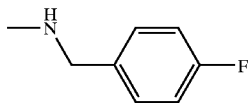 |
| Me | H | 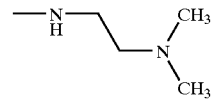 |
| Me | H | 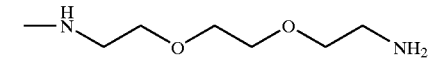 |
| Me | H | 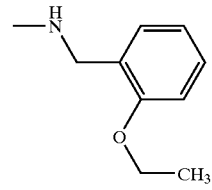 |
| Me | H | 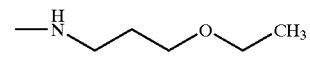 |
| Me | H | 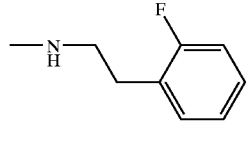 |
| Me | H | 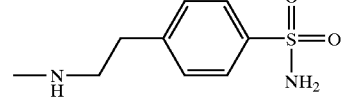 |
| Me | H | 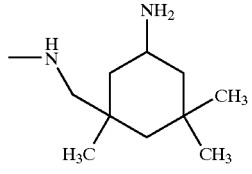 |
| Me | H | 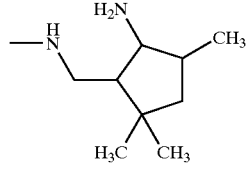 |

TABLE 1-continued

| | | |
|---|---|---|
| Me | H | —NH—CH₂CH₂CH₂—N(piperazine)N—CH₂CH₂CH₂—NH₂ |
| Me | H | —NH—CH₂—[3,5-bis(CF₃)phenyl] |
| Me | H | —NH—CH₂CH₂—[4-Br-phenyl] |
| Me | H | —NH—CH₂—[4-Cl-phenyl] |
| Me | H | —NH—CH₂CH₂—[4-Cl-phenyl] |
| Me | H | —NH—CH₂—CH(CH₃)—phenyl |
| Me | H | —NH—(CH₂)₅—NH—(CH₂)₅—NH₂ |
| Me | H | —NH—CH₂—[3-F-5-CF₃-phenyl] |
| Me | H | —NH—CH₂—[3-F-phenyl] |
| Me | H | —NH—(CH₂)₆—CH₃ |
| Me | H | —NH—CH₂CH₂—[4-F-phenyl] |
| Me | H | —NH—CH₂CH₂—[4-OCH₃-phenyl] |

TABLE 1-continued
| | | |
|---|---|---|
| Me | H | 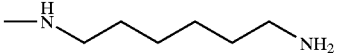 |
| Me | H | 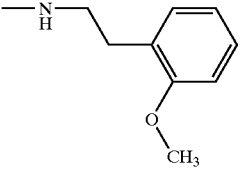 |
| Me | H | 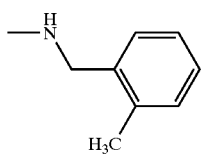 |
| Me | H | 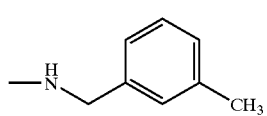 |
| Me | H | 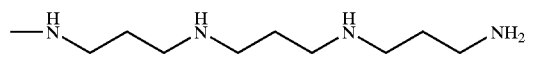 |
| Me | H | 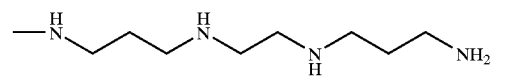 |
| Me | H | 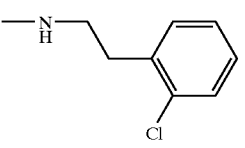 |
| Me | H | 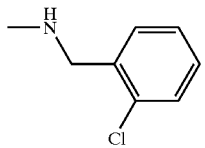 |
| Me | H | 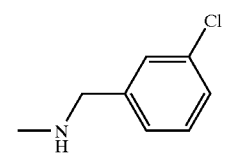 |
| Me | H | 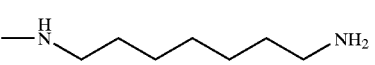 |
| Me | H | 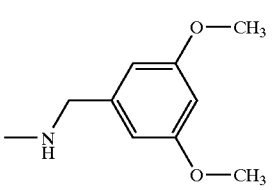 |
| Me | H | |

TABLE 1-continued

| | | |
|---|---|---|
| Me | H | —NH—CH2CH2CH2—NH—cyclohexyl |
| Me | H | —NH—(CH2)9—NH2 |
| Me | H | —NH—CH2—C(CH3)2—NH2 |
| Me | H | —NH—CH2—CH(CH3)—NH2 |
| Me | H | —NH—(CH2)5—NH2 |
| Me | H | —NH—CH2—(4-methylphenyl) |
| Me | H | —NH—(CH2)8—CH3 |
| Me | H | —NH—CH2CH2—NH—CH3 |
| Me | H | —NH—CH2CH2—NH—phenyl |
| Me | H | —NH—CH2CH2CH2—NH—CH2CH2CH3 |
| Me | H | —NH—CH2CH2—NH—CH2CH2CH3 |
| Me | H | —NH—(CH2CH2—NH)5—H |
| Me | H | —NH—CH2CH2—(4-methylphenyl) |
| Me | H | —NH—CH2-(2,6,6-trimethylbicyclo[3.1.1]heptyl) |
| Me | H | —NH—CH2—C≡CH |

TABLE 1-continued

| | | |
|---|---|---|
| Me | H | —NH—CH₂—C₆H₄—CF₃ (4-trifluoromethylbenzyl) |
| Me | H | —NH—(CH₂)₉—CH₃ |
| Me | H | —NH—(CH₂)₈—NH₂ |
| Me | H | —NH—(CH₂)₉—NH₂ |
| Me | H | —NH—CH₂—(2,6-difluorophenyl) |
| Me | H | —NH—CH₂—(2,4-dichlorophenyl) |
| Me | H | —NH—CH₂CH₂—(2,4-dichlorophenyl) |
| Me | H | —NH—CH₂—(2,4-difluorophenyl) |
| Me | H | —NH—CH₂—(2,5-difluorophenyl) |
| Me | H | —NH—CH₂—C₆H₄—OCF₃ (4-trifluoromethoxybenzyl) |
| Me | H | —NH—CH₂CH₂CH₂—O—CH₂CH₂—O—CH₂CH₂—O—CH₂CH₂CH₂—NH₂ |
| Me | H | —NH—CH₂—C(CH₃)₂—CH₂—N(CH₃)₂ |
| Me | H | —NH—CH₂CH₂—NH—CH₂CH₂—NH—CH₂CH₂—NH—CH₂CH₂—NH₂ |

TABLE 1-continued

| | | |
|---|---|---|
| Me | H | ![structure](CH3NH-CH2CH2-NH-CH2CH2-NH-CH2CH2-NH2) |
| Me | H | ![structure](m-xylylenediamine, N-methyl) |
| Me | H | ![structure](3-CF3-benzyl methylamine) |
| Me | H | ![structure](N-methyl tryptamine) |
| Me | H | ![structure](N-methyl tyramine) |
| Me | H | ![structure](3,4-dimethoxybenzyl methylamine) |
| Me | H | ![structure](2-thienylmethyl methylamine) |
| Me | H | amine, N-methyl) |
| Me | H | ![structure](p-xylylenediamine, N-methyl) |
| Me | H | ![structure](3,4,5-trimethoxybenzyl methylamine) |
| Me | H | ![structure](4-phenylbutyl methylamine) |

TABLE 1-continued
| | | |
|---|---|---|
| Me | H | 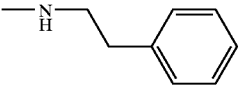 |
| Me | H | 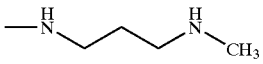 |
| Me | H | 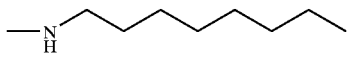 |
| Me | H | 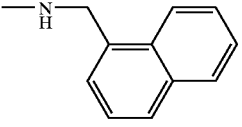 |
| Me | H | 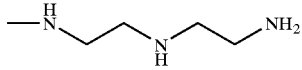 |
| Me | H | 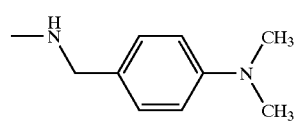 |
| Me | H | 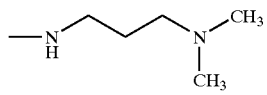 |
| Me | H | 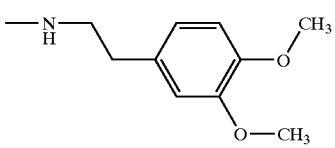 |
| Me | H | 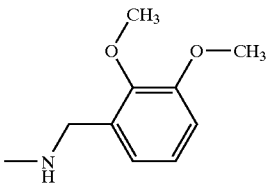 |
| Me | H | 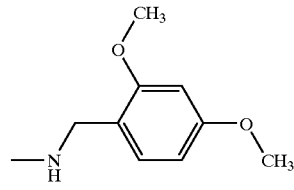 |
| Me | H | 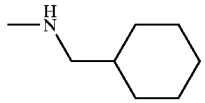 |
| Me | H | 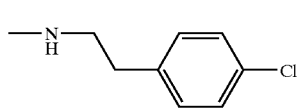 |
| Me | H | 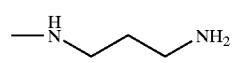 |

TABLE 1-continued

| | | |
|---|---|---|
| Me | H | —NH—CH₂—C(CH₃)₂—CH₂—NH₂ |
| Me | H | —NH—CH₂—CH(OH)—CH₂—NH₂ |
| Me | H | —NH—(CH₂)₃—NH₂ |
| Me | H | —NH—CH₂-(benzo[1,3]dioxol-5-yl) |
| Me | H | —NH—(CH₂)₃-phenyl |
| Me | H | —NH—(CH₂)₂-(thiophen-2-yl) |
| Me | H | —NH—(CH₂)₂-(tetrahydrofuran-2-yl) |
| Me | H | —NH—CH₂-(2-methoxyphenyl) |
| Me | H | —NH—CH₂-(4-methoxyphenyl) |
| Me | H | —NH—CH₂—CH(CH₃)—CH₂—CH₃ |
| Me | H | —NH—(CH₂)₂-(5-methoxy-1H-indol-3-yl) |
| Me | H | —NH—(CH₂)₃—NH—CH(CH₃)₂ |

TABLE 1-continued
| | | |
|---|---|---|
| Me | H | 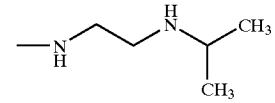 |
| Me | H | 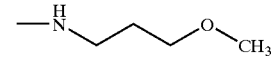 |
| Me | H | 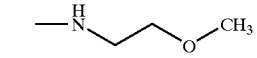 |
| Me | H | 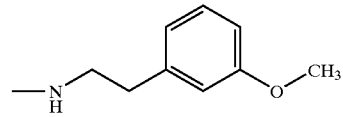 |
| Me | H | 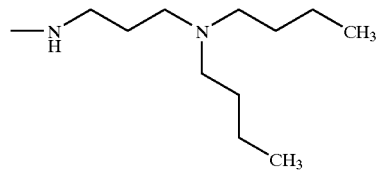 |
| Me | H | 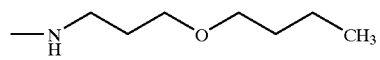 |
| Me | H | 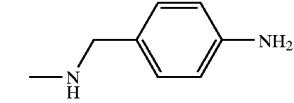 |
| Me | H | 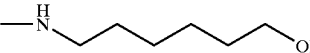 |
| Me | H | 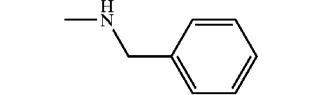 |
| Me | H | 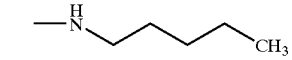 |
| Me | H | 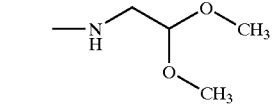 |
| Me | H | 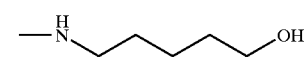 |
| Me | H | 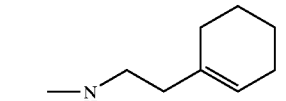 |
| Me | H | 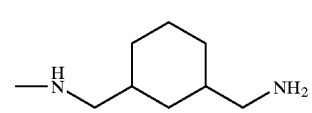 |
| Me | H | 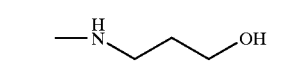 |

TABLE 1-continued
| | | |
|---|---|---|
| Me | H | 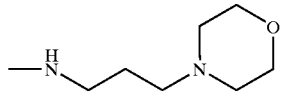 |
| Me | H | 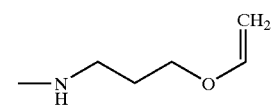 |
| Me | H | 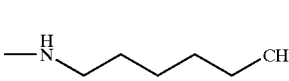 |
| Me | H | 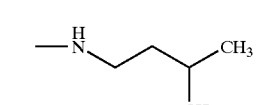 |
| Me | H | 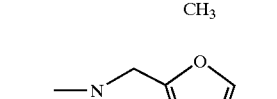 |
| Me | H | 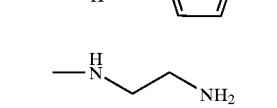 |
| Me | H | 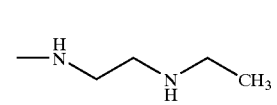 |
| Me | H | 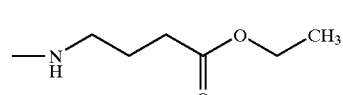 |
| Me | H | 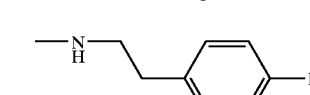 |
| Me | H | 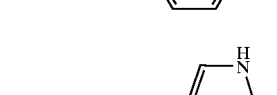 |
| Me | H | 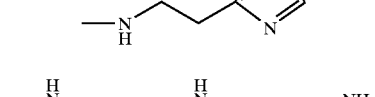 |
| Me | H | 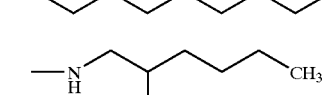 |
| Me | H | 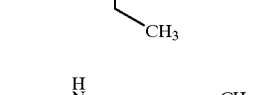 |
| Me | H | 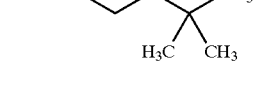 |
| Me | H | 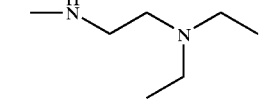 |
| Me | H | 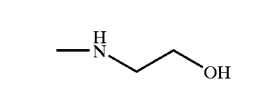 |

TABLE 1-continued

| | | |
|---|---|---|
| Me | H | —NH-CH2CH2CH2-N(Et)2 (methylaminopropyl diethylamino) |
| Me | H | —NH-CH2CH2CH2-N(CH3)-CH2CH2CH2-NH2 |
| Me | H | 2-aminobenzyl methylamine (—NHCH2-C6H4-NH2, ortho) |
| Me | H | —NH-CH2CH2-NH-CH2CH2-OH |
| Me | H | —NH-CH2CH2-(2-pyridyl) |
| Me | H | —NH-CH2CH2-C6H4-NH2 (para) |
| Me | H | —NH-CH2-(4-piperidyl, NH) |
| Me | H | —NH-CH2CH2-(morpholin-4-yl) |
| Me | H | —NH-CH2CH2-(piperidin-1-yl) |
| Me | H | —NH-CH2CH2CH2-(imidazol-1-yl) |
| Me | H | —NH-CH2CH2CH2-(2-oxopyrrolidin-1-yl) |
| Me | H | —NH-CH2CH2-O-CH2CH2-OH |
| Me | H | —NH-CH2CH2-(1-methylpyrrolidin-2-yl) |
| Me | H | —NH-CH2CH2-(piperazin-1-yl, NH) |

TABLE 1-continued
| | | |
|---|---|---|
| Me | H | 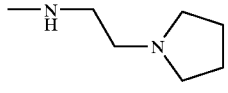 |
| Me | Me | 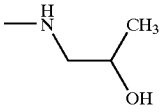 |
| Me | Me | 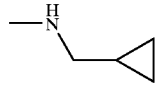 |
| Me | Me | 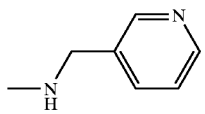 |
| Me | Me | 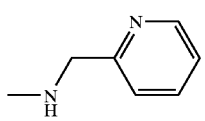 |
| Me | Me | 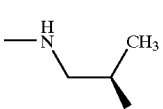 |
| Me | Me | 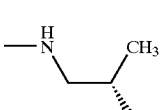 |
| Me | Me | 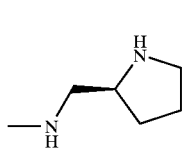 |
| Me | Me | 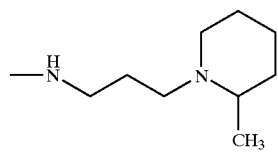 |
| Me | Me | 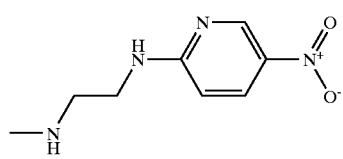 |
| Me | Me | 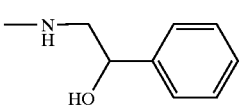 |
| Me | Me | 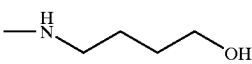 |
| Me | Me | 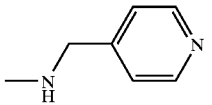 |

TABLE 1-continued

| | | |
|---|---|---|
| Me | Me | —NH–CH₂CH₂CH₂–NH–CH₂CH₂CH₂–NH₂ |
| Me | Me | —NH–CH₂CH₂–(2,5-dimethoxyphenyl) |
| Me | Me | —NH–CH₂–(3,4-dichlorophenyl) |
| Me | Me | —NH–CH₂–(3,4-difluorophenyl) |
| Me | Me | —NH–CH₂CH₂–N(CH₂CH₂CH₂CH₃)₂ |
| Me | Me | —NH–CH₂–(2-fluorophenyl) |
| Me | Me | —NH–CH₂–(4-fluorophenyl) |
| Me | Me | —NH–CH₂CH₂–N(CH₃)₂ |
| Me | Me | —NH–CH₂CH₂–O–CH₂CH₂–O–CH₂CH₂–NH₂ |
| Me | Me | —NH–CH₂–(2-ethoxyphenyl) |
| Me | Me | —NH–CH₂CH₂CH₂–O–CH₂CH₃ |

TABLE 1-continued
| | | |
|---|---|---|
| Me | Me | 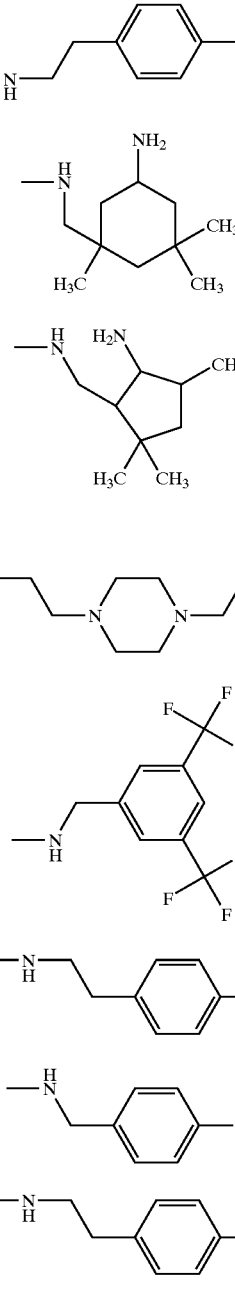 |
| Me | Me | 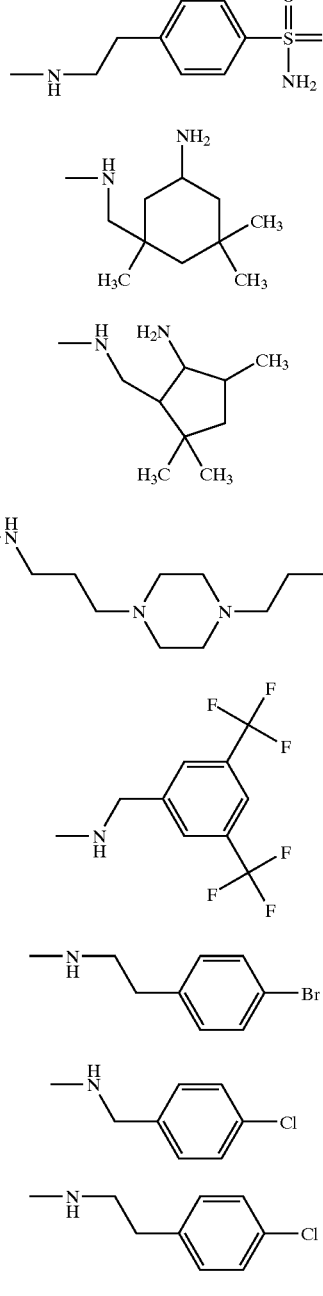 |
| Me | Me | 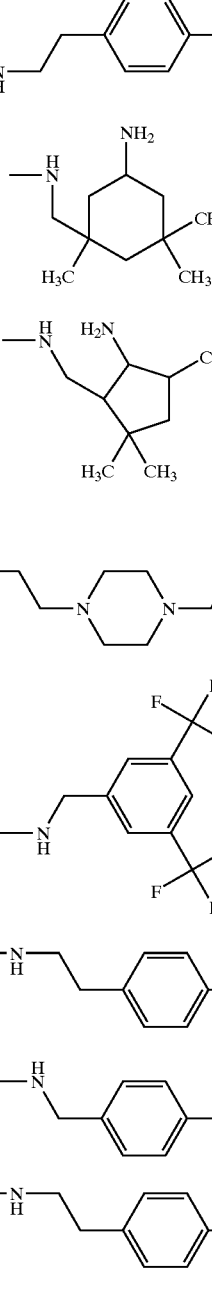 |
| Me | Me | 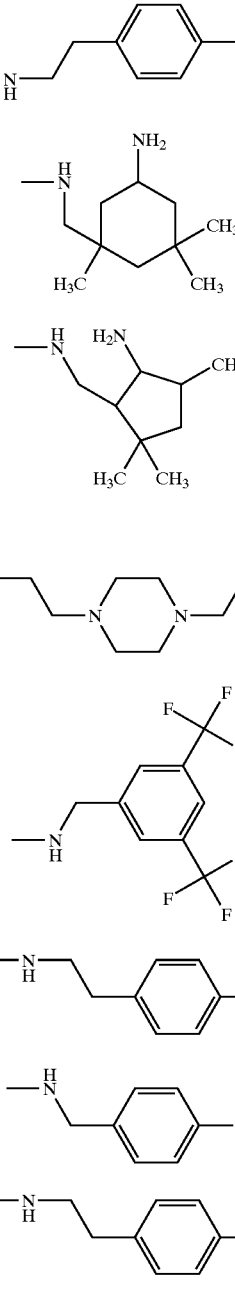 |
| Me | Me | 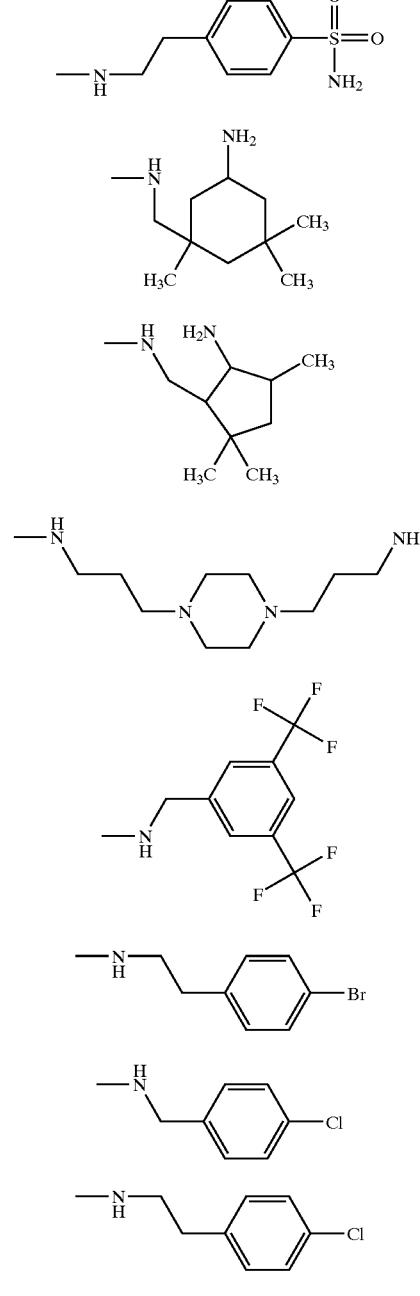 |
| Me | Me | 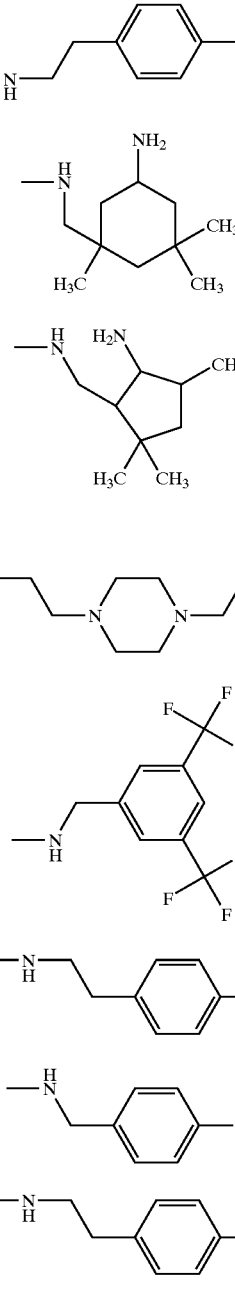 |
| Me | Me | 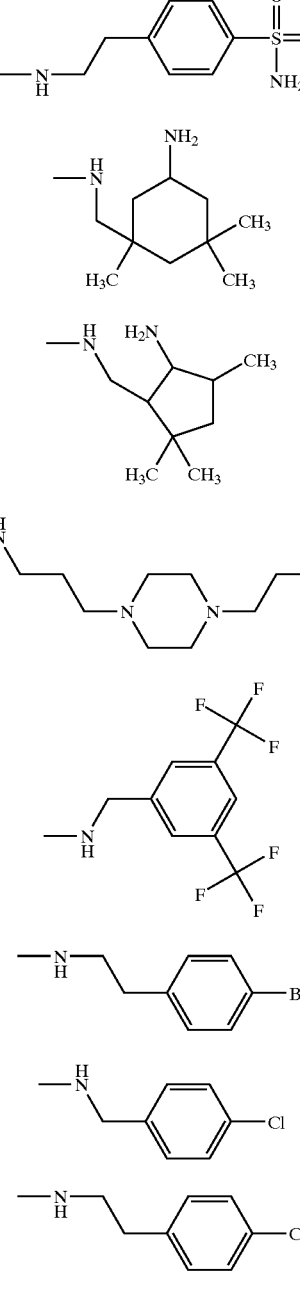 |
| Me | Me | 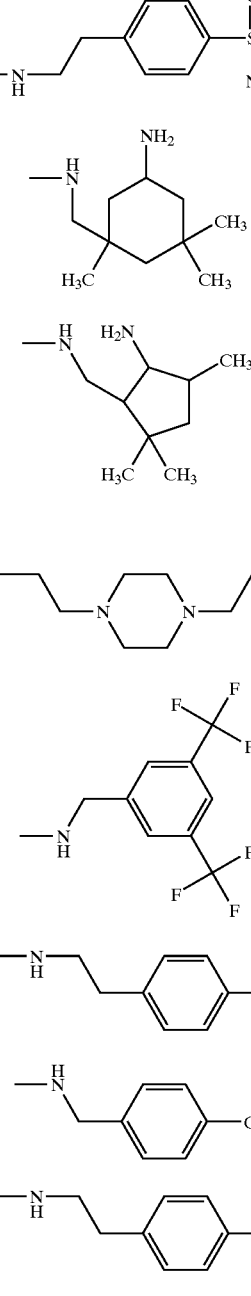 |
| Me | Me | 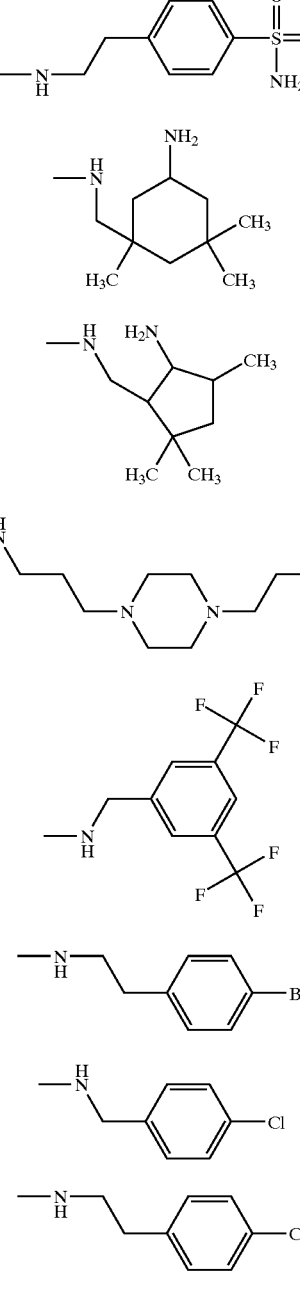 |
| Me | Me | 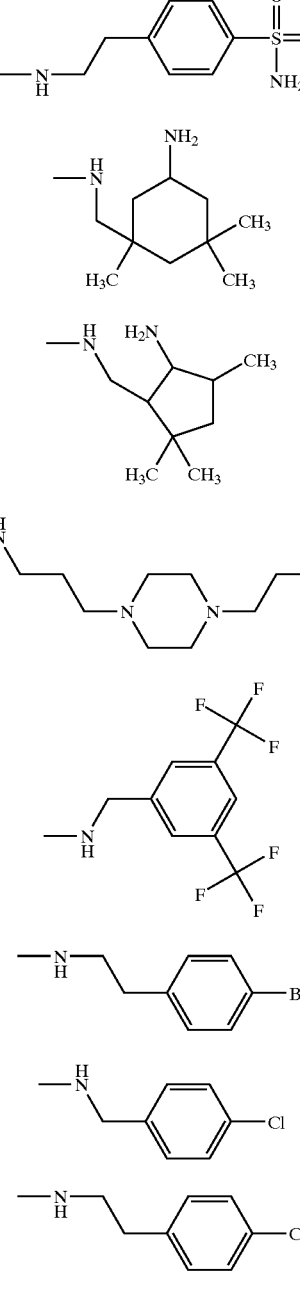 |
| Me | Me | 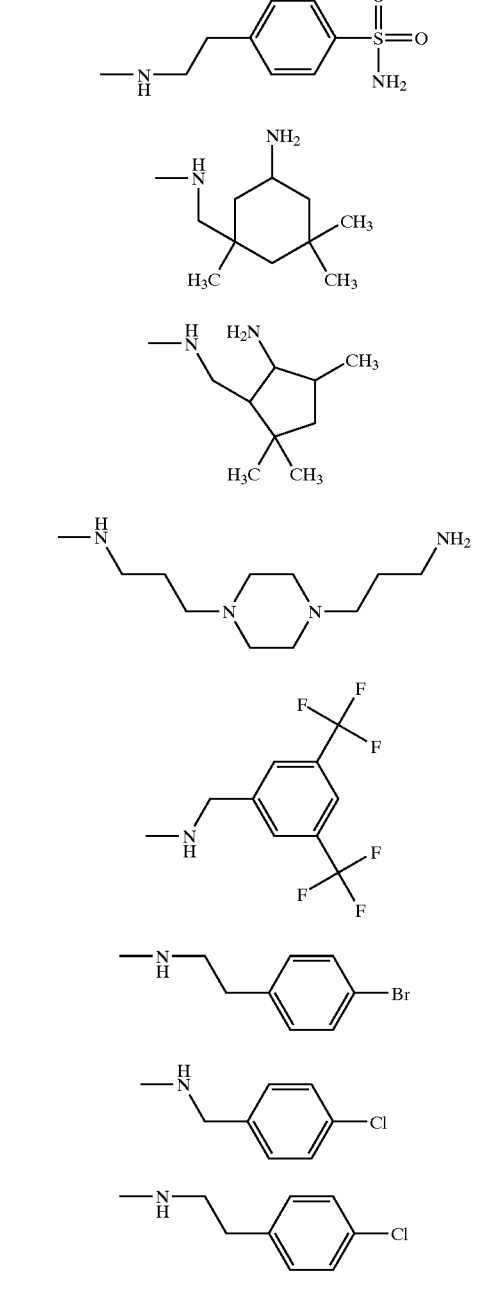 |

TABLE 1-continued

| | | |
|---|---|---|
| Me | Me | 3-fluoro-5-(trifluoromethyl)benzyl(methyl)amine |
| Me | Me | 3-fluorobenzyl(methyl)amine |
| Me | Me | N-methylheptylamine |
| Me | Me | N-methyl-2-(4-fluorophenyl)ethylamine |
| Me | Me | N-methyl-2-(4-methoxyphenyl)ethylamine |
| Me | Me | N-methylgeranylamine |
| Me | Me | N-methyl-1,6-hexanediamine |
| Me | Me | N-methyl-2-(2-methoxyphenyl)ethylamine |
| Me | Me | 2-methylbenzyl(methyl)amine |
| Me | Me | 3-methylbenzyl(methyl)amine |
| Me | Me | N-methyl-N'-(3-aminopropyl)-N''-(3-aminopropyl)propane-1,3-diamine |
| Me | Me | N-methyl-N'-(2-aminoethyl)-N''-(3-aminopropyl)propane-1,3-diamine |
| Me | Me | N-methyl-2-(2-chlorophenyl)ethylamine |

(Note: the right-hand column contains chemical structure drawings; names above are descriptive approximations of the structures shown.)

TABLE 1-continued

| | | |
|---|---|---|
| Me | Me | 2-chlorobenzyl(methyl)amine |
| Me | Me | 3-chlorobenzyl(methyl)amine |
| Me | Me | N-methyl-1,6-hexanediamine |
| Me | Me | 3,5-dimethoxybenzyl(methyl)amine |
| Me | Me | N-cyclohexyl-N'-methyl-1,3-propanediamine |
| Me | Me | N-methyl-1,9-nonanediamine |
| Me | Me | 2-methyl-N¹-methyl-1,2-propanediamine |
| Me | Me | N¹-methyl-1,2-propanediamine |
| Me | Me | N-methyl-1,5-pentanediamine |
| Me | Me | 4-methylbenzyl(methyl)amine |
| Me | Me | N-methylnonylamine |
| Me | Me | N,N'-dimethylethylenediamine |
| Me | Me | N-methyl-N'-phenylethylenediamine |

TABLE 1-continued

| | | |
|---|---|---|
| Me | Me | —NH-CH2CH2CH2-NH-CH2CH3 (N-methyl-N'-propyl-propane-1,3-diamine) |
| Me | Me | —NH-CH2CH2-NH-CH2CH2CH3 |
| Me | Me | —NH-CH2CH2-NH-CH2CH2-NH-CH2CH2-NH-CH2CH2-NH-CH2CH2-NH2 |
| Me | Me | —NH-CH2CH2-C6H4-CH3 (p-tolyl) |
| Me | Me | —NH-CH2-(pinanyl, 6,6-dimethylbicyclo[3.1.1]heptyl) |
| Me | Me | —NH-CH2-C≡CH |
| Me | Me | —NH-CH2-C6H4-CF3 (4-trifluoromethylbenzyl) |
| Me | Me | —NH-(CH2)10-CH3 |
| Me | Me | —NH-(CH2)7-NH2 |
| Me | Me | —NH-(CH2)8-NH2 |
| Me | Me | —NH-CH2-C6H3(2,6-F2) |
| Me | Me | —NH-CH2-C6H3(2,4-Cl2) |
| Me | Me | —NH-CH2CH2-C6H3(2,4-Cl2) |
| Me | Me | —NH-CH2-C6H3(2,4-F2) |

TABLE 1-continued

| | | |
|---|---|---|
| Me | Me | N-methyl-(2,5-difluorobenzyl)amine |
| Me | Me | N-methyl-(4-trifluoromethoxybenzyl)amine |
| Me | Me | 1-(methylamino)-2-(2-(2-(2-aminoethoxy)ethoxy)ethoxy)ethane |
| Me | Me | N,N,N'-trimethyl-2,2-dimethyl-1,3-propanediamine |
| Me | Me | N-methyl-tetraethylenepentamine |
| Me | Me | N-methyl-triethylenetetramine |
| Me | Me | 3-(methylaminomethyl)benzylamine |
| Me | Me | N-methyl-(3-trifluoromethylbenzyl)amine |
| Me | Me | N-methyl-tryptamine |
| Me | Me | N-methyl-tyramine |
| Me | Me | N-methyl-(3,4-dimethoxybenzyl)amine |
| Me | Me | N-methyl-(2-thienylmethyl)amine |

TABLE 1-continued

| | | |
|---|---|---|
| Me | Me | H-N-CH₂CH₂-N(CH₂CH₂NH₂)₂ (tris(2-aminoethyl)amine with one N-methyl) |
| Me | Me | 4-(aminomethyl)-N-methylbenzylamine |
| Me | Me | N-methyl-3,4,5-trimethoxybenzylamine |
| Me | Me | N-methyl-4-phenylbutylamine |
| Me | Me | N-methylphenethylamine |
| Me | Me | N,N'-dimethyl-1,3-propanediamine |
| Me | Me | N-methyloctylamine |
| Me | Me | N-methyl-1-naphthalenemethylamine |
| Me | Me | N-methyl-N'-(2-aminoethyl)ethylenediamine |
| Me | Me | 4-(dimethylamino)-N-methylbenzylamine |
| Me | Me | N,N-dimethyl-N'-methyl-1,3-propanediamine |
| Me | Me | N-methyl-2-(3,4-dimethoxyphenyl)ethylamine |

TABLE 1-continued

| | | |
|---|---|---|
| Me | Me | 2,3-dimethoxybenzyl-NH-Me |
| Me | Me | 2,4-dimethoxybenzyl-NH-Me |
| Me | Me | cyclohexylmethyl-NH-Me |
| Me | Me | 4-chlorophenethyl-NH-Me |
| Me | Me | H-N(Me)-CH₂CH₂CH₂-NH₂ |
| Me | Me | Me-NH-CH₂-C(CH₃)₂-CH₂-NH₂ |
| Me | Me | Me-NH-CH₂-CH(OH)-CH₂-NH₂ |
| Me | Me | Me-NH-(CH₂)₄-NH₂ |
| Me | Me | (1,3-benzodioxol-5-yl)methyl-NH-Me |
| Me | Me | 3-phenylpropyl-NH-Me |
| Me | Me | 2-(thiophen-2-yl)ethyl-NH-Me |
| Me | Me | 2-(tetrahydrofuran-2-yl)ethyl-NH-Me |

TABLE 1-continued
| | | |
|---|---|---|
| Me | Me | 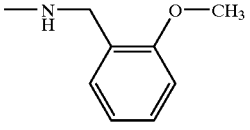 |
| Me | Me | 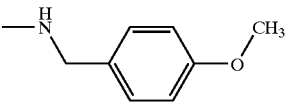 |
| Me | Me | 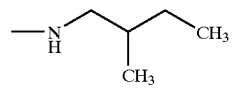 |
| Me | Me | 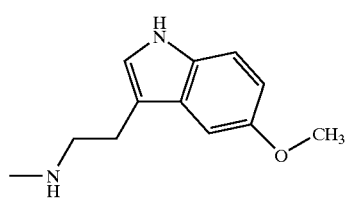 |
| Me | Me | 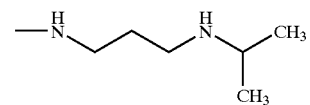 |
| Me | Me | 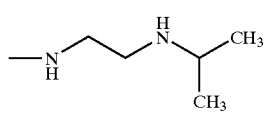 |
| Me | Me | 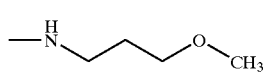 |
| Me | Me | 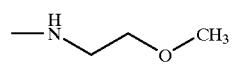 |
| Me | Me | 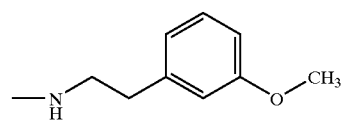 |
| Me | Me | 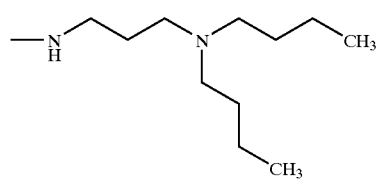 |
| Me | Me | 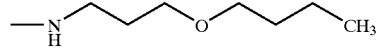 |
| Me | Me | 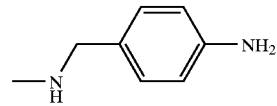 |
| Me | Me | 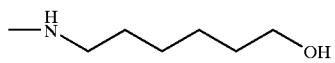 |

TABLE 1-continued

| | | |
|---|---|---|
| Me | Me | PhCH2-NH-Me |
| Me | Me | MeNH-(CH2)4-CH3 |
| Me | Me | MeNH-CH2-CH(OMe)2 |
| Me | Me | MeNH-(CH2)4-OH |
| Me | Me | MeNH-CH2-CH2-(cyclohexenyl) |
| Me | Me | 1,3-bis(aminomethyl)cyclohexane, N-Me |
| Me | Me | MeNH-(CH2)3-OH |
| Me | Me | MeNH-(CH2)3-morpholino |
| Me | Me | MeNH-(CH2)3-O-CH=CH2 |
| Me | Me | MeNH-(CH2)5-CH3 |
| Me | Me | MeNH-CH2-CH(CH3)2 — MeNH-CH2-CH2-CH(CH3)2 |
| Me | Me | MeNH-CH2-(2-furyl) |
| Me | Me | MeNH-CH2-CH2-NH2 |
| Me | Me | MeNH-CH2-CH2-NH-CH2-CH3 |
| Me | Me | MeNH-(CH2)3-C(O)-O-CH2CH3 |
| Me | Me | MeNH-CH2-CH2-(4-F-C6H4) |

TABLE 1-continued

| | | |
|---|---|---|
| Me | Me | -NH-CH2-CH2-(1H-imidazol-4-yl) |
| Me | Me | -NH-(CH2)3-NH-(CH2)3-NH2 |
| Me | Me | -NH-CH2-CH(C2H5)-(CH2)3-CH3 |
| Me | Me | -NH-CH2-CH2-C(CH3)3 |
| Me | Me | -NH-CH2-CH2-N(C2H5)2 |
| Me | Me | -NH-CH2-CH2-OH |
| Me | Me | -NH-(CH2)3-N(C2H5)2 |
| Me | Me | -NH-(CH2)3-N(CH3)-(CH2)3-NH2 |
| Me | Me | -NH-CH2-(2-aminophenyl) |
| Me | Me | -NH-CH2-CH2-NH-CH2-CH2-OH |
| Me | Me | -NH-CH2-CH2-(pyridin-2-yl) |
| Me | Me | -NH-CH2-CH2-(4-aminophenyl) |
| Me | Me | -NH-CH2-(piperidin-4-yl) |
| Me | Me | -NH-CH2-CH2-(morpholin-4-yl) |

TABLE 1-continued
| | | |
|---|---|---|
| Me | Me | 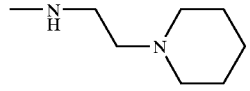 |
| Me | Me | 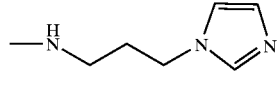 |
| Me | Me | 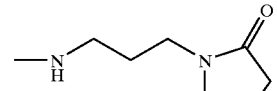 |
| Me | Me | 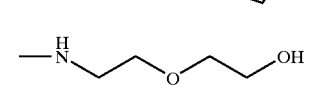 |
| Me | Me | 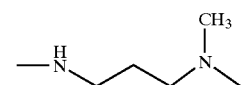 |
| Me | Me |  |
| Me | Me |  |
| Me | Me | 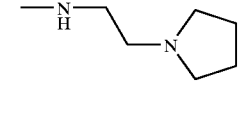 |
| Me | Me | 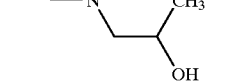 |
| Me | CH$_2$OEt | 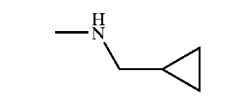 |
| Me | CH$_2$OEt | 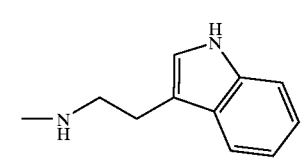 |
| Me | CH$_2$OEt | 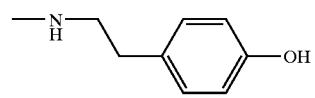 |
| Me | CH$_2$OEt | 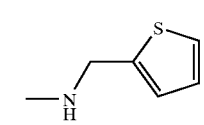 |

TABLE 1-continued

| | | |
|---|---|---|
| Me | CH₂OEt | H-N-CH₂CH₂-N(CH₂CH₂NH₂)₂ (tris(2-aminoethyl)amine with one N-methyl) |
| Me | CH₂OEt | MeHN-CH₂-C₆H₄-CH₂-NH₂ (para) |
| Me | CH₂OEt | MeHN-CH₂-(3,4,5-trimethoxyphenyl) |
| Me | CH₂OEt | MeHN-(CH₂)₃-Ph |
| Me | CH₂OEt | MeHN-CH₂CH₂-Ph |
| Me | CH₂OEt | MeHN-(CH₂)₃-NHMe |
| Me | CH₂OEt | MeHN-(CH₂)₇CH₃ |
| Me | CH₂OEt | MeHN-CH₂-(1-naphthyl) |
| Me | CH₂OEt | MeHN-CH₂CH₂-NH-CH₂CH₂-NH₂ |
| Me | CH₂OEt | MeHN-CH₂-C₆H₄-N(CH₃)₂ (para) |
| Me | CH₂OEt | MeHN-(CH₂)₃-N(CH₃)₂ |
| Me | CH₂OEt | MeHN-CH₂CH₂-(3,4-dimethoxyphenyl) |

TABLE 1-continued

| | | |
|---|---|---|
| Me | CH₂OEt | 2,3-dimethoxybenzyl-NHMe |
| Me | CH₂OEt | 2,4-dimethoxybenzyl-NHMe |
| Me | CH₂OEt | cyclohexylmethyl-NHMe |
| Me | CH₂OEt | 4-chlorophenethyl-NHMe |
| Me | CH₂OEt | MeNH-(CH₂)₃-NH₂ |
| Me | CH₂OEt | MeNH-CH₂-C(CH₃)₂-CH₂-NH₂ |
| Me | CH₂OEt | MeNH-CH₂-CH(OH)-CH₂-NH₂ |
| Me | CH₂OEt | MeNH-(CH₂)₄-NH₂ |
| Me | CH₂OEt | (1,3-benzodioxol-5-yl)methyl-NHMe |
| Me | CH₂OEt | 3-phenylpropyl-NHMe |
| Me | CH₂OEt | 2-(thiophen-2-yl)ethyl-NHMe |
| Me | CH₂OEt | 2-(tetrahydrofuran-2-yl)ethyl-NHMe |

TABLE 1-continued

| | | |
|---|---|---|
| Me | CH₂OEt | —NH—CH₂—(2-methoxyphenyl) |
| Me | CH₂OEt | —NH—CH₂—(4-methoxyphenyl) |
| Me | CH₂OEt | —NH—CH₂—CH(CH₃)—CH₂CH₃ |
| Me | CH₂OEt | —NH—CH₂CH₂—(5-methoxy-1H-indol-3-yl) |
| Me | CH₂OEt | —NH—(CH₂)₃—NH—CH(CH₃)₂ |
| Me | CH₂OEt | —NH—(CH₂)₂—NH—CH(CH₃)₂ |
| Me | CH₂OEt | —NH—(CH₂)₃—OCH₃ |
| Me | CH₂OEt | —NH—(CH₂)₂—OCH₃ |
| Me | CH₂OEt | —NH—CH₂CH₂—(3-methoxyphenyl) |
| Me | CH₂OEt | —NH—(CH₂)₃—N(CH₂CH₂CH₂CH₃)₂ |
| Me | CH₂OEt | —NH—(CH₂)₃—O—(CH₂)₃CH₃ |
| Me | CH₂OEt | —NH—CH₂—(4-aminophenyl) |
| Me | CH₂OEt | —NH—(CH₂)₅—OH |

TABLE 1-continued
| | | |
|---|---|---|
| Me | CH₂OEt | 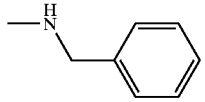 |
| Me | CH₂OEt | 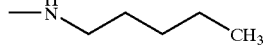 |
| Me | CH₂OEt | 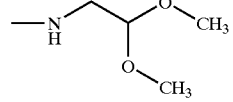 |
| Me | CH₂OEt | 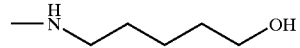 |
| Me | CH₂OEt | 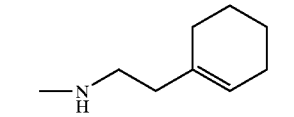 |
| Me | CH₂OEt | 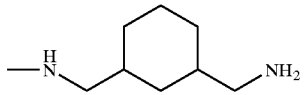 |
| Me | CH₂OEt | 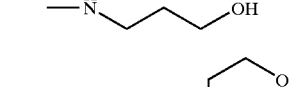 |
| Me | CH₂OEt | 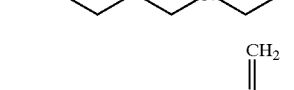 |
| Me | CH₂OEt | 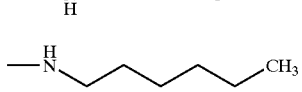 |
| Me | CH₂OEt | 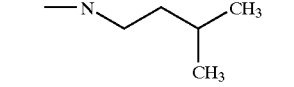 |
| Me | CH₂OEt | 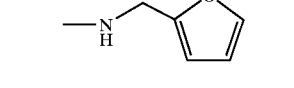 |
| Me | CH₂OEt | 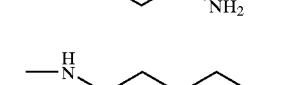 |
| Me | CH₂OEt | 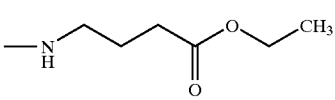 |
| Me | CH₂OEt | 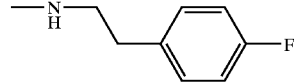 |
| Me | CH₂OEt | |
| Me | CH₂OEt | |

TABLE 1-continued
| | | |
|---|---|---|
| Me | CH$_2$OEt | 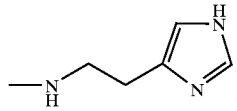 |
| Me | CH$_2$OEt | 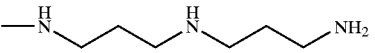 |
| Me | CH$_2$OEt | 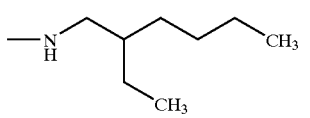 |
| Me | CH$_2$OEt | 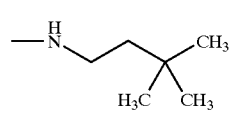 |
| Me | CH$_2$OEt | 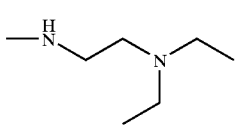 |
| Me | CH$_2$OEt | 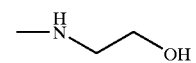 |
| Me | CH$_2$OEt | 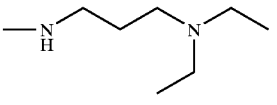 |
| Me | CH$_2$OEt | 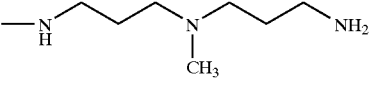 |
| Me | CH$_2$OEt | 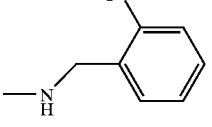 |
| Me | CH$_2$OEt | 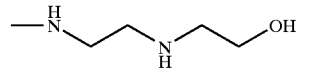 |
| Me | CH$_2$OEt | 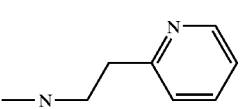 |
| Me | CH$_2$OEt | 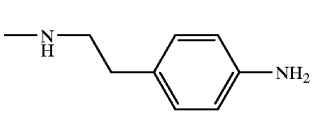 |
| Me | CH$_2$OEt | 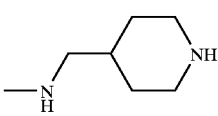 |
| Me | CH$_2$OEt | 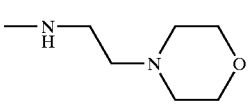 |

TABLE 1-continued

| | | |
|---|---|---|
| Me | CH₂OEt | —NH—CH₂CH₂—N(piperidine) |
| Me | CH₂OEt | —NH—(CH₂)₃—N(imidazole) |
| Me | CH₂OEt | —NH—(CH₂)₃—N(2-pyrrolidinone) |
| Me | CH₂OEt | —NH—CH₂CH₂—O—CH₂CH₂—OH |
| Me | CH₂OEt | —NH—CH₂CH₂—(1-methylpyrrolidin-2-yl) |
| Me | CH₂OEt | —NH—CH₂CH₂—N(piperazine)NH |
| Me | CH₂OEt | —NH—CH₂CH₂—N(pyrrolidine) |
| Me | CH₂OEt | —NH—CH₂—CH(OH)—CH₃ |
| Me | CH₂OEt | —NH—CH₂—cyclopropyl |
| Me | CH₂OEt | —NH—CH₂—(pyridin-3-yl) |
| Me | CH₂OEt | —NH—CH₂—(pyridin-2-yl) |
| Me | CH₂OEt | —NH—CH₂—(R)—CH(OH)—CH₃ |
| Me | CH₂OEt | —NH—CH₂—(S)—CH(OH)—CH₃ |

TABLE 1-continued

| | | |
|---|---|---|
| Me | CH₂OEt | ![structure: (S)-N-methyl-pyrrolidin-2-ylmethylamine] |
| Me | CH₂OEt | ![structure: N-methyl-3-(2-methylpiperidin-1-yl)propylamine] |
| Me | CH₂OEt | ![structure: N-methyl-N'-(5-nitropyridin-2-yl)ethylenediamine] |
| Me | CH₂OEt | ![structure: 2-(methylamino)-1-phenylethanol] |
| Me | CH₂OEt | ![structure: 4-(methylamino)butan-1-ol] |
| Me | CH₂OEt | ![structure: N-methyl-(pyridin-4-yl)methylamine] |
| Me | CH₂OEt | ![structure: N-methyl-N'-(3-aminopropyl)-1,3-propanediamine] |
| Me | CH₂OEt | ![structure: 2-(2,5-dimethoxyphenyl)-N-methylethylamine] |
| Me | CH₂OEt | ![structure: N-methyl-(3,4-dichlorobenzyl)amine] |
| Me | CH₂OEt | ![structure: N-methyl-(3,4-difluorobenzyl)amine] |
| Me | CH₂OEt | ![structure: N-methyl-N',N'-dibutylethylenediamine] |

TABLE 1-continued
| | | |
|---|---|---|
| Me | CH₂OEt | 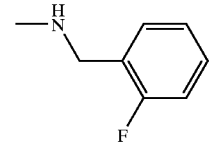 |
| Me | CH₂OEt | 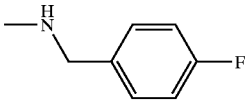 |
| Me | CH₂OEt | 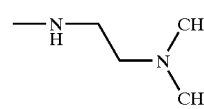 |
| Me | CH₂OEt | 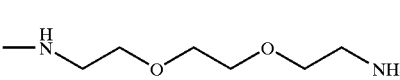 |
| Me | CH₂OEt | 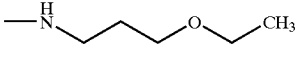 |
| Me | CH₂OEt | 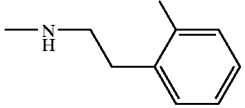 |
| Me | CH₂OEt | 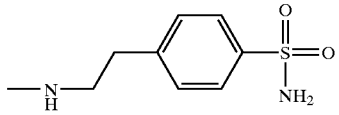 |
| Me | CH₂OEt | 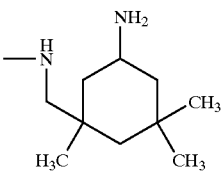 |
| Me | CH₂OEt | 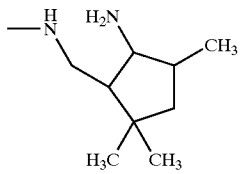 |
| Me | CH₂OEt | 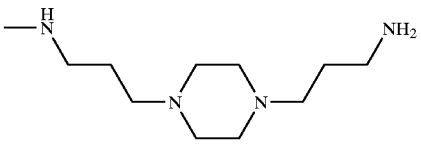 |
| Me | CH₂OEt |  |

TABLE 1-continued
| | | |
|---|---|---|
| Me | CH$_2$OEt | 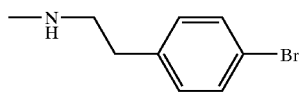 |
| Me | CH$_2$OEt | 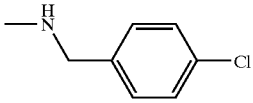 |
| Me | CH$_2$OEt | 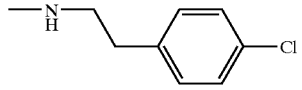 |
| Me | CH$_2$OEt | 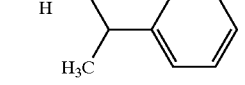 |
| Me | CH$_2$OEt | 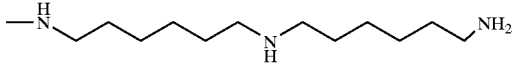 |
| Me | CH$_2$OEt | 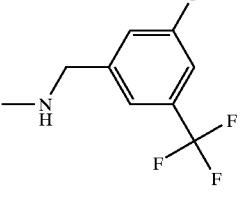 |
| Me | CH$_2$OEt | 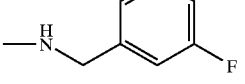 |
| Me | CH$_2$OEt | 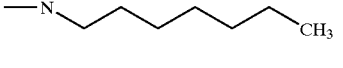 |
| Me | CH$_2$OEt | 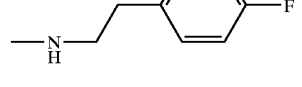 |
| Me | CH$_2$OEt | 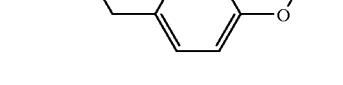 |
| Me | CH$_2$OEt | 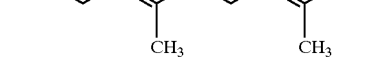 |

TABLE 1-continued
| | | |
|---|---|---|
| Me | CH₂OEt | 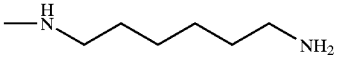 |
| Me | CH₂OEt | 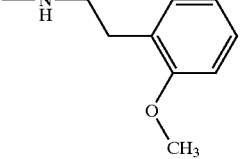 |
| Me | CH₂OEt | 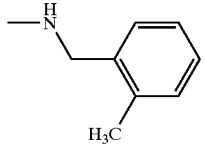 |
| Me | CH₂OEt | 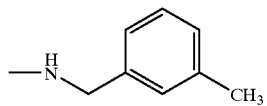 |
| Me | CH₂OEt | 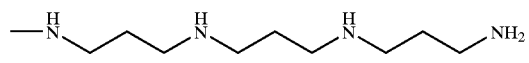 |
| Me | CH₂OEt | 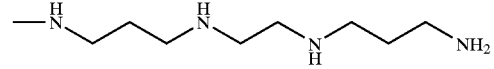 |
| Me | CH₂OEt | 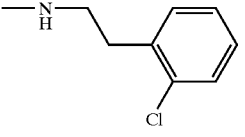 |
| Me | CH₂OEt | 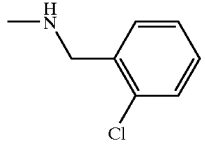 |
| Me | CH₂OEt | 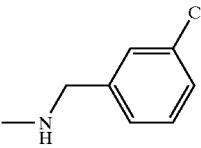 |
| Me | CH₂OEt | 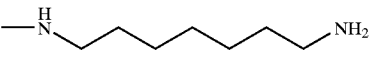 |
| Me | CH₂OEt | 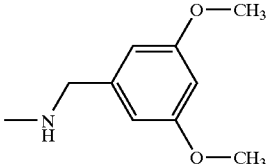 |
| Me | CH₂OEt | 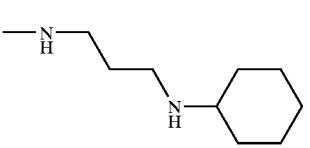 |

TABLE 1-continued
| | | |
|---|---|---|
| Me | CH$_2$OEt | 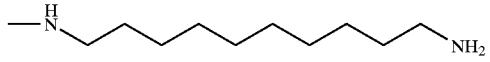 |
| Me | CH$_2$OEt | 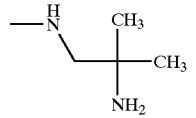 |
| Me | CH$_2$OEt | 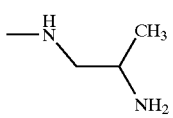 |
| Me | CH$_2$OEt | 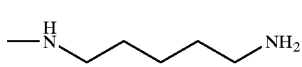 |
| Me | CH$_2$OEt | 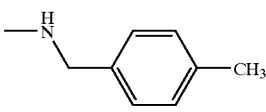 |
| Me | CH$_2$OEt | 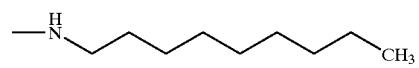 |
| Me | CH$_2$OEt | 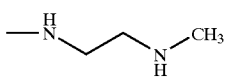 |
| Me | CH$_2$OEt | 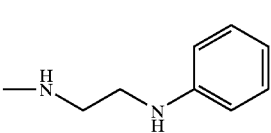 |
| Me | CH$_2$OEt | 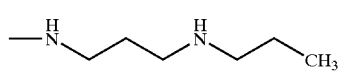 |
| Me | CH$_2$OEt | 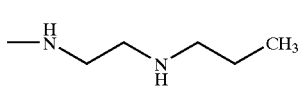 |
| Me | CH$_2$OEt | 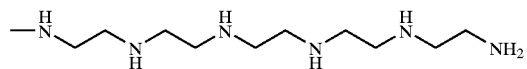 |
| Me | CH$_2$OEt | 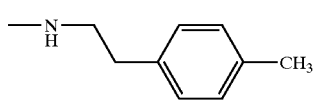 |
| Me | CH$_2$OEt | 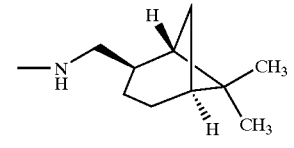 |
| Me | CH$_2$OEt | 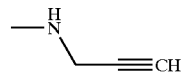 |
| Me | CH$_2$OEt | 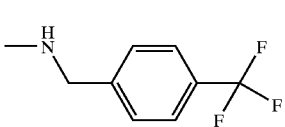 |

TABLE 1-continued
| | | |
|---|---|---|
| Me | CH₂OEt | 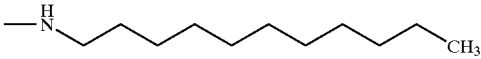 |
| Me | CH₂OEt | 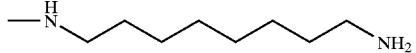 |
| Me | CH₂OEt | 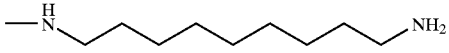 |
| Me | CH₂OEt | 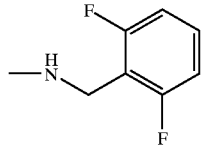 |
| Me | CH₂OEt | 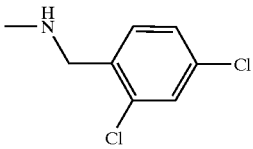 |
| Me | CH₂OEt | 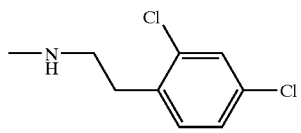 |
| Me | CH₂OEt | 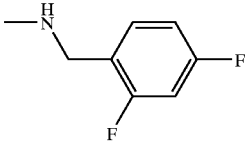 |
| Me | CH₂OEt | 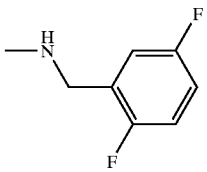 |
| Me | CH₂OEt | 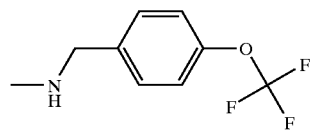 |
| Me | CH₂OEt | 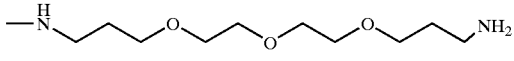 |
| Me | CH₂OEt | 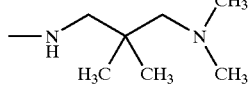 |
| Me | CH₂OEt | 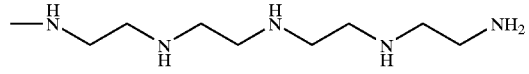 |
| Me | CH₂OEt | 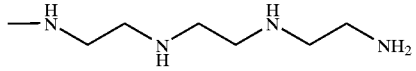 |

TABLE 1-continued

| | | |
|---|---|---|
| Me | CH₂OEt | —NH—CH₂—(3-aminomethylphenyl)—NH₂ (N-methyl, 3-(aminomethyl)benzyl) |
| Me | CH₂OEt | —NH—CH₂—(3-trifluoromethylphenyl) (N-methyl, 3-(trifluoromethyl)benzyl) |

| R₄ | R₅ | R₆ |
|---|---|---|
| (S)-1-bromo-2-methylbutyl (CH₂Br with CH₃ stereocenter, ethyl) | Me | H |
| N-propyl aziridine | Me | H |
| tridecyl (long alkyl chain -CH₃) | Me | H |
| ω-bromo long alkyl chain (-CH₂Br) | Me | H |
| 2-(pentafluorophenyl)ethyl | Me | H |
| 2-(thiophen-2-yl)propyl | Me | H |
| 2-(thiophen-3-yl)propyl | Me | H |
| 3-(2-fluorophenyl)propyl | Me | H |
| 4-(pyridin-2-yl)butyl | Me | H |
| 2-(thiophen-2-yl)ethyl | Me | H |
| 3-(3,4-dimethoxyphenyl)propyl | Me | H |

TABLE 1-continued

| Structure | | |
|---|---|---|
| 3-(trifluoromethyl)phenylpropyl | Me | H |
| 4-bromobutyl | Me | H |
| 3-furanylethyl | Me | H |
| butyl trimethylsilyl | Me | H |
| pent-4-enyl | Me | H |
| 1-chloro-2,2-dimethylbutyl | Me | H |
| 3-chlorophenylpropyl | Me | H |
| N,N-diethylbutylamine | Me | H |
| N-ethyl-N-methylbutylamine | Me | H |
| 3-fluorophenylpropyl | Me | H |
| hept-3-ynyl | Me | H |
| pentanenitrile | Me | H |
| 3-methoxyphenylpropyl | Me | H |
| 3-methylhexyl | Me | H |
| but-1-ynyl trimethylsilyl | Me | H |

TABLE 1-continued
| | | |
|---|---|---|
| 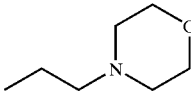 | Me | H |
| 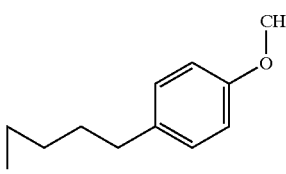 | Me | H |
| 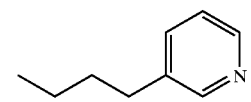 | Me | H |
|  | Me | H |
|  | Me | H |
| 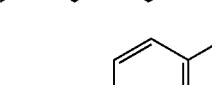 | Me | H |
| 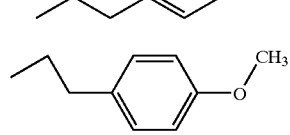 | Me | H |
| 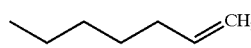 | Me | H |
| 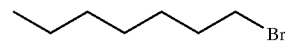 | Me | H |
| 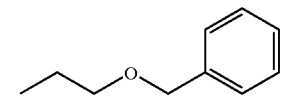 | Me | H |
| 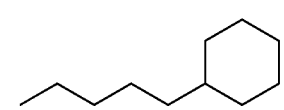 | Me | H |
| 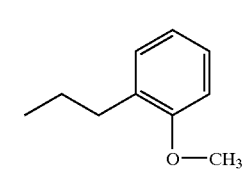 | Me | H |
| 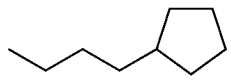 | Me | H |
|  | Me | H |

TABLE 1-continued
| | | |
|---|---|---|
| 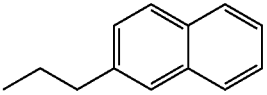 | Me | H |
| 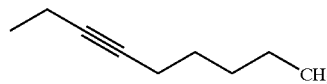 | Me | H |
| 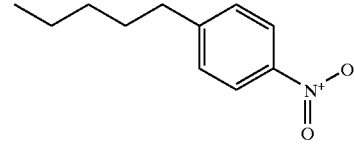 | Me | H |
| 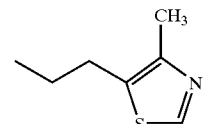 | Me | H |
| 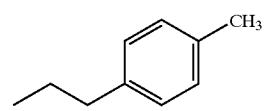 | Me | H |
| 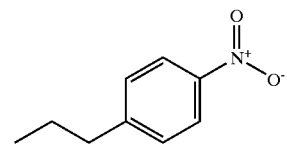 | Me | H |
|  | Me | H |
| 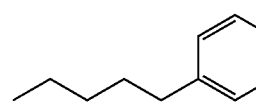 | Me | H |
| 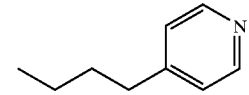 | Me | H |
| 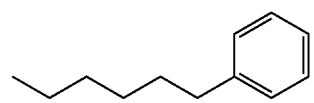 | Me | H |
| 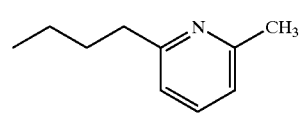 | Me | H |
| 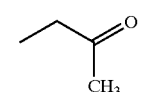 | Me | H |
| 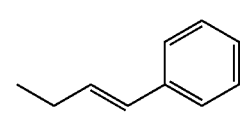 | Me | H |

TABLE 1-continued
| | | |
|---|---|---|
| 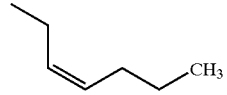 | Me | H |
| 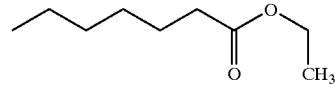 | Me | H |
| 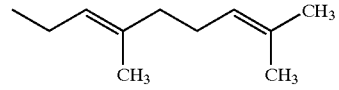 | Me | H |
| 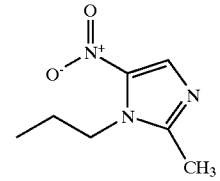 | Me | H |
| 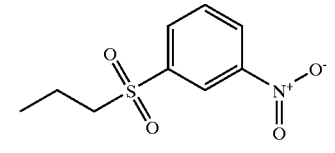 | Me | H |
|  | Me | H |
| 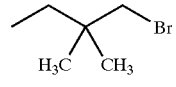 | Me | H |
| 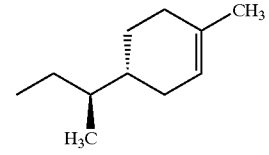 | Me | H |
| 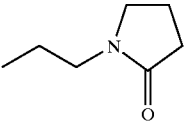 | Me | H |
| 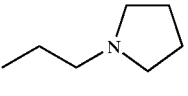 | Me | H |
| 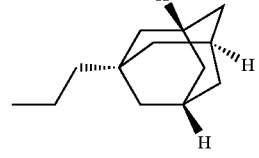 | Me | H |
| 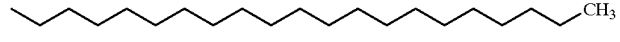 | Me | H |

TABLE 1-continued
| | | |
|---|---|---|
| 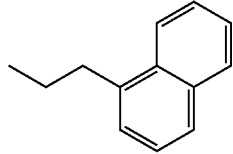 | Me | H |
| 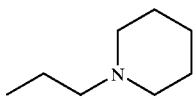 | Me | H |
| 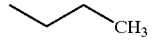 | Me | H |
| 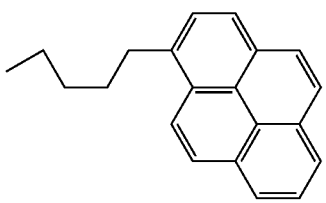 | Me | H |
| 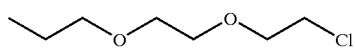 | Me | H |
| 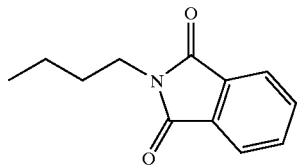 | Me | H |
| 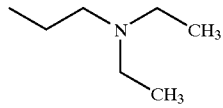 | Me | H |
| 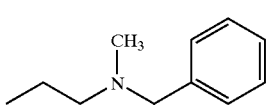 | Me | H |
|  | Me | H |
| 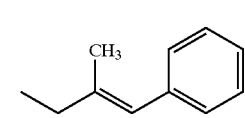 | Me | H |
|  | Me | H |
| 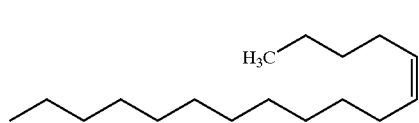 | Me | H |
| 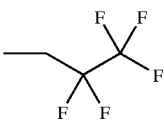 | Me | H |

TABLE 1-continued
| Structure | R | R' |
|---|---|---|
| 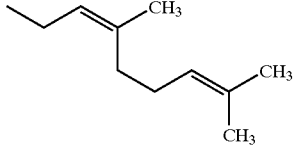 | Me | H |
| 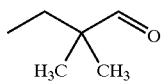 | Me | H |
| 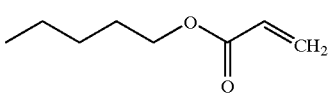 | Me | H |
| 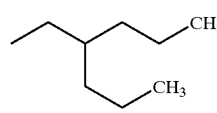 | Me | H |
| 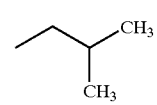 | Me | H |
| 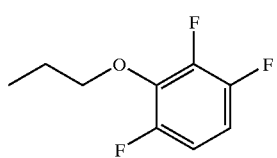 | Me | H |
| 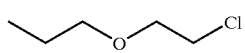 | Me | H |
| 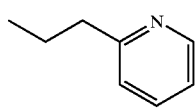 | Me | H |
| 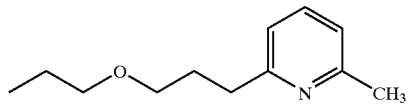 | Me | H |
| 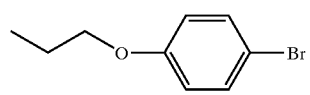 | Me | H |
| 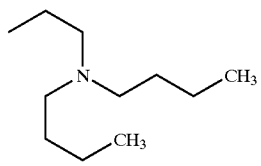 | Me | H |
| 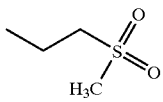 | Me | H |
| 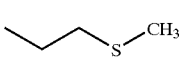 | Me | H |

TABLE 1-continued

| Structure | | |
|---|---|---|
| N-propyl-N-ethyl-3-methylaniline | Me | H |
| propyl phenyl sulfone | Me | H |
| propyl phenyl sulfide | Me | H |
| propyltrimethylsilane | Me | H |
| 1,1,1-trifluorobutane | Me | H |
| 3-methyl-2-pentanone | Me | H |
| 1-propyl-3-nitrobenzene | Me | H |
| 1-butoxy-3-methoxypropane | Me | H |
| cis-4-decene | Me | H |
| 4-methyl-6-(2,2-dimethylpropyl)nonane (branched alkane) | Me | H |
| butylbenzene | Me | H |
| long branched alkene | Me | H |
| branched alkene | Me | H |

TABLE 1-continued

| Structure | | |
|---|---|---|
| methyl 2,2-dimethylbutanoate | Me | H |
| 2-methyl-2-pentene | Me | H |
| 2-methyl-1-pentene | Me | H |
| 3-propyltoluene | Me | H |
| 2-heptyne | Me | H |
| 3,3,4,4,5,5,5-heptafluoropentane (ethyl perfluoropropyl) | Me | H |
| 1H-perfluorohexane derivative | Me | H |
| 3,3,4,4-tetrafluorobutane | Me | H |
| 1,1-diphenylpropane | Me | H |
| 3,5,5-trimethylheptane | Me | H |
| diene with methyl branches | Me | H |
| 1-chloropropane | Me | H |

TABLE 1-continued

| Structure | R1 | R2 |
|---|---|---|
| 2-chlorophenylpropyl | Me | H |
| 2,2-dimethylbutylbenzene | Me | H |
| 3-fluoropropyl | Me | H |
| propyl methacrylate | Me | H |
| (1-methylbutyl)benzene | Me | H |
| propyl-O-CH2CH2-O-butyl | Me | H |
| 1-isopropyl-2,3,4,5,6-pentafluorobenzene | Me | H |
| 2-isopropyl-1-methoxybenzene | Me | H |
| (1-trifluoromethylethyl)benzene | Me | H |
| (pent-3-yn-2-yl)benzene | Me | H |
| 1-(1-methylethyl)naphthalene | Me | H |

TABLE 1-continued
| | | |
|---|---|---|
| 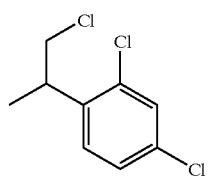 | Me | H |
| 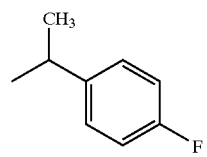 | Me | H |
| 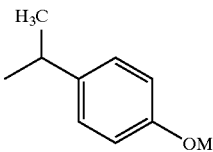 | Me | H |
| 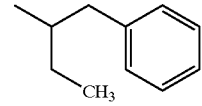 | Me | H |
| 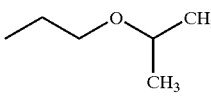 | Me | H |
| 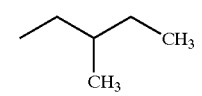 | Me | H |
| 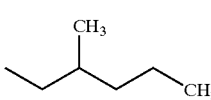 | Me | H |
| 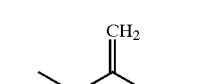 | Me | H |
| 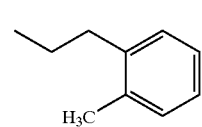 | Me | H |
| 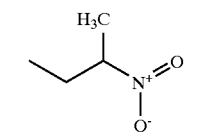 | Me | H |
| 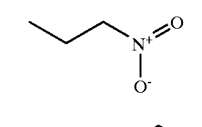 | Me | H |
| 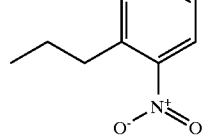 | Me | H |

TABLE 1-continued
| | | |
|---|---|---|
| 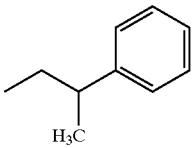 | Me | H |
| 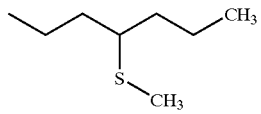 | Me | H |
| 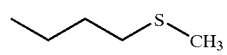 | Me | H |
| 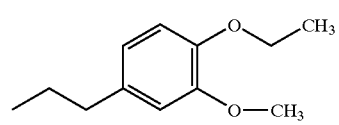 | Me | H |
| 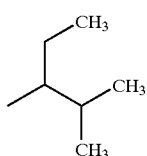 | Me | H |
| 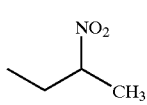 | Me | H |
| 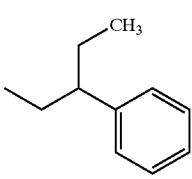 | Me | H |
| 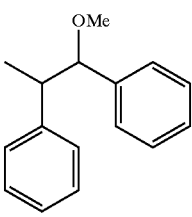 | Me | H |
| 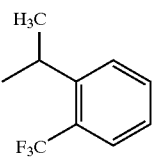 | Me | H |
| 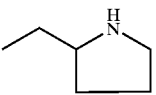 | Me | H |
| 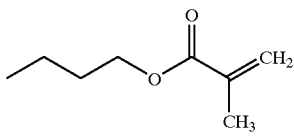 | Me | H |

TABLE 1-continued
| | | Me | H |
|---|---|---|---|
| | 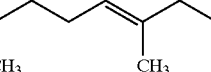 | Me | H |
| |  | Me | H |
| | 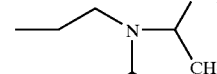 | Me | H |
| | 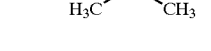 | Me | H |
| R₄ | R₅ | | R₆ |
| Me |  | | H |
| Me | 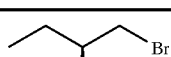 | | H |
| Me |  | | H |
| Me | 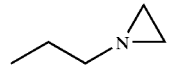 | | H |
| Me | 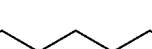 | | H |
| Me | 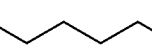 | | H |
| Me |  | | H |
| Me | 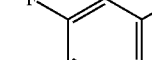 | | H |
| Me | 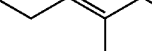 | | H |
| Me |  | | H |

TABLE 1-continued

| | | |
|---|---|---|
| Me | 4-propyl-1,2-dimethoxybenzene | H |
| Me | 1-propyl-3-(trifluoromethyl)benzene | H |
| Me | 1-bromobutane | H |
| Me | 3-ethylfuran | H |
| Me | butyltrimethylsilane | H |
| Me | 1-pentene | H |
| Me | 1-chloro-2,2-dimethylbutane | H |
| Me | 1-propyl-3-chlorobenzene | H |
| Me | N,N-diethylbutylamine | H |
| Me | N-ethyl-N-methylbutylamine | H |
| Me | 1-propyl-3-fluorobenzene | H |
| Me | 3-heptyne | H |
| Me | butanenitrile | H |
| Me | 1-propyl-3-methoxybenzene | H |
| Me | 3-methylhexane | H |

TABLE 1-continued
| | | |
|---|---|---|
| Me | 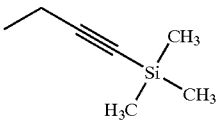 | H |
| Me | 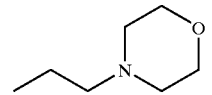 | H |
| Me | 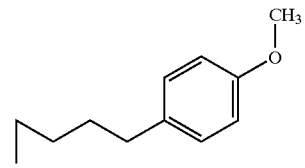 | H |
| Me | 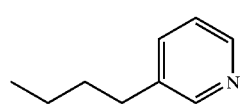 | H |
| Me | 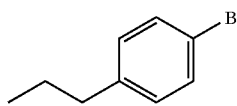 | H |
| Me | 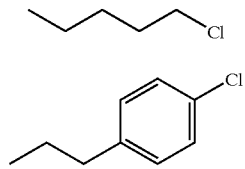 | H |
| Me | 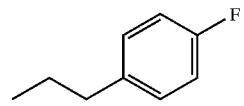 | H |
| Me | 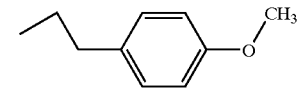 | H |
| Me |  | H |
| Me | 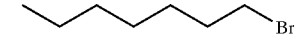 | H |
| Me | 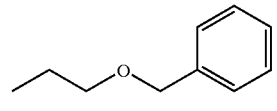 | H |
| Me | 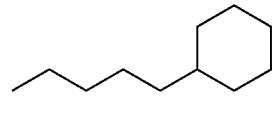 | H |
| Me | 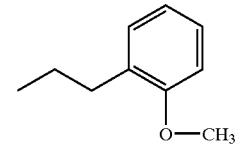 | H |

TABLE 1-continued

| | | |
|---|---|---|
| Me | butylcyclopentane | H |
| Me | pent-2-yne | H |
| Me | 2-propylnaphthalene | H |
| Me | dec-5-yne | H |
| Me | 1-pentyl-4-nitrobenzene | H |
| Me | 4-methyl-5-propylthiazole | H |
| Me | 1-propyl-4-methylbenzene | H |
| Me | 1-propyl-4-nitrobenzene | H |
| Me | hex-1-ene | H |
| Me | pentylbenzene | H |
| Me | 4-butylpyridine | H |
| Me | hexylbenzene | H |
| Me | 2-propyl-6-methylpyridine | H |
| Me | butan-2-one | H |

TABLE 1-continued
| Me |  | H |
| Me | 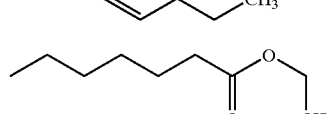 | H |
| Me | 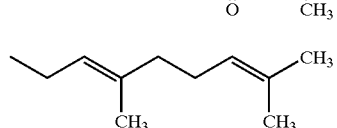 | H |
| Me | 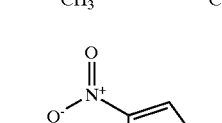 | H |
| Me | 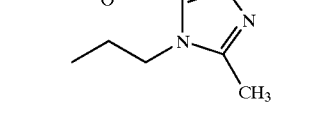 | H |
| Me | 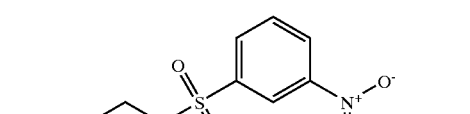 | H |
| Me | 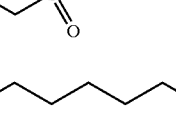 | H |
| Me | 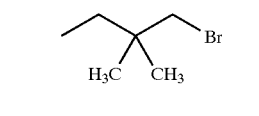 | H |
| Me | 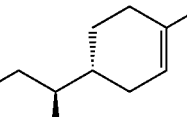 | H |
| Me | 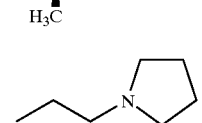 | H |
| Me |  | H |
| Me | 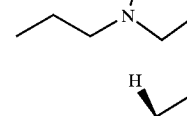 | H |
| Me |  | H |

TABLE 1-continued
| Me | 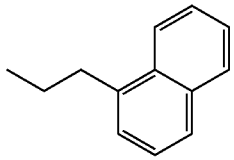 | H |
| Me | 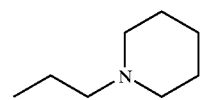 | H |
| Me | 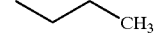 | H |
| Me | 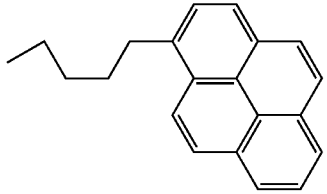 | H |
| Me | 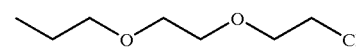 | H |
| Me | 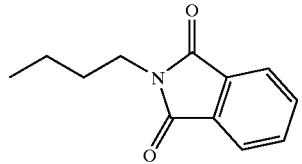 | H |
| Me | 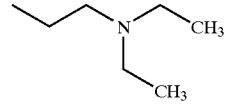 | H |
| Me | 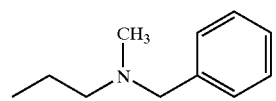 | H |
| Me | 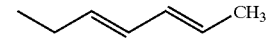 | H |
| Me | 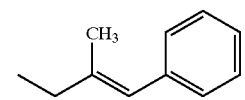 | H |
| Me | 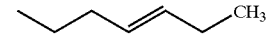 | H |
| Me | 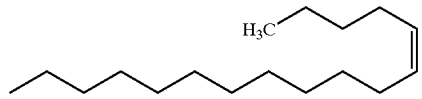 | H |

TABLE 1-continued

| | | |
|---|---|---|
| Me | (3-methylhex-2-enyl connected to 4-methylpent-3-enyl) | H |
| Me | 2,2-dimethylbutanal | H |
| Me | pentyl acrylate | H |
| Me | 4-ethylheptane | H |
| Me | 2-methylbutyl | H |
| Me | 2-propoxy-1,3,4-trifluorobenzene | H |
| Me | 1-(2-chloroethoxy)propyl | H |
| Me | 2-propylpyridine | H |
| Me | 2-(3-propoxypropyl)-6-methylpyridine | H |
| Me | 1-(4-bromophenoxy)propyl | H |
| Me | N-propyl-N-butyl-pentylamine | H |
| Me | propyl methyl sulfone | H |
| Me | propyl methyl sulfide | H |

TABLE 1-continued

| | | |
|---|---|---|
| Me | N-propyl-N-ethyl-(3-methylphenyl)amine | H |
| Me | propyl phenyl sulfone | H |
| Me | propyl phenyl sulfide | H |
| Me | propyl trimethylsilane | H |
| Me | 1,1,1-trifluorobutane | H |
| Me | 3-methyl-pentan-2-one | H |
| Me | 1-propyl-3-nitrobenzene | H |
| Me | butyl 2-methoxyethyl ether | H |
| Me | (Z)-dec-4-ene | H |
| Me | 4-methyl-2-(2,2-dimethylpropyl)heptane | H |
| Me | butylbenzene | H |
| Me | 3,7,11,15-tetramethylhexadec-2-ene | H |
| Me | 2,6-dimethyl-2-decene | H |

TABLE 1-continued

| Me | methyl 2,2-dimethylbutanoate | H |
| Me | 2-methyl-2-pentene | H |
| Me | 2-methyl-1-pentene | H |
| Me | 1-propyl-3-methylbenzene | H |
| Me | 2-hexyne | H |
| Me | 1,1,1,2,2,3,3-heptafluoropentane | H |
| Me | 1,1,2,2,3,3,4,4-octafluorohexane | H |
| Me | 1,1,2,2-tetrafluorobutane | H |
| Me | 1,1-diphenylpropane | H |
| Me | 2,2,4-trimethyl-hexane | H |
| Me | 4,5-dimethyl-3-ethyl-1,3-octadiene | H |
| Me | 1-chloropropane | H |

TABLE 1-continued

| | | |
|---|---|---|
| Me | 2-chloropropylbenzene | H |
| Me | neopentylbenzene derivative (2,2-dimethylbutylbenzene) | H |
| Me | 1-fluoropropyl | H |
| Me | propyl methacrylate | H |
| Me | sec-pentylbenzene (2-phenylbutane with methyl) | H |
| Me | propyl butyl diether (CH$_2$CH$_2$OCH$_2$CH$_2$OC$_4$H$_9$) | H |
| Me | isopropyl pentafluorobenzene | H |
| Me | 2-isopropyl-methoxybenzene | H |
| Me | 1-(trifluoromethyl)ethylbenzene | H |
| Me | 4-phenylpent-2-yne | H |
| Me | 1-(1-naphthyl)ethyl | H |

TABLE 1-continued

| | | |
|---|---|---|
| Me | 1-(2,4-dichlorophenyl)-2-chloropropyl | H |
| Me | 4-fluorocumyl | H |
| Me | 4-methoxycumyl | H |
| Me | 2-methyl-3-phenylpropyl (sec-butylbenzene) | H |
| Me | propyl isopropyl ether | H |
| Me | 3-methylpentan-3-yl (CH(Et)(CH(CH₃)CH₂CH₃)) | H |
| Me | 3-methylhexyl | H |
| Me | 2-methylbut-1-ene | H |
| Me | 2-methyl-1-propylbenzene | H |
| Me | 2-nitrobutane | H |
| Me | 1-nitropropane | H |
| Me | 1-(2-nitrophenyl)propyl | H |

TABLE 1-continued

| | | |
|---|---|---|
| Me | sec-butylbenzene | H |
| Me | 4-(methylthio)heptane | H |
| Me | 1-(methylthio)butane | H |
| Me | 1-ethoxy-2-methoxy-4-propylbenzene | H |
| Me | 2,3-dimethylpentane (with CH₃ groups) | H |
| Me | 2-nitrobutane | H |
| Me | (3-pentyl)benzene | H |
| Me | 1-methoxy-1,2-diphenylpropane | H |
| Me | 1-isopropyl-2-(trifluoromethyl)benzene | H |
| Me | 2-ethylpyrrolidine | H |
| Me | butyl methacrylate | H |

METHODS OF USE

The present invention is also directed to a method for inhibiting IL-12 signaling in a mammal having an inflammatory response (e.g., Th1 cell-mediated). The methods of the present invention generally comprise administering a pharmaceutically or therapeutically effective amount of a compound as described herein to a patient in need of such treatment whereby IL-12 signaling is inhibited. The patient may be a human or non-human mammal. For example, a patient will need treatment when exhibiting a deleterious inflammatory response in the course of a disease condition mediated by Th1 cells. Such need is determinable by skilled clinicians and investigations in the medical arts.

Preferred Th1 cell-mediated disease conditions that involve an inflammatory response may include, but are not limited to, the following exemplary conditions: (1) inflammatory diseases or disorders, such as, for example, arthritis, asthma, chronic inflammatory diseases, chronic intestinal inflammation, psoriasis, septic shock, septicemia, and adult respiratory distress syndrome; (2) autoimmune diseases or disorders, such as, for example, graft-versus-host disease (acute and/or chronic), autoimmune gastritis, autoimmune hemolytic anemia, autoimmune neutropenia, chronic active hepatitis, chronic thyroiditis, inflammatory bowel disease (e.g., Crohn's Disease and ulcerative colitis), lupus disorders (e.g., systemic lupus erythematosus), multiple sclerosis, myasthenia gravis, rheumatoid arthritis, scleroderma, thrombocytopenia, thyroid diseases (e.g., Graves' and Hashimoto's disease), type-1-IDDM, and uveitis; and (3) neurodengenerative diseases such as, for example, amyotrophic lateral sclerosis, Alzheimer's disease, Parkinson's disease, and primary lateral sclerosis. The method of the present invention is particularly useful in the treatment of autoimmune diseases, preferably as a therapy for treating MS and type-1-IDDM.

In a preferred embodiment, the present invention comprises a method for inhibiting a cellular process or activity mediated by IL-12, the method comprising:

(a) contacting IL-12 responsive cells with a compound of the present invention, as described above; and
(b) determining that the cellular process or activity mediated by IL-12 is inhibited.

PHARMACEUTICAL COMPOSITIONS AND DOSAGE

The compounds of the present invention can be administered in such oral dosage forms as tablets, capsules (each of which includes sustained release or timed release formulations), pills, powders, granules, elixirs, tinctures, suspension, syrups, and emulsions. Likewise, they may also be administered in intravenous (bolus or infusion), intraperitoneal, subcutaneous, or intramuscular form, all using dosage forms well known to those of ordinary skill in the pharmaceutical arts.

The compounds of the present invention can be administered by any means that produces contact of the active agent with the agent's site of action in the body of a mammal. They can be administered by any conventional means available for use in conjunction with pharmaceuticals, either as individual therapeutic agents or in a combination of therapeutic agents readily determinable by the skilled artisan. They can be administered alone, but are generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinary skilled physician or veterinarian can readily determine and prescribe the effective amount of the drug required to prevent, counter, or arrest the progress of the condition. Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition. By way of general guidance, the daily oral dosage of each active ingredient, when used for the indicated effects, will range between about 0.001 to 1000 mg/kg of body weight, preferably between about 0.01 to about 100 mg/kg of body weight per day, and most preferably between about 1.0 to 20 mg/kg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three or four times daily.

The compounds for the present invention can be administered in intranasal form via topical use of suitable intranasal vehicles, or via transdermal routes, using those forms of transdermal skin patches well known to those of skill in the art. To be administered in the form of a transdermal delivery system, the dosage administration will, of course, be continuous rather than intermittent throughout the dosage regimen.

In the methods of the present invention, the inventive compounds can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices. For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include, without limitation, starch, gelatin, natural sugars such as glucose or beta-lactose, corn sweeteners, natural and synthetic gums such as acacia, tragacanth, or sodium alginate, carboxymethylcellulose, polyethylene glycol, waves, and the like. Lubricants used in these dosage forms include, without limitation, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include, without limitation, polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salt and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences Useful pharmaceutical dosage-forms for administration of the compounds of this invention can be illustrated, without limitation, as follows:

Capsules. A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules. A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets. A large number of tablets are prepared by conventional procedures sothat the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatbility or delay absorption.

Injectable, A parenteral composition suitable for administration by injection is prepared by stirring 1.5% by weight of active ingredient in 10% by volume propylene glycol and water. The solution is made isotonic with sodium chloride and sterilized.

Suspension. An aqueous suspension is prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

The compounds of the present invention may be administered in combination with a second therapeutic agent such as, for example, a corticosteroid, analgesics, etc. The compounds of the present invention and such second therapeutic agent can be administered separately or as a physical combination in a single dosage unit, in any dosage form and by various routes of administration, as described above. The compounds of the present invention may be formulated together with the second therapeutic agent in a single dosage unit (that is, combined together in one capsule, tablet, powder, or liquid, etc.). When the compounds of the present invention and the second therapeutic agent are not formulated together in a single dosage unit, they may be administered essentially at the same time, or in any order, for example, the compounds of the present invention may be administered first, followed by administration of the second agent. When not administered at the same time, preferably the administration of a compound of the present invention and the second therapeutic agent occurs less than about one hour apart, more preferably less than about 5 to 30 minutes apart. Preferably the route of administration is oral. Although it is preferable that the inventive compound and the second therapeutic agent are both administered by the same route (that is, for example, both orally), if desired, they may each be administered by different routes and in different dosage forms (that is, for example, one component of the combination product may be administered orally, and another component may be administered intravenously).

The dosage when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above. The proper dosage of a compound of the present invention when administered in combination with the second therapeutic agent will be readily ascertainable by a medical practitioner skilled in the art, once armed with the present disclosure.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

SYNTHESIS

Compounds of the present invention can be synthesized using the methods described in the Examples below, which are preferred, as well as by synthetic methods known in the art of synthetic organic chemistry, or variations thereon as readily appreciated and readily performable by those skilled in the art. The various synthetic steps described herein may be performed in an alternate sequence or order to give the desired compounds. Moreover, the synthesis Examples described herein are not intended to comprise a comprehensive list of all means by which the compounds described and claimed in this patent application may be synthesized.

For example, 1,3,7-trisubstituted xanthine-based compounds of the present invention may be synthesized from 1,3-disubstituted xanthine compounds, 1,7-disubstituted xanthine compounds, or 3,7-disubstituted xanthine compounds. The 1,3,7-trisubstituted xanthine compound may be prepared by treating a 1,3-disubstituted xanthine compound with an appropriate base in a suitable solvent to provide an anion which undergoes a substitution reaction with a compound substituted with an appropriate leaving group. Suitable bases include, but are not limited to, sodium hydride and potassium tert-butoxide. Suitable solvents include, but are not limited to, dimethylformamide, dimethylsulfoxide and tetrahydrofuran. Suitable leaving groups include, but are not limited to, chloro, bromo, iodo, methanesulfonato, trifluoromethanesulfonato and p-toluenesulfonato.

Alternatively, 1,3,7-Trisubstituted xanthine compounds may be synthesized from 1,3-disubstituted xanthine compounds, 1,7-disubstituted xanthine compounds, or 3,7-disubstituted xanthine compounds using so called Mitsunobu reaction conditions. For example, 1,3,7-Trisubstituted xanthine compounds may be prepared by treating a 1,3-disubstituted xanthine compound with a compound substituted with an alcohol group. The alcohol group is activated to undergo a substitution reaction after treatment with an appropriate phosphine compound and an appropriate azo compound in a suitable solvent. Suitable phosphone compounds include, but are not limited to, triphenylphosphine and tributylphosphine. An appropriate azo compound includes, but is not limited to, diethylazodicarboxylate. A suitable solvent includes, but is not limited to, tetrahydrofuran.

8-Alkylsulfanylxanthine compounds are synthesized from 8-mercaptoxanthine compounds which undergoes a substitution reaction with a compound substituted with an appropriate leaving group. The substitution reaction is conducted in the presence or absence of an appropriate base in a suitable solvent. Appropriate leaving groups include, but are not limited to, chloro, bromo, iodo, methanesulfonato, trifluoromethanesulfonato and p-toluenesulfonato. An appropriate base includes, but is not limited to, potassium carbonate. Suitable solvents include, but are not limited to, acetonitrile, dimethylformamide, dimethylsulfoxide and tetrahydrofuran.

8-Aminoxanthine compounds may be synthesized from xanthine compounds substituted on the 8-position with an appropriate leaving group in a substitution reaction with a compound containing an amino group. The substitution reaction is carried out in a suitable solvent. Appropriate leaving groups include, but are not limited to, chloro, bromo, iodo, methanesulfonato, trifluoromethanesulfonato and p-toluenesulfonato. Suitable solvents include, but are not limited, to dimethylformamide, dimethylsulfoxide and tetrahydrofuran.

8-Aminomethylxanthine compounds may be synthesized from 8-methylxanthine compounds substituted on the 8-methyl substituent with an appropriate leaving group in a substitution reaction with a compound containing an amino group. The substitution reaction is conducted in a suitable solvent. Appropriate leaving groups include, but are not limited to, chloro, bromo, iodo, methanesulfonato, trifluoromethanesulfonato and p-toluenesulfonato. Suitable solvents include, but are not limited to, dimethylformamide, dimethylsulfoxide and tetrahydrofuran.

As can be appreciated by the skilled artisan, the preferred synthetic schemes described above and in the Examples below are not intended to comprise a comprehensive list of all means by which the compounds described and claimed herein may be synthesized. It should be understood that the specified materials and conditions are important in practicing the invention but that unspecified materials and conditions are not excluded so long as they do not prevent the benefits of the invention from being realized. Other suitable methods and starting materials will be evident to those having skill in the art. Additionally, the various synthetic steps described may be performed in an alternate sequence or order to give the desired compounds.

EXAMPLES

The present invention will be further illustrated in the following, non-limiting Examples. The Examples are illustrative only and do not limited the claimed invention regarding the materials, conditions, process parameters and the like recited herein.

Example 1

Synthesis of 1-(5-(N-Hydroxy)aminohexyl)-3,7-dimethylxanthine (CT7549)

Sodium cyanoborohydride (62.84 mg, 1 mmol) was added to a solution of 1-(5-oximinohexyl)-3,7-dimethylxanthine (Klein, J. P.; Leigh, A. Oxime Substituted Therapeutic Compounds, U.S. Pat. No. 5,770,595 (Jun. 23, 1998)) (293 mg, 1 mmol) in methanol (10 ml). 1 M hydrogen chloride in ether was added to pH 4–5. After stirring for 3 hours, the mixture was concentrated under reduced pressure. 1 N aqueous sodium hydroxide solution to pH 9–10 (10 ml). The mixture was extracted with 10% methanol-dichloromethane (3×50 ml). The combined extracts were washed with water (50 ml), dried over anhydrous magnesium sulfate and concentrated under reduced pressure. The residue was purified by flash chromatography on silica gel eluting with 10% methanol-dichloromethane to provide 1-(5-(N-hydroxy)aminohexyl)-3,7-dimethylxanthine (180 mg).

Example 2

Synthesis of (R)-3-(5-Hydroxyhexyl)-1,7-dimethylxanthine (CT11495)

To a stirring solution of 1,7-dimethylxanthine (0.30 g, 1.67 mmol) in dimethylsulfoxide (20 ml) was added sodium hydride (42 mmg, 1.75 mmol) in one portion. After stirring for 30 minutes, (R)-5-acetoxy-1-bromohexane (0.31 g, 1.75 mmol) was added next. (R)-5-Acetoxy-1-bromohexane was prepared according to methods described in U.S. patent application Ser. No. 09/002,345, which is incorporated herein by reference. After heating at 80° C. for 18 hours, water (25 ml) was added and the aqueous solution was extracted with dichloromethane (3×20 ml). The combined extracts were washed with saturated aqueous sodium chloride solution (50 ml), dried over sodium sulfate and concentrated under reduced pressure. The residue was purified by flash chromatography on silica eluting with ethyl acetate to give (R)-3-(5-acetoxyhexyl)-1,7-dimethylxanthine (0.34 g, 64%, yield) as a colorless oil.

To a stirring solution of (R)-3-(5-acetoxyhexyl)-1,7-dimethylxanthine (0.28 g, 0.87 mmol) in methanol (20 ml) was added an anhydrous solution of hydrogen chloride in ethyl ether (1 M, 2.6 ml, 2.6 mmol). After refluxing for 4 hours, the mixture was concentrated under reduced pressure. The residue was treated with saturated aqueous solution of sodium bicarbonate solution (30 ml) and extracted with dichloromethane (3×20 ml). The combined extracts were washed with saturated aqueous sodium chloride solution (30 ml), dried over sodium sulfate and concentrated under reduced pressure to give (R)-3-(5-hydroxyhexyl)-1,7-dimethylxanthine (0.20 g, 85% yield) as a colorless oil that solidified on standing.

Example 3

Synthesis of (R)-1-(5-Hydroxyhexyl)-3,7-dimethyluric acid (CT11499)

To a stirring solution of 3,7-dimethyluric acid (0.40 g, 2.04 mmol) in dimethylsulfoxide (20 ml) was added sodium hydride (49 mg, 2.04 mmol) in one portion. After stirring for 45 minutes, a solution of chloromethyl pivalate (0.29 g, 2.04 mmol) in dimethylsulfoxide (1 ml). After stirring for 24 hours, water (50 ml) was added. After cooling to room temperature, the solid was filtered, rinsed with water (4×20 ml), with ether (20 ml) and dried under vacuum to give 9-pivaloyloxymethyl-3,7-dimethylfuric acid (0.18 g, 28% yield) as a white solid.

To a stirring solution of 9-pivaloyloxymethyl-3,7-dimethyluric acid (0.14 g, 0.45 mmol) in dimethylsulfoxide (10 ml) was added sodium hydride (12 mg, 0.47 mmol) in one portion. The solution was stirred for 15 minutes. (R)-5-Acetoxy-1-iodohexane (0.13 g, 0.47 mmol) in dimethylsulfoxide (1 ml) was added. The solution of (R)-5-acetoxy-1-iodohexane was prepared according to methods described in U.S. patent application Ser. No. 09/002,345, which is incorporated herein by reference. After stirring at room temperature for 24 hours, water (25 ml) was added and the aqueous solution was extracted with ethyl acetate (3×15 ml). The combined extracts were washed with saturated aqueous sodium chloride solution (15 ml), dried over sodium sulfate and concentrated under reduced pressure. The residue was purified by flash chromatography on silica eluting with ethyl acetate to give (R)-1-(5-acetoxyhexyl)-9-pivaloyloxymethyl-3,7-dimethyluric acid (0.10 g, 50% yield) as a white solid.

To a stirring solution of (R)-1-(5-acetoxyhexyl)-9-pivaloyloxymethyl-3,7-dimethyluric acid (0.10 g, 0.22 mmol) in methanol (5 ml) was added solid sodium methoxide (48 mg, 0.88 mmol) in one portion. After stirring at room temperature for 4 days, the mixture was treated with 5% aqueous hydrochloride acid solution (0.25 ml) and concentrated under a stream of nitrogen and mild heating. The residue was purified by preparative thin layer chromatography (250 micron silica gel plate) eluting with 7% methanol-dichloromethane to provide (R)-1(5-hydroxyhexyl)-3,7-dimethyluric acid (20 mg, 30% yield) as a white solid.

Example 4

Synthesis of (R)-1-(5-Hydroxy xyl)-7-benzyl-3,8-dimethylxanthin (CT12407)

Glacial acetic acid (4.5 ml, 75 mmol) was added to a suspension of 6-amino-1-methyluracil (5.66 g, 50 mmol) in hot (100 ml). Sodium nitrite (4.14 g) was added in portions and the reaction mixture was stirred for 1 hour. The precipitate was collected by filtration, washed with water (75 ml) and then suspended in water (100 ml). The mixture was warmed to 50° C. and sodium dithionite (10 g) was added in portions keeping the temperature of the reaction between 50–55° C. The mixture was stirred at 50° C. for 1 hr and then cooled to room temperature and filtered. The solid was washed with water (2×25 ml), acetone (2×25 ml) and dried under vacuum to provide 5,6-diamino-1-methyluracil (5.6 g).

A solution of 5,6-diamino-1-methyluracil (2.5 g) in acetic anhydride (25 ml) was heated at reflux for 2 hours and then the acetic anhydride was evaporated under reduced pressure. The residue was dissolved in 10% aqueous sodium hydroxide solution (50 ml) and heated at reflux for 2 hours. After cooling to room temperature, the mixture was acidified to pH 4 by addition of concentrated hydrochloric acid. The precipitate was filtered, washed with water (15 ml), rinsed with acetone (15 ml) and dried under vacuum to provide 3,8-dimethylxanthine (1.8 g).

A solution of sodium hydroxide (400 mg) in water (5 ml) was added to a suspension of 3,8-dimethylxanthine (1.80 g) in methanol (10 ml). After stirring for 1 hour at 70° C., benzyl bromide (1.2 ml) was added. After stirring for 5 hours at 70–80° C., the solvent was evaporated under reduced pressure. The residue was treated with saturated aqueous ammonium chloride solution (50 ml) and extracted with ethyl acetate (3×75 ml). The combined extracts were washed with saturated aqueous sodium chloride solution (30 ml), dried over magnesium sulfate and concentrated under reduced pressure. The solid was purified by recrystallization from ethanol to provide 7-benzyl-3,8-dimethylxanthine (1.06 g).

7-Benzyl-3,8-dimethylxanthine (500 mg, 1.85 mmol) was added to a suspension of sodium hydride (50.5 mg) in anhydrous dimethylsulfoxide (20 ml). After stirring for 30 minutes, (R) 5-acetoxy-1-chlorohexane (357 mg) was added and the mixture was warmed to 70–80° C. for 12 hours. The (R) 5-acetoxy-1-chlorohexane was prepared according to methods described in U.S. Pat. No. 5,629,423 issued to Klein, J. P., Leigh, A. J., Michnick, J., Kumar, A. M., Underiner, G. E., on May 13, 1997. After cooling to room temperature, the reaction wash quenched by the addition of water (50 ml) and extracted with ethyl acetate (3×75 ml). The combined extracts were washed with water (2×50 ml), washed with saturated aqueous sodium chloride solution (50 ml), dried over anhydrous magnesium sulfate and concentrated under reduced pressure. The residue was purified by flash chromatography on silica gel eluting with ethyl acetate to give (R)-1-(5-acetoxyhexyl)-7-benzyl-3,8-dimethylxanthine (638 mg).

A solution of (R)-1-(5-Acetoxyhexyl)-7-benzyl-3,8-dimethylxanthine (500 mg) in methanol (20 ml) was combined with hydrogen chloride in ether (1 M, 2.5 ml) and stirred at room temperature for 12 hours. After evaporation of the solvent under reduced pressure, the residue was dissolved in ethyl acetate (100 ml). The solution was washed with saturated aqueous sodium bicarbonate solution (30 ml), dried over magnesium sulfate and concentrated under reduced pressure to provide (R)-1-(5-hydroxyhexyl)-7-benzyl-3,8-dimethylxanthine (420 mg).

Example 5

Synthesis of (R)-3-(2-Furylmethyl)-1-(5-hydroxyhexyl)-7-methylxanthine (CT12422)

To a stirring solution of furfuryl alcohol (6.0 ml, 69.4 mmol) and carbon tetrabromide (29.9 g, 90.2 mmol) in dichloromethane (70 ml) at 0° C. was added triphenylphosphine (23.7 g, 90.2 mmol) slowly over 30 minutes (rapid addition results in polymerization of furfuryl moieties as evidenced by a black-green solution). The reaction was stirred at 0° C. for an additional 30 minutes and then at room temperature for 1.5 hours. Evaporation of the solvent under reduced pressure provided an oil that was treated with hot hexane (150 ml). After cooling to room temperature the solid was filtered. The filtrate was treated with activated charcoal (10 g), stirred for 1 hour and filtered through a pad of celite. The filtrate was concentrated under reduced pressure. The residue was immediately distilled (43–46° C., 23 mm) with careful exclusion of air to give furfuryl bromide (10.2 g, 91% yield) as a colorless coil which was used immediately in the next step.

To a stirring suspension of 7-methylxanthine (2.54 g, 15.3 mmol) in dimethylsulfoxide (80 ml) was added sodium hydride (0.37 mg, 15.3 mmol) in one portion. After stirring for 30 minutes, freshly prepared furfuryl bromide (2.5 g, 15.3 mmol) was added next. After stirring at room temperature for 18 hours, the reaction was quenched by addition of water (150 ml). Saturated aqueous sodium chloride solution (30 ml) was added and the mixture was extracted with chloroform (4×50 ml). The combined extracts were washed with saturated aqueous sodium bicarbonate solution (3×50 ml), with saturated aqueous sodium chloride solution (2×50 ml) and dried over a mixture of sodium sulfate and activated charcoal. After filtration through a pad of celite, the solvent was evaporated under reduced pressure. The residue was treated with ethyl acetate. The solid was filtered, rinsed with cold ethyl acetate (2×25 ml) and vacuum dried to give 3-(2-furylmethyl)-7-methylxanthine (0.54 g, 1496 yield) as a beige solid.

To a stirring suspension 3-(2-furylmethyl)-7-methylxanthine (0.40 g, 1.62 mmol) in dimethylsulfoxide (20 ml) was added sodium hydride (41 mg, 1.71 mmol) in one portion. After stirring for 25 minutes, (R)-5-acetoxy-1-iodohexane (0.46 g, 1.71 mol) was added neat. After stirring at room temperature for 72 hours, the reaction was quenched by the addition of water (75 ml) and extracted with ethyl acetate (3x 35 ml). The combined extracts were washed with saturated aqueous sodium chloride solution (2x 35 ml), dried over sodium sulfate and concentrated under reduced pressure. The residue was purified by flash chromatography on silica gel eluting with ethyl acetate to give (R)-1-(5-acetoxyhexyl)-3-(2-furylmethyl)-7-methylxanthine (0.49 g, 78% yield) as a colorless oil.

To a stirring solution of (R)-1-(5-acetoxyhexyl)-3-(2-furylmethyl)-7-methylxanthine (0.42 g, 1.07 mmol) in methanol (20 ml) was added a solution of hydrogen chloride in 1,4-dioxane (4 M, 0.80 ml, 3.21 mmol) and the mixture was refluxed for 5 hours. After cooling to room temperature, the solvent was evaporated under reduced pressure. The residue was treated with saturated aqueous sodium bicarbonate solution (25 ml) and the mixture was extracted with dichloromethane (3x 25 ml). The combined extracts were washed with saturated aqueous sodium chloride solution (2x 25 m), dried over sodium sulfate and concentrated under reduced pressure. The residue was purified by flash chromatography on silica gel eluting with ethyl acetate to provide (R)-3-(2-furylmethyl)-1-(5-Hydroxyhexy;)-7-methylxanthine (0.30 g, 80% yield).

Example 6

Synthesis of (R)-8-Aminomethyl-1-(5-hydroxyhexyl)-3-methylxanthine (CT12440)

To a stirring suspension of 3-methylxanthine (7.9 g 47.6 mmol) and sodium acetate (7.81 g, 95.2 mmol) in glacial acetic acid (120 ml) was added bromine (9.14 g, 57.1 mmol). The mixture was stirred at 65° C. for 2 hours. After cooling to room temperature the precipitate was filtered, washed with acetic acid (2x 15 ml), water (3x 50 ml) and dried under vacuum to give 8-bromo-3-methylxanthine (10.5 g, 90% yield) as a beige powder.

To a stirring suspension of 8-bromo-3-methylxanthine (7.06 g, 28.8 mmol) and potassium carbonate (3.98 g, 28.8 mmol) in DMF (150 ml) was added chloromethyl ethyl ether (2.72 g, 28.8 mmol). After stirring overnight at room temperature, the reaction mixture was poured into ice-cold water (650 ml). After stirring at 0–5° C. for 1 hour, the cloudy mixture was filtered, washed with water (3x 15 ml) and dried under vacuum to provide 8-bromo-7-ethoxymethyl-3-methylxanthine (6.15 g, 70% yield) as a white solid.

To a stirring suspension of 8-bromo-7-ethoxymethyl-3-methylxanthine (1.52 g, 5.0 mmol) in anhydrous dimethylsulfoxide (20 ml) was added sodium hydride (144 mg, 6.0 mmol). The mixture was stirred at room temperature for 30 min and then (R)-5-cetoxy-1-chlorohexane (983 mg, 5.5 mmol) was added and the mixture was stirred at 70–75° C. After 12 hours, the mixture was cooled to room temperature, quenched with saturated aqueous sodium chloride solution (100 ml) and extracted with ethyl acetate (3x 50 ml). The combined extracts were washed with water (2x 25 ml), with saturated aqueous sodium chloride solution (25 ml) and dried over magnesium sulfate. After evaporation of the solvent under reduced pressure, the product was purified by flash chromatography over silica gel eluting with ethyl acetate to provide (R)-1-(5-acetoxyhexyl)-8-bromo-7-ethoxymethyl-3-methylxanthine (1.83 g, 82% yield) as a beige solid.

To a solution of (R)-1-(5-acetoxyhexyl)-8-bromo-7-ethoxymethyl-3-methylxanthine (1.83 g, 4.11 mmol) and sodium iodide (123 mg, 0.82 mmol) in anhydrous dimethylsulfoxide (40 ml) was added potassium cyanide (294 mg, 4.52 mmol). After stirring at room temperature for 58 hours, the mixture was treated with water (200 ml) and extracted with ethyl acetate (4x 25 ml). The combined extracts were washed with saturated aqueous sodium chloride solution (25 ml) and then dried over magnesium sulfate. After the solvent was evaporated under reduced pressure, the product was purified by flash chromatography on silica get eluting with ethyl acetate-hexane (1:3) to provide (R)-1-(5-Acetoxyhexyl)-8-cyano-7-ethoxymethyl-3-methylxanthine (970 mg, 60% yield) as a pale yellow oil.

A suspension of (R)-1-(5-acetoxyhexyl)-8-cyano-7-ethoxymethyl-3-methylxanthine (750 mg, 1.92 mmol) and 10% palladium on carbon (250 mg) in glacial acetic acid (40 ml) was treated with hydrogen gas (80 psi) on a Parr shaker for 3 hours. The mixture was filter through a pad of celite and then the filtrate was concentrated under reduced pressure to provide the acetic acid salt of (R)-1-(5-Acetoxyhexyl)-8-aminomethyl-7-ethoxymethyl-3-methylxanthine (800 mg, 91% yield) as a pale yellow oil.

To a stirring solution of (R)-1-(5-acetoxyhexyl)-8-aminomethyl-7-ethoxymethyl-3-methylxanthine acetic acid salt (300 mg, 0.66 mmol) in ethanol (20 ml) was added an anhydrous solution of hydrogen chloride in ethyl ether (1M, 2.0 ml, 2.0 mmol). After heating at reflux overnight, the solvent was evaporated under reduced pressure to provide the product as a pale yellow oil. Hexane (5.0 ml) was added. After stirring for 1 hour, the resulting precipitate was filtered to provide the hydrochloride salt of (R)-1-(5-hydroxyhexyl)-8-aminomethyl-3-methylxanthine (150 mg, 59% yield) as a white powder.

Example 7

(R)-1-5-Hydroxyh xyl)-3-ethyl-8-N-methyl)aminom thylxanthin (CT12441)

To a stirring suspension of 8-bromo-3-methylxanthine (prepared as described for CT12440) (12.25 g, 50.0 mmol) and potassium carbonate (6.91 g, 50.0 mmol) in dimethylformamide (400 ml) was added benzyl bromide (9.20 g, 54.0 mmol). After stirring for 12 hours, the mixture was poured into cold water (680 ml). The precipitate was filtered, washed with water (3x 50 ml), ether (3x 50 ml) and dried under vacuum to provide 7-benzyl-8-bromo-3-methylxanthine (14.92 g, 89% yield) as a white powder.

To a stirring suspension of 7-benzyl-8-bromo-3-methylxanthine (10.06 g, 30.0 mmol) in anhydrous dimethylsulfoxide was added sodium hydride (864 mg, 36.0 mmol). After stirring at room temperature for 30 min, (R)-5-acetoxy-1-chlorohexane (5.9 g, 33.0 mmol) was added. After stirring at 70–75° C. for 12 hours, the mixture was cooled to room temperature, quenched with water (600 ml) and stirred at room temperature for 4 hours. The precipitate was filtered to provide (R)-1-(5-Acetoxyhexyl)-7-benzy)-8-bromo-3-methylxanthine (12.31 g, 86% yield) as a beige powder.

To a solution of (R)-1-(5-acetoxyhexyl)-7-benzyl-8-bromo-3-methylxanthine (9.55 g, 20.0 mmol) in anhydrous dimethylsulfoxide was added potassium cyanide (1.43 g, 22.0 mmol). After stirring at 70–80° C. for 4.5 hours, the mixture was cooled to room temperature, quenched with water (500 ml) and extracted with ethyl acetate (4x 150 ml). The combined extracts were washed with saturated aqueous sodium chloride solution (45 ml), dried over magnesium sulfate and the solvent was evaporated under reduced pressure. The crude product was purified by flash chromatography on silica gel eluting with ethyl acetate-hexane (1:1) to provide (R)-1-(5-acetoxyhexyl)-7-benzyl-8-cyano-3-methylxanthine (7.60 g, 90% yield) as a beige powder.

A suspension of (R)-1-(5-Acetoxyhexyl)-7-benzyl-6-cyano-3-methylxanthine(850 mg, 2.0 mmol) and 10% Pd on carbon (300 mg) in glacial acetic acid (60 ml) was treated with hydrogen gas (80 psi) on a Parr shaker for 3 hours. After filtering through a pad of celite, the filtrate was concentrated under reduced pressure to provide the acetic acid salt of (R)-1-(5-acetoxyhexyl)-8-aminomethyl-7-benzyl-3-methylxanthine.

To a stirring solution of (R)-1-(5-acetoxyhexyl)-8-aminomethyl-7-benzyl-3-methylxanthine in chloroform (30 ml) was added trifluoroacetic anhydride (1.0 g, 4.76 mmol). After stirring for 3 hours, the solvent was evaporated under reduced pressure. The crude product was purified by flash chromatography on silica gel eluting with ethyl acetate to provide (R)-1-(5-acetoxyhexyl)-7-benzyl-8-N-trifluoroacetylaminomethyl-3-methyl-xanthine (1.0 g, 95% yield) as a white powder.

To the suspension of sodium hydride (36 mg, 1.5 mmol) in DMF (10 ml) was added (R)-1-(5-acetoxyhexyl)-7-benzyl-8-N-trifluoroacetylaminomethyl-3-methylxanthine (520 mg. 1.0 mmol). After stirring at room temperature for 30 minutes, methyl iodide (1.0 ml) was added. After stirring at room temperature overnight, the mixture was poured into water (50 ml), extracted with ethyl acetate (3x 20 ml) and dried over magnesium sulfate Evaporation of the solvent under reduced pressure provided (R)-1-(5-acetoxyhexyl)-7-benzyl-8-N-methyl-N-trifluoroacetylaminomethyl-3-methylxanthine.

A suspension of (R)-1-(5-acetoxyhexyl)-7-benzyl-8-N-methyl-N-trifluoroacetylaminomethyl-3-methylxanthine and 20% Pd(OH)$_2$ on carbon (300 mg) in glacial acetic acid (50 ml) was treated with hydrogen gas (82 psi) on a Parr shaker for 24 hours. After filtering through a pad of celite, the filtrate was concentrated under reduced pressure. The crude product was purified by flash chromatography on silica gel eluting with ethyl acetate to provide (R)-1-(5-Acetoxyhexyl)-8-N-methyl-N-trifluoroacetylaminomethyl-3-methylxanthine (380 mg, 85% yield) as a white powder.

To a stirring solution of (R)-1-(5-acetoxyhexyl)-8-N-methyl-N-trifluoroacetylaminomethyl-3-methylxanthine (380 mg, 0.85 mmol) in methanol (30 ml) was added an anhydrous solution of hydrogen chloride in ethyl ether (1 M, 2.0 ml, 2.0 mmol). After stirring at room temperature for 24 hours, the solvent was evaporated under reduced pressure. The resulting oil was treated with methanol (22.5 ml), water (2.25 ml) and potassium carbonate (900 mg, 5.0 mmol). After stirring at room temperature for 1 hour, the mixture was filtered and the filtrate was evaporated under reduced pressure. The crude product was purified by flash chromatography on silica gel eluting with chloroform-methanol (1:1) to provide (R)-1-(5-hydroxyhexyl)-3-methyl-8-(N-methyl)aminomethylxanthine (170 mg, 64% yield) as a colorless oil.

Example 8

Synthesis of (R)-1-(5-Hydroxyhexyl)-3-methyl-8-ethylaminoxanthine (CT12447)

8-Bromo-7-ethoxymethyl-3-methylxanthine (prepared as described for CT12440) (3.03 g, 10 mmol) was added to a suspension of sodium hydride (264 mg, 11 mmol) in anhydrous dimethylsulfoxide (60 ml). After stirring for 30 minutes, (R) 5-acetoxy-1-chlorohexane (1.963 g, 11 mmol) was added and the mixture was heated at 70–80° C. for 12 hours. After cooling to room temperature, the reaction was quenched by the addition of water (150 ml) and extracted with 10% methanol-ethyl acetate (3x 25 ml). The combined extracts were washed with water (2x 50 ml), with saturated aqueous sodium chloride solution (50 ml), dried over magnesium sulfate and concentrated under reduced pressure. The residue was purified by flash chromatography on silica gel eluting with 30% ethyl acetate-hexane to provide (R)-1-(5-acetoxyhexyl)-8-bromo-7-ethoxymethyl-3-methylxanthine (2.778).

A 40% aqueous solution of methylamine (10 ml) was added to a solution of (R)-1-(5-acetoxyhexyl)-8-bromo-7-ethoxymethyl-3-methylxanthine (0.450 g) in dimethylsulfoxide (20 ml). After heating at 70° C. for 6 hours, the mixture was treated with water (50 ml) and extracted with ethyl acetate (3x 50 ml). The combined extracts were washed with water (2x 30 ml), dried over magnesium sulfate and concentrated under reduced pressure. The residue was purified by flash chromatography on silica gel eluting with 10% methanol-ethyl acetate to provide (R)-1-(5-acetoxyhexyl)-7-ethoxymethyl-3-methyl-8-methylaminoxanthine (0.32 g).

A solution of (R)-1-(5-acetoxyhexyl)-7-ethoxymethyl-3-methyl-8-methylaminoxanthine (0.32 g) in methanol (10 ml) was heated in presence of concentrated hydrochloric acid (2 drops) for 12 hours to 70° C. After evaporation of the solvent under reduced pressure, the residue was dissolved in 20% methanol-ethyl acetate (50 ml). The solution was washed with saturated sodium bicarbonate solution (20 ml), dried over anhydrous magnesium sulfate and concentrated under reduced pressure. The residue was purified by flash chromatography on silica gel eluting with 10% methanol-ethyl acetate to provide (R)-1-(5-hydroxyhexyl)-3-methyl-8-methylaminoxanthine (0.100 g).

Example 9

Synthesis of (R)-1-(5-Hydroxyhexyl)-3-ethyluric acid (CT12452)

To a stirring suspension of sodium hydride (5.52 g, 230 mmol) in anhydrous dimethylsulfoxide (500 ml) was added 6-amino-1-methyluracil (28.2 g, 200 mmol). After stirring at room temperature under argon for 2 hours, (R)-5-Acetoxy-1-chlorohexane (37.5 g, 210 mmol) was added neat and the mixture was stirred at 80° C. for 16 hours. After cooling to room temperature, the mixture was poured into saturated aqueous sodium chloride solution (1500 ml) and extracted with ethyl acetate (9x 200 ml). The combined extracts were washed with water (2x 50 ml), with saturated aqueous sodium chloride solution (50 ml) and dried over magnesium sulfate. After evaporation of the solvent under reduced pressure, the resulting oil was treated with ethyl ether (400 ml). After stirring overnight at room temperature, the precipitate was filtered and rinsed with ether (2x 50 ml) to provide (R)-3-(5-acetoxyhexyl)-6-amino-1-methyluracil (44.0 g, 78% yield) as a beige powder.

To the stirring solution of (R)-3-(5-acetoxyhexyl)-6-amino-1-methyluracil (1.13 g, 4.0 mmol) in glacial acetic acid (22.5 ml) and water (7.5 ml) at 65° C. was added sodium nitrite (345 mg, 5.0 mmol) in portions. The pink mixture was stirred at 65° C. for 1 hour and then cooled to 0–5° C. After filtration, the violet solid was washed with water (2x 10 ml) and then suspended in water (20 ml) and heated at 65° C. while sodium hydrosulfite (2.78 g, 16.0 mmol) was added in portions. The pale yellow solution was stirred at 65° C. for an additional 1 hour, cooled to room temperature and extracted with chloroform (3x 25 ml). The combined extracts were dried over magnesium sulfate and filtered to provide crude (R)-3-(5-acetoxyhexyl)-5,6-diamino-1-methyluracil in chloroform. To this clear solution was added 1,1'-carbonyldiimidazole (650 mg, 4.0 mmol). After stirring overnight at room temperature, the mixture was washed with water (2x 25 ml), with 1 N aqueous hydrochloric add (2x 25 ml), with water (2x 25 ml), with saturated aqueous sodium chloride solution (25 ml) and then dried over magnesium sulfate. Evaporation of the solvent under reduced pressure provided the crude product which was purified by flash chromatography on silica gel eluting with ethyl acetate to provide (R)-1-(5-acetoxyhexyl)-3-methyluric acid (280 mg) as a beige solid which was dissolved in 20 ml of ethanol. To this solution was added hydrogen chloride in ethyl ether (1 M, 2.0 ml, 2.0 mmol). After refluxing overnight, the solvent was evaporated under reduced pressure. The crude product was purified by flash chromatography on silica gel eluting with ethyl acetate-methanol (7:1) to provide (R)-1-(5-hydroxyhexyl)-3-methyluric acid (210 mg, 19% yield) as a beige solid.

Example 10

Synthesis of (R)-3-(5-Hydroxyhexyl)-1,7,9-dimethyl-2,4-pyrrolo[2,3-d]pyrimidinedione (CT12458)

To a stirring solution of sulfuryl chloride in dichloromethane (1 M, 100 ml) was added propionaldehyde (7 ml, 97 mmol) over 30 seconds. After stirring for 1 hour, methanol (24 ml) was added over 5 minutes. Vigorous gas evolution and refluxing was observed during this addition. After stirring at room temperature for 150 minutes, dichloromethane (75 ml) was removed by distillation. The remaining mixture was treated with saturated aqueous sodium bicarbonate solution (100 ml). The mixture was extracted with ether (100 ml). The extract was dried over magnesium sulfate and concentrated under vacuum to provide 2-chloropropionaldehyde dimethyl acetal (3.7 g, 27% yield).

To a mixture of water (3 ml), tetrahydrofuran (3 ml) and 2-chloropropionaldehyde dimethyl acetal (1.46 g, 10.5 mmol) was added concentrated hydrochloric acid (0.2 ml) and stirred at 80–90° C. for 25 minutes. After cooling to room temperature, sodium acetate (800 mg) was dissolved in the aqueous phase. An aliquot (1 ml) of the upper organic phase was transferred to a stirring mixture of (R)-3-(5-acetoxyhexyl)-6-amino-1-methyluracil (prepared as described above for CT12452) (355 mg, 1.29 mmol), sodium acetate (500 mg) and water (8.5 ml) heated at 85° C. The mixture was heated at 85° C. for 40 minutes. After cooling to room temperature, the mixture was extracted with dichloromethane (2x 15 ml). The combined extracts were dried over magnesium sulfate and concentrated under vacuum. The residue was purified by flash chromatography on silica gel eluting with ethyl acetate to provide (R)-3-(5-acetoxyhexyl)-1,9-dimethyl-2,4-pyrrolo[2,3-d]pyrimidinedione (180 mg, 43% yield) as a pink solid.

A mixture of (R)-3-(5-acetoxyhexyl)-1,9-dimethyl-2,4-pyrrolo[2,3-d]pyrimidinedione (80 mg, 0.25 mmol), sodium hydride (15 mg, 0.62 mmol) and anhydrous dimethylsulfoxide (2 ml) was stirred for 3 minutes and then methyl iodide (31 ul, 0.5 mmol) was added. After stirring for 2 hours, the reaction was quenched by addition of water (10 ml). The mixture was extracted with dichloromethane (3x 15 ml). The combined extracts were dried over magnesium sulfate and concentrated under vacuum to provide (R)3-(5-acetoxyhexyl)-1,7,9-trimethyl-2,4-pyrrolo[2,3-d]pyrimidinedione (80 mg).

To a solution of (R)-3-(5-acetoxyhexyl)-1,7,9-dimethyl-2,4-yrrolo[2,3-d]pyrimidinedione (80 mg) in methanol (3 ml) was added hydrogen chloride in ether (1 M, 0.5 ml). After stirring at room temperature for 18 hours, the solution was treated with saturated aqueous sodium bicarbonate-sodium chloride solution (10 ml) and extracted with dichloromethane (3x 10 ml). The combined extracts were dried over magnesium sulfate and concentrated under vacuum. The residue was purified by flash chromatography on silica gel eluting with 3% methanol-ethyl acetate to provide (R)-3-(5-hydroxyhexyl)-1,7,9-dimethyl-2,4-pyrrolo[2,3-d]pyrimidinedione (46 mg, 65% yield) as a white powder.

Example 11

Synthesis of (R)-1,9-dimethyl-3-(5-hydroxyhexyl)-2,4-pyrrolo[2,3-d]pyrimidinedione (CT12459)

To a stirring solution of sulfuryl chloride in dichloromethane (1 M, 100 ml) was added propionaldehyde (7 ml, 97 mmol) over 30 seconds. After stirring for 1 hour, methanol (24 ml) was added over 5 minutes. Vigorous gas evolution and refluxing was observed during this addition. After stirring at room temperature for 150 minutes, dichloromethane (75 ml) was removed by distillation. The remaining mixture was treated with saturated aqueous sodium bicarbonate solution (100 ml). The mixture was extracted with ether (100 ml). The extract was dried over magnesium sulfate and concentrated under vacuum to provide 2-chloropropionaldehyde dimethyl acetal (3.7 g, 27% yield).

To a mixture of water (3 ml), tetrahydrofuran (3 ml) and 2-chloropropionaldehyde dimethyl acetal (1.46 g, 10.5 mmol) was added concentrated hydrochloric acid (0.2 ml) and stirred at 80–90° C. for 25 minutes. After cooling to room temperature, sodium acetate (800 mg) was dissolved in the aqueous phase. An aliquot (1 ml) of the upper organic phase was transferred to a stirring mixture of (R)-3-(5-acetoxyhexyl)-6-amino-1-methyluracil (prepared as described for CT12452) (365 mg, 1.29 mmol), sodium acetate minutes. After cooling to room temperature, the mixture was extracted with dichloromethane (2x 15 ml). The combined extracts were dried over magnesium sulfate and concentrated under vacuum. The residue was purified by flash chromatography on silica gel eluting with ethyl acetate to provide (R)-3-(5-acetoxyhexyl)-1,9-dimethyl-2,4-pyrrolo[2,3-]pyrimidinedione (180 mg, 43% yield) as a pink solid.

To a solution of (R)-3-(5-acetoxyhexyl)-1,9-dimethyl-2,4-pyrrolo[2,3-d]pyrimidinedione (90 mg, 0.26 mmol) in methanol (3 ml) was added hydrogen chloride in ether (1 M, 0.5 ml). After stirring at room temperature for 18 hours, the solution was treated with saturated aqueous sodium bicarbonate-sodium chloride solution (10 ml) and extracted with dichloromethane (3x 10 ml). The combined extracts were dried over magnesium sulfate and concentrated under vacuum. The residue was purified by flash chromatography on silica gel eluting with 5% methanol-dichloromethane to provide (R)-1,9-dimethyl-3-(5-hydroxyhexyl)-2,4-pyrrolo[2,3–1]pyrimidinedione (50 mg, 64% yield) as a white solid.

Example 12

Synthesis of (R )3-(5-Hydroxyhexyl)-1-methyl-[1,2,5]thisdiazolo[3,4]pyrimidine-2,4-dione (CT12461)

To a stirring suspension of 5,6-diamino-1-methyluracil (718 mg, 4.6 mmol) (which was prepared as described above for CT12407) and pyridine (3.0 ml) in acetonitrile (10 ml) was added thionyl chloride in one portion. The reaction mixture was stirred at 70° C. for 15 min. After cooling to room temperature, the mixture was poured into 1 N aqueous HCl solution (80 ml) and extracted with ethyl acetate (5x 15 ml). The combined extracts were washed with saturated aqueous sodium chloride solution (15 ml) and dried over magnesium sulfate. Evaporation of the solvent under reduced pressure provided 1-methyl-[1,2,5]thiadiazolo[3,4-]pyrimidine-2,4-dione (480 mg, 57% yield) as a light brown solid.

To a stirring suspension of 1-methyl-[1,2,5]thiadiazolo[3,4-d]pyrimidine-2,4-dione (184 mg, 1.0 mmol) and potassium carbonate (173 mg, 1.25 mmol) in DMF (7.5 ml) was added (R)-5-acetoxhexyl-1-chlorohexane (205 mg, 1.15 mmol) and stirred at 80° C. for 18 hours. After cooling to room temperature, the reaction mixture was quenched by the addition of saturated aqueous sodium chloride solution (15 ml) and the mixture was extracted with ethyl acetate (3x 8 ml). The combined extracts were washed with water (5 ml), with saturated aqueous sodium chloride solution (5 ml) and dried over magnesium sulfate. After evaporation of the solvent under reduced pressure, the crude product was purified by flash chromatography on silica gel eluting with ethyl acetate-hexane (1:1) to provide (R)-3-(5-acetoxyhexyl)-1-methyl-[1,2,5]thiadiazolo[3,4]pyrimidine-2,4-dione (120 mg, 37% yield) as an oil.

To a stirring solution of (R)-3-(5-acetoxyhexyl)-1-methyl-[1,2,5]thiadiazolo[3,4]pyrimidine-2,4-dione (60 mg, 0.184 mmol) in methanol was added an anhydrous solution of hydrogen chloride in ethyl ether (1 M, 1.0 ml, 1.0 mmol) and the mixture was stirred at room temperature for 24 hours. After evaporation of the solvent under reduced pressure, the crude product was purified by flash chromatography on silica gel eluting with ethyl acetate to provide (R)-3-(5-hydroxyhexyl)-1-methyl-[1,2,5]thiadiazolo[3,4]pyrimidine-2,4-dione (CT12461) (38 mg, 73% yield) as an oil.

Example 13

Synthesis of (R)-1-(5-Hydroxyhexyl)-3-methyl-8-azaxanthine (CT12463)

To the stirring solution of (R)-3-(5-acetoxyhexyl)-6-amino-1-methyluracil (prepared as described above for CT12452) (567 mg, 2.0 mmol) in glacial acetic acid (12.5 ml) and water (2.5 ml) at 65° C. was added sodium nitrite (276 mg, 4.0 mmol) in portions. After stirring at 65° C. for 1 hour, the mixture was cooled to 0–5° and the precipitate was filtered. The violet solid was washed with water (2x 10 ml) and then suspended in water (20 ml). The mixture was heated at 65° C. while sodium hydrosulfite was added in portions. After stirring at 65° C. for additional 20 minutes, the solution was treated with glacial acetic acid (15 ml) followed by sodium nitrite (828 mg, 12.0 mmol) in portions. After stirring at 65° C. for an additional 25 min the mixture was cooled to room temperature and then extracted with ethyl acetate (3x 25 ml). The combined extracts were washed with saturated aqueous sodium chloride solution (15 ml) and dried over magnesium sulfate. Evaporation of the solvent under reduced pressure provided (R)-1-(5-Acetoxyhexyl)-3-methyl-8-azaxanthine (400 mg, 65% yield) as an oil.

To a stirring solution of (R)-1-(5-acetoxyhexyl)-3-methyl-8-azaxanthine (150 mg, 0.49 mmol) in methanol (25 ml) was added an anhydrous solution of hydrogen chloride in ethyl ether (1 M, 1.0 ml, 1.0 mmol). After stirring at room temperature for 24 hours, the solvent was evaporated under reduced pressure. The crude product was purified by flash chromatography on silica gel eluting with ethyl acetate-methanol (7:1) to provide (R)-1-(5-hydroxyhexyl)-3-methyl-8-azaxanthine (CT12463) (70 mg, 54 mmol) as a white solid.

Example 14

Synthesis of (R)-3,1-Dimethyl-1-(6-hydroxyhexyl)-8-azaxanthine (CT12464) and (R)-3,8-Dimethyl-1-(5-hydroxyhexyl)-8-azaxanthine(CT12465)

To a suspension of sodium hydride (22 mg, 0.91 mmol) in anhydrous dimethylsulfoxide (4.0 ml) was added (R)-1-(5-acetoxyhexyl)-3-methyl-8-azaxanthine (225 mg, 0.728 mmol). After stirring at room temperature for 30 min, the mixture was treated with methyl iodide (524 mg, 3.64 mmol). After stirring at room temperature overnight, the reaction was quenched by addition of saturated aqueous sodium chloride solution (20 ml) and then extracted with ethyl acetate (3x 15 ml). The combined extracts were washed with water (10 ml), with saturated aqueous sodium chloride solution (10 ml) and dried over magnesium sulfate. TLC showed that there were two products in this mixture. After evaporation of the solvent under reduced pressure, the crude products were purified by flash chromatography on silica gel eluting with ethyl acetate-hexane (1:1) to provide (R)-1-(5-acetoxyhexyl)-3,7-dimethyl-8-azaxanthine (74 mg, 31% yield) followed by (R)-1-(5-acetoxyhexyl)-3,8-dimethyl-8-azaxanthine (66 mg, 28% yield).

To a solution of (R)-1-(5-acetoxyhexyl)-3,7-dimethyl-8-azaxanthine (71 mg, 0.22 mmol) in methanol (15 ml) was added an anhydrous solution of hydrogen chloride in ethyl ether (1 M, 1.0 ml, 1.0 mmol). The mixture was stirred at room temperature for 24 hours and then the solvent was evaporated under reduced pressure. The crude product was purified by flash chromatography on silica gel eluting with ethyl acetate-methanol (7:1) to provide (R)-3,7-dimethyl-1-(5-hydroxyhexyl)-8-azaxanthine (CT12464) (55 mg, 88% yield) as a white solid.

To a solution of (R)-1-(5-acetoxyhexyl)-3,8-dimethyl-8-azaxanthine (66 mg, 0.204 mmol) in methanol (15 ml) was added an anhydrous solution of hydrogen chloride in ethyl ether (1 M, 1.0 ml, 1.0 mmol). The mixture was stirred at room temperature for 24 hours and then the solvent was evaporated under reduced pressure. The crude product was purified by flash chromatography on silica gel eluting with ethyl acetate-methanol (7:1) to provide (R)-3,8-dimethyl-1-(5-hydroxyhexyl)-8-azaxanthine (37 mg, 65% yield) as a white solid.

Example 15

Synthesis of (R)-3,7-Dimethyl-1-(5-hydroxyhexyl)-8-N-methylaminoxanthin (CT12481)

To a stirring suspension of 8-bromo-3-methylxanthine (prepared as described above for CT12440) (12.25 g, 50.0 mmol) and potassium carbonate (8.62 g, 62.5 mmol) in dimethylformamide (150 ml) was added methyl iodide (7.81 g, 55.0 mmol). After stirring overnight at room temperature, the mixture was poured into ice cold water (400 ml) and stirred at 0–5° C. for 1 hour. The precipitate was filtered, rinsed with water (5x 25 ml) and dried under vacuum to provide 8-bromo-3,7-dimethylxanthine (12.10 g, 93% yield) as a beige solid.

To a stirring suspension of sodium hydride (740 mg, 30.8 mmol) in anhydrous dimethylsulfoxide (120 ml) was added 8-bromo-3,7-dimethylxanthine (6.5 g, 25.0 mmol). After stirring at room temperature under argon for 1.5 hours, (R)-5-acetoxyhexyl-1-chlorohexane (4.91 g, 27.5 mmol) was added and the mixture was stirred at 80° C. for 18 hours. After cooling to room temperature, the reaction mixture was quenched by addition of saturated aqueous sodium chloride solution (300 ml) and extracted with ethyl acetate (3x 50 ml). The combined extracts were washed with water (2x 20 ml), with saturated aqueous sodium chloride solution (20 ml) and dried over magnesium sulfate. After evaporation of the solvent under reduced pressure, the crude product was purified by flash chromatography on silica gel eluting with ethyl acetate-hexane (1 :1) to provide (R)-1-(5-acetoxyhexyl)-8-bromo-3, 7-dimethylxanthine (7.38 g, 74% yield) as a colorless oil.

To a solution of (R)-1-(5-acetoxyhexyl)-8-bromo-3,7-dimethylxanthine (5.88 g, 14.7 mmol) in methanol (200 ml) was added a solution of hydrogen chloride in ether (1.0 M, 20 ml). The reaction mixture was stirred at room temperature for 24 hours. Evaporation of the solvent under reduced pressure provided (R)-8-bromo-3,7-dimethyl-1-(5-hydroxyhexyl)xanthine (4.8 g, 91% yield) as a white solid.

(R)-8-Bromo-3,7-dimethyl-1-(5-hydroxyhexyl)xanthine (359 mg, 1.0 mmol) was combined with a solution of methylamine in THF (2.0 M, 8.0 ml) and stirred at room temperature for 7 days. After evaporation of the solvent under reduced pressure, the crude product was purified by flash chromatography on silica gel eluting with ethyl acetate-methanol (4:1) to provide (R)-3,7-dimethyl-1-(5-hydroxyhexyl)-8-N-methylaminoxanthine (258 mg, 83% yield) as a white solid.

Example 16

Synthesis of (R)-3,7-Dimethyl-8-N,N-dimethylamino-1-(5-hydroxyhexyl)-xanthine (CT12485)

(R)-8-Bromo-3,7-dimethyl-1-(5-hydroxyhexyl)xanthine (prepared as described above for CT12481) (180 mg, 0.50 mmol) was combined with a solution of dimethylamine in tetrahydrofuran (2.0 M, 10.0 ml) and stirred at room temperature for 3 days. After evaporation of the solvent under reduced pressure, the crude product was purified by flash chromatography on silica gel eluting with ethyl acetate-methanol (4:1) to provide (R)-3,7-dimethyl-8-N,N-dimethylamino-1-(5-hydroxyhexyl)-xanthine (78 mg, 48% yield) as a white solid.

Example 17

Synthesis of (R)-1-(5-Hydroxyhexyl)-3-methyl-8-methylsulfanylxanthine(CT12490)

To a stirring solution of (R)-1-(5-acetoxyhexyl)-8-bromo-7-ethoxymethyl-3-methylxanthine (prepared as described above for CT12440) (1.77 g, 4.0 mmol) in ethanol (100 ml) was added sodium sulfide (4.48 g, 80 mmol). The reaction mixture was stirred at 90° C. for 1 hour. After evaporation of the solvent under reduced pressure, the crude product was purified by flash chromatography on silica gel eluting with ethyl acetate-methanol (7:1) to provide (R)-1-(5-acetoxyhexyl)-7-ethoxymethyl-8-mercapto-3-methylxanthine. This product was dissolved in methanol (100 ml). A solution of hydrogen chloride in ether (1.0 M, 1.0 ml) was added and stirred at room temperature for 24 hours. After evaporation of the solvent under reduced pressure. The crude product was purified by flash chromatography on silica gel eluting with ethyl acetate-methanol (4:1) to provide (R)-1-(5-hydroxyhexyl)-7-ethoxymethyl-8-mercapto-3-methylxanthine (610 mg, 51% yield) as a white solid.

To a stirring suspension of (R)-1-(5-hydroxyhexyl)-7-ethoxymethyl-8-ercapto-3-methylxanthine (62.0 mg, 0.174 mmol) and potassium carbonate (42 mg, 0.30 mmol) in acetonitrile (3.4 ml) was added methyl iodide (44 mg, 0.3 mmol). The reaction mixture was stirred at room temperature for 3 hours. After evaporation of the solvent under reduced pressure. The crude product was purified by flash chromatography on silica gel eluting with ethyl acetate-hexane (3:1) to provide (R)-7-ethoxymethyl-1-(5-hydroxyhexyl)-3-methyl-8-methylsulfanylxanthine (58 mg, 89% yield) as a white solid.

To a solution of (R)-7-ethoxymethyl-1-(5-hydroxyhexyl)-3-methyl-8-methylsulfanylxanthine (20 mg, 0.054 mmol) in ethanol (1.9 ml) was added concentrated hydrochloric acid (0.10 ml). The reaction mixture was stirred at 80° C. for 24 hours. After evaporation of the solvent under reduced pressure, the crude product was purified by flash chromatography on silica gel eluting with ethyl acetate-methanol (7:1) to provide (R)-1-(5-hydroxyhexyl)-3-methyl-8-methylsulfanylxanthine (12 mg, 70% yield) as a white solid.

Example 18

Synthesis of (S)-1-(5-Hydroxyhexyl)-7-benzyl-3-methylxanthine (CT22404)

A 10% aqueous sodium hydroxide solution (10 ml) was added to a suspension of 3-methylxanthine (4.15 g) in methanol (25 ml) and the mixture was stirred for 1 hour at 70° C. Benzyl bromide (4.275 g, 2.97 ml) was added dropwise at 70° C. and the mixture was stirred at 70–60° C. for an additional 5 hours. After cooling to room temperature, the mixture was treated with water (50 ml). The precipitate was filtered, dissolved in 1 N aqueous sodium hydroxide solution (50 ml) and the solution was acidified to pH 4–5 with concentrated hydrochloric acid. The precipitate was filtered and washed with water (3x 20 ml) to provide 7-benzyl-3-methylxanthine (4.45 g).

To a stirring suspension of 7-benzyl-3-methylxanthine (0.512 g, 2 mmol) in dimethyl sulfoxide (10 ml) was added 95% sodium hydride (50.5 mg, 2.0 mmol) in one portion. After stirring for 30 minutes, (S)-5-acetoxy-1-bromohexane (0.490 g, 2.2 mmol) was added neat. After stirring at room temperature for 12 hours, the reaction was quenched by addition of water (50 ml) and extracted with ethyl acetate (3x 50 ml). The combined extracts were washed with saturated aqueous sodium bicarbonate solution (50 ml), with saturated aqueous sodium chloride solution (50 ml) and dried over magnesium sulfate. Evaporation of the solvent under reduced pressure gave a residue which was purified by flash chromatography on silica gel eluting with ethyl acetate to give (S)-1-(5-acetoxyhexyl)-7-benzyl-3-methylxanthine (0.700 g).

A solution of (S)-1-(5-acetoxyhexyl)-7-benzyl-3-methylxanthine (350 mg) in methanol (10 ml) was treated with 1 M hydrogen chloride in ether (5 ml). After stirring at room temperature for 12 hours, the solvent was evaporated under reduced pressure. The residue was dissolved in dichloromethane (100 ml). The solution was washed with saturated aqueous sodium bicarbonate solution (30 ml), dried over anhydrous magnesium sulfate and concentrated under reduced pressure to give (S)-1-(5-hydroxyhexyl)-7-benzyl-3-methylxanthine (270 mg).

Example 19

Synthesis of (S)-3,7-Dimethyl-1-(5-hydroxyhexyl)-8-zaxanthine (CT22464) and (S)-3,8-Dimethyl-1-(5-hydroxyhexyl)-8-zaxanthine (CT22465)

(S)-3,7-Dimethyl-1-(5-hydroxyhexyl)-8-azaxanthine (CT22464) and (S)-3,8-dimethyl-1-(5-hydroxyhexyl)-8-azaxanthine (CT22465) were synthesized according to the methods described for (R)-3,7-dimethyl-1-(5-hydroxyhexyl)-8-azaxanthine (CT12464) and for (R)-3,8-dimethyl-1-(5-hydroxyhexyl)-8-azaxanthine (CT12465) but using (S)-5-acetoxy-1-chlorohexane in place of (R)-5-acetoxy-1-chlorohexane.

Example 20

Synthesis of (R)-3-N-biotinyl-6-aminohexyl)-1-(5-hydroxyhexyl)-7-methylxanthin (CT12460)

a) N-1-BOC-6-amino-1-bromohexane was first prepared by adding di-tert-butyldicarbonate (3.675 g, 16.4 mmol) to a solution of 6-aminohexan-1-ol (1.6 g, 13.66 mmol) in 10% aqueous sodium hydroxide solution (40 m)). After stirring for 4 hours, the mixture was treated with water (150 ml) and extracted with ethyl acetate (4x 50 ml). The combined extracts were washed with water (2x 50 ml), dried over anhydrous magnesium sulfate, and concentrated under reduced pressure. The residue was purified by a flash chromatography on silica gel eluting with 20% methanol/dichloromethane to provide N-1-BOC-6-amino-hexan-1-ol (2.4 g).

A solution of bromine (1.60 g, 10 mmol) in dichloromethane (10 ml) was added to a solution of triphenyl phosphine (2.62 g, 10 mmol) and triethylamine (1.01 g, 10 mmol) in dichloromethane (10 ml) at 0° C. After stirring at 0° C. for 30 minutes, a solution of N-t-BOC-6-amino-hexan-1-ol (2.4 g) in dichloromethane (10 ml) was added dropwise. After stirring for 2 hours, the mixture was concentrated under reduced pressure. The residue was purified by flash chromatography eluting with 20%ethyl acetate/hexane to provide N-t-BOC-6-amino-1-bromohexane (2.5 g).

b) Then, (R)-1-(5-Acetoxyhexyl)-7-methylxanthine was prepared by heating a mixture of N-benzylurea (100 g), cyanoacetic acid (62.37 g) and acetic anhydride (210 ml) at 70–80° C. for 2 hours. Upon cooling, crystals of open chain cyanoacetyl derivative began to precipitate. The mixture was stirred with ether (500 ml) and then cooled in an ice-water bath for 2 hours. The precipitate was filtered, washed with ether and dried in air. This solid was suspended in a mixture of water (200 ml) and ethanol (100 ml). The mixture was heated at 85° C. while 1046 aqueous sodium hydroxide solution (50 ml) was gradually added. The cyanoacetyl derivative dissolved completely and a new solid precipitated gradually. The mixture was heated at 85° C. for 30 minutes. After cooling to room temperature, the mixture was made slightly acidic by addition of concentrated hydrochloric acid solution. The precipitate was filtered, washed with water and dried in air to provide 6-amino-1-benzyluracil (117 g).

6-Amino-1-benzyl-5-bromouracil. A solution of bromine (33.17 ml) in acetic acid (300 ml) was added slowly to a solution of 6-amino-1-benzyluracil and anhydrous sodium acetate (93.29 g) in acetic acid (300 ml) and stirred for 6 hours. The reaction mixture was cooled in ice-cold water. The precipitate was filtered and dried under vacuum to provide 6-amino-1-benzyl-5-bromouracil (134.0 g).

6-Amino-1-benzyl-5-bromouracil (134 g) was stirred with 40% aqueous methylamine solution (750 ml) for 24 hours. After cooling to 5° C., the precipitate was filtered and dried under suction to provide 6-amino-1-benzyl-5-methylaminouracil (55 g).

6-Amino-1-benzyl-5-methylaminouracil (11 g, 43 mmol) was added to a suspension of sodium hydride (1.032 mg, 43 mmol) in anhydrous dimethylsulfoxide (75 ml). After stirring for 30 minutes, (R)-5-acetoxy-1-chlorohexane (7.675 g, 43 mmol) was added. The mixture was heated at 70–80° C. for 12 hours. After cooling to room temperature, the reaction was quenched by the addition of water (150 ml) and extracted with ethyl acetate (3x 125 ml). The combined extracts were washed with water (2x 50 ml), with saturated aqueous sodium chloride solution (50 ml), dried over magnesium sulfate and concentrated under reduced pressure. The residue was purified by flash chromatography on silica gel eluting with ethyl acetate to provide (R)-3-(5-acetoxyhexyl)-6-amino-1-benzyl-5-methylaminouracil (7.89 g).

A mixture of (R)3-(5-acetoxyhexyl)-6-amino-1-benzyl-5-methylaminouracil (7.89 g) and formic acid (200 ml) was heated at reflux for 1 hour. The mixture was concentrated under reduced pressure to give crude (R)-3-(5-acetoxyhexyl)-6-amino-1-benzyl-5-N-methylformamidouracil that was used in the next step without further purification.

To a solution of (R)-3-(5-acetoxyhexyl)-6-amino-1-benzyl-5-N-methylformamidouracil, ethanol (125 ml), water (125 ml) and 30% aqueous ammonium hydroxide solution (30 ml) was added 10% palladium on carbon (3.5 g) and hydrogenated at 70 psi for 12 hours. The mixture was filtered through a pad of celite and the filtrate was concentrated under reduced pressure to provide (R)-3-(5-acetoxyhexyl)-6-amino-S-N-methylformamidouracil (7.1 g).

p-Toluenesulfonic acid (1 g) was added to a solution of (R)-3-(5-acetoxyhexyl)-6-amino-5-N-methylformamidouracil (7.19) in formamide (150 ml) and the mixture was heated at reflux for 3 hours. After evaporation of the formamide, the residue was purified by flash chromatography on silica gel eluting with 10% methanol-dichloromethane to provide (R)-1-(5-Acetoxyhexyl)-7-methylxanthine (3.8 g).

c) The (R)-1-(5-Acetoxyhexyl)-7-methylxanthine (1.285 g, 4.2 mmol) was then added to a suspension of sodium hydride (120 mg, 4.2 mmol) in anhydrous OMSO (15 ml). After stirring far 30 minutes, the N-1-BOC-6-amino-1-bromohexane (1.21 g, 4 mmol) was added and stirred. After stirring for 12 hours, the reaction was quenched by the addition of water (45 ml) and extracted with ethyl acetate (3x 35 ml). The combined extracts were washed with water (2x 25 ml), with saturated aqueous sodium chloride solution (25 ml), dried over anhydrous magnesium sulfate and concentrated under reduced pressure. The residue was purified by flash chromatography on silica gel eluting with ethyl acetate to provide (R)-1-(5-acetoxyhexyl)-3-(N-tert-butyloxycarbonyl-6-aminohexyl)-7-methylxanthine (1.37 g).

Trifluoroacetic acid (30 ml) was added to a solution of (R)-1-(5-acetoxyhexyl)-3-(N-1-butyloxycarbonyl-6-aminohexyl)-7-methylxanthine (1.37 g) in dichloromethane (30 ml). After stirring at room temperature for 1 hour, the mixture was concentrated under reduced pressure. The residue was dissolved in dichloromethane (50 ml). The solution was washed with saturated aqueous sodium bicarbonate solution (20 ml), with water (20 ml), with saturated aqueous sodium chloride solution (20 ml), dried over anhydrous magnesium sulfate and concentrated under reduced pressure to provide (R)-1-(5-acetoxyhexyl)-3-(6-aminohexyl)-7-methylxanthine (1.073 g).

Disopropylcarbodiimide (113.5 mg, 0.55 mmol) was added to a solution of biotin (122 mg, 0.5 mmol), (R)-1-(5-acetoxyhexyl)-3-(6-aminohexyl)-7-methylxanthine(227 mg, 0.5 mmol) and 4-N,N-dimethylaminopyridine (73.3 mg, 0.6 mmol) in dimethylformamide. After stirring at room temperature for 6 hours, dimethylformamide was evaporated under reduced pressure. The residue was purified by flash chromatography on silica gel eluting with 20% methanol/ethyl acetate to provide (R)-1-(5-acetoxyhexyl)-3-(N-biotinyl-6-aminohexyl)-7-methylxanthine (110 mg).

A solution of (R)-1-(5-acetoxyhexyl)-3-(N-biotinyl-6-aminohexyl)-7-methylxanthine (110 mg) in methanol (10 ml) was treated with one drop of concentrated hydrochloric acid solution. After stirring al room temperature for 14 hours, the mixture was treated with 2M solution of ammonia in methanol (3 ml) and concentrated under reduced pressure. The residue was purified by flash chromatography on silica gel eluting with 20methano/dichloromethane to provide (R)-3-(N-biotinyl-6-aminohexyl)-1-(5-hydroxyhexyl)-7-methylxanthine (CT12460) (66 mg).

Example 21

Synthesis of (R)-3-N-biotinyl-2-aminoethyl)-1-5-hydroxyhexyl)-7-methylxanthine (CT13410)

(R)-3-N-Biotinyl-2-aminoethyl)-1-(5-hydroxyhexyl)-7-methylxanthine (CT13410) was prepared according to the method described above for (R)-3-(N-biotinyl-6-aminohexyl)-1-(5-hydroxyhexyl)-7-methylxanthine (CT12460) but using (R)-1-(5-acetoxyhexyl)-3-(2-aminoethyl)-7-methylxanthine in place of (R)-145-acetoxyhexyl)-3-(6-aminohexyl)-7-methylxanthine. The (R)-1-(5-acetoxyhexyl)-3-(2-aminoethyl)-7-methylxanthine was prepared according to the following procedure.

Di-tert-butyldicarbonate (10.912 g, 50 mmol) was added to a solution of ethanolamine (3.054 g, 50 mmol) in 10% aqueous sodium hydroxide solution (40 ml) and stirred for 4 hours. The mixture was treated with water (150 ml) and extracted with ethyl acetate (4x 50 ml). The combined extracts were washed with water (2x 50 ml), dried over magnesium sulfate and concentrated under reduced pressure to provide N-1-BOC-ethanolamine (6.8 g).

Triphenylphosphine (11.54 g) was added in portions to a solution of carbon tetrabromide (14.6 g) and N-t-BOC-ethanolamine (6.44 g) in dichloromethane (300 ml). After stirring for 4 hours, the mixture was concentrated under reduced pressure to half its volume, diluted with hexane and filtered. The filtrate was concentrated under vacuum and the residue was purified by flash chromatography on silica gel eluting with hexane to provide N-t-BOC-2-amino-1-bromoethene (4.6 g).

(R)-1-(5-Acetoxyhexyl)-7-methylxanthine (1.848 g, 6 mmol) (prepared as described for CT12460) was added to a suspension of sodium hydride (144 mg, 6 mmol) in anhydrous DMSO (15 ml). After stirring for 30 minutes, N-1-BOC-2-amino-1-bromoethane (1.344 g, 6 mmol) was added. After stirring for 12 hours, the reaction was quenched by the addition of water (45 ml) and extracted with ethyl acetate (3x 35 ml). The combined extracts were washed with water (2x 25 ml), with saturated aqueous sodium chloride solution (25 ml), dried over magnesium sulfate and concentrated under reduced pressure. The residue was purified by flash chromatography on silica gel eluting with ethyl acetate to provide (R)-1-(5-acetoxyhexyl)-3-(N-t-BOC-2-aminoethyl)-7-melhylxanthine (1.08 g).

Trifluoroacetic acid (30 ml) was added to a solution of (R)-1-(5-acetoxyhexyl)-3-(N-1-BOC-2-aminoethyl)-7-methylxanthine (1.08 g) in dichloromethane (30 ml). After stirring at room temperature for 1 hour, the mixture was concentrated under reduced pressure. The residue was dissolved in dichloromethane (50 ml). The solution was washed with saturated aqueous sodium bicarbonate solution (20 ml), with water (20 ml), with saturated aqueous sodium chloride solution (20 ml), dried over anhydrous magnesium sulfate and concentrated under reduced pressure to provide (R)-1-(5-acetoxyhexyl)-3-(2-aminoethyl)-7-methylxanthine (0.72 g).

Example 22

Synthesis of (R)-1-5-N,N-Dimethylaminohexyl)-3,7-dimethylxanthine(CT11568)

A solution of (S)-1-(5-hydroxyhexyl)-3,7-dimethylxanthine (Klein, J. P.; Leigh, A, J.; Michnick, J.; Kumar, A. M.; Underiner, G. E. Asymmetric Synthesis of Chiral Secondary Alcohols, U.S. Pat. No. 5,629,423 (May 13, 1997)) (14 g, 50 mmol) and triethylamine (14 ml) was cooled to 0° C. in dichloromethane (200 ml) and methanesulfonyl chloride (5.80 ml. 75 mmol) was added slowly at 0° C. After stirring for an additional 4 hours at 0° C., the reaction was quenched by the addition of water and extracted with dichloromethane (4x 150 ml). The combined extracts were washed with saturated aqueous sodium chloride solution, dried over anhydrous magnesium sulfate and concentrated under reduced pressure to provide (S)-1-(5-methanesulfonyloxyhexyl)-3,7-dimethylxanthine (19.6 g).

Sodium azide (7.11 g, 0.1 mol) was added to a solution of (S)-1-(5-methanesulfonyloxyhexyl)-3,7-dimethylxanthine (19.6 g, 54 mmol) in dimethylsulfoxide (100 ml) and stirred at 50° C. for 12 hours. The mixture was treated with water (200 ml) and extracted with ethyl acetate (3x 100 ml). The combined extracts were washed with water (125 ml), with saturated aqueous sodium chloride solution (150 ml), dried over magnesium sulfate and concentrated under reduced pressure. The residue was purified by flash chromatography on silica gel eluting with ethyl acetate to give (R)-1-(5-azidohexyl)-3,7-dimethylxanthine (13 g).

A solution of the (R)-1-(5-azidohexyl)-3,7-dimethylxanthine (620 mg) in ethanol (25 ml) was hydrogenated at 70 psi of hydrogen gas in presence of 10% palladium on carbon (150 mg) for 12 hours. After filtration to remove the catalyst, the filtrate was concentrated under reduced pressure to provide (R)-1-(5-aminohexyl)-3,7-dimethylxanthine.

A solution of sodium cyanoborohydride (75 mg) and zinc chloride (82 mg) in methanol (15 ml) was added to a solution of (R)-1-(5-aminohexyl)-3,7-dimethylxanthine (279 mg) and 37% aqueous formaldehyde (0.5 ml) in methanol (5 ml). After stirring for 2 hours, the reaction was quenched by addition of 0.1 N aqueous sodium hydroxide solution (10 ml). After evaporation of most of the methanol under reduced pressure, the mixture was extracted with dichloromethane (5x 40 ml). The combined extracts were washed with water (50 ml), with saturated aqueous sodium chloride solution, dried over anhydrous magnesium sulfate and concentrated under reduced pressure. The residue was purified by flash chromatography on silica gel eluting with 5% aqueous ammonium hydroxide, 35% methanol and 60% dichloromethane to give (R)-1-(5-N,N-dimethylaminohexyl)-3,7-dimethylxanthine (CT11558) (150 mg).

Example 23

Synthesis of (S)-1-(5-N,N-Dimethylaminohexyl)-3,7-dimethylxanthine(CT21558).

(S)-1-(5-N,N-Dimethylaminohexyl)-3,7-dimethylxanthine (CT21558) was prepared according to the method described for (R)-1-(5-N,N-dimethylaminohexyl)-3,7-dimethylxanthine (CT11558) but using (R)-1-(5-hydroxyhexyl)-3,7-dimethylxanthine in place of (S)-1-(5-hydroxyhexyl)-3,7-imethylxanthine.

Example 24

Synthesis of (R)-1-(5-Acetamidohexyl)-3,7-dimethylxanthine (CT12538)

Isobutylchloroformate (341 mg, 2.5 mmol) was added slowly to a solution of acetic acid (146 mg, 2.5 mmol) and triethylamine (252.75 mg, 2.5 mmol) in dichloromethane (20 ml) at −15° C. After warming to room temperature over 15 minutes, a solution of (R)-1-(5-aminohexyl)-3,7-dimethylxanthine (prepared as described for CT11558) (558 mg, 2 mmol) in dichloromethane (10 ml) was added. After stirring al room temperature for 12 hours, the mixture was concentrated under reduced pressure. The residue was purified by flash chromatography on silica gel eluting with 13% methanol-ethyl acetate to provide (R)-1-(5-acetamidohexyl)-3,7-dimethylxanthine (CT12538) (380 mg).

Example 25

Synthesis of (R)-145-Cyanohexyl)-3,7-dimethylxanthine (CT16575).

Potassium cyanide (280 mg, 4.30 mmol) was added to a solution of (5)-1-(5-methanesulfonyloxyhexyl)-3,7-dimethylxanthine (prepared as described for CT11558) (770 mg, 2.15 mmol) in dimethylsulfoxide (10 ml). After heating at 50° C. for 24 hours, the mixture was poured into water (50 ml) and extracted with ethyl acetate (3x 50 ml). The combined extracts were washed with water (40 ml), saturated aqueous sodium chloride solution (40 ml), dried over anhydrous magnesium sulfate, and concentrated under reduced pressure. The residue was purified by flash chromatography on silica gel eluting with ethyl acetate to provide (R)-1-(5-cyanohexyl)-3,7-dimethylxanthine (CT16575) (280 mg).

Example 26

Synthesis of (R)-8-Aminomethyl-1-(5-yanohexyl)-3-methylxanthine (CT 30289)

To a suspension of (5)-1-(5-acetoxyhexyl)-8-hydroxymethyl-3-methylxanthine (prepared as described for synthesis of (R)-1-(5-hydroxyhexyl)-8-aminomethyl-3,7-dimethylxanthine libraries) (10.5 g, 31 mmol) and potassium carbonate (8.6 g, 62 mmol) in dimethylformamide (100 ml) was added benzyl bromide (8.67 g, 39 mmol). After stirring at room temperature overnight, the mixture was poured into ice water (250 ml) and stirred at 0–5° C. for 1 hour. The precipitate was filtered, rinsed with water (4x 50 ml) and dried under vacuum to provide (S)-1-(5-acetoxyhexyl)-7-benzyl-8-hydroxymethyl-3-methylxanthine (9.8 g, 74% yield).

To a solution of thionyl chloride (100 ml) was added (S)-1-(5-acetoxyhexyl)-7-benzyl-8-hydroxymethyl-3-methylxanthine (9.8 g, 22.9 mmol). After stirring for 3 hours at room temperature, unreacted thionyl chloride was evaporated under reduced pressure. The residual oil was purled by flash chromatography on silica gel eluting with ethyl acetate-hexane (1:1) to afford (S)-1-(5-acetoxyhexyl)-7-benzyl-8-chloromethyl(-3-methylxanthine (8.7 g, 85% yield) as a colorless oil.

To a solution of (S)-1-(5-acetoxyhexyl)-7-benzyl-8-chloromethyl-3-methylxanthine (8.7 g, 19.5 mmol) was added a solution of hydrogen chloride in ether (1.0 M, 20 ml). After stirring at room temperature for 24 hours, the solvent was evaporated under reduced pressure to give (S)-1-(5-hydroxyhexyl)-7-benzyl-8-chloromethyl-3-methylxanthine (7.0 g, 89% yield) as a white solid.

A suspension of (S)-1-(5-hydroxyhexyl)-7-benzyl-8-chloromethyl-3-methylxanthine (2.0 g, 5.0 mmol) and sodium azide (1.62 g, 25 mmol) in methyl sulfoxide (15 ml) was stirred at 60° C. overnight. The reaction mixture was quenched by addition of water (30 ml) and extracted with ethyl acetate (3×25 ml). The combined extracts were washed with water (2×10 ml), with saturated aqueous sodium chloride solution (25 ml), dried over magnesium sulfate, and concentrated under reduced pressure. The crude product was purified by flash chromatography on silica gel eluting with ethyl acetate to provide (S)-1-(5-hydroxyhexyl)-7-benzyl-8-azidomethyl-3-methylxanthine (1.7 g, 83% yield) as a colorless oil.

To a solution of (S)-1-(5-hydroxyhexyl)-7-benzyl-8-azidomethyl-3-methylxanthine (1.7 g, 1.65 mmol) in ethanol (100 ml) was added 10% palladium on carbon catalyst (0.6 g). The mixture was treated with hydrogen gas (50 psi) on a Parr shaker for 18 hours. Removal of the catalyst by filtration and evaporation of the solvent under reduced pressure provided (S)-1-(5-hydroxyhexyl)-7-benzyl-8-aminomethyl-3-methylxanthine (1.6 g, 100% yield).

To a solution of (S)-1-(5-hydroxyhexyl)-7-benzyl-8-aminomethyl-3-methylxanthine (1.6 g, 4.1 mmol) was added triethylamine (1.26 g, 12.5 mmol) and di-tert-butyl dicarbonate (1.63 g, 7.5 mmol). After stirring at room temperature overnight, the solvent was evaporated under reduced pressure. The crude product was purified by flash chromatography on silica gel eluting with ethyl acetate to provide (S)-1-(5-hydroxyhexyl)-7-benzyl-8-(N-BOC-aminomethyl)-3-methylxanthine (1.5 g, 75% yield) as a white solid.

To a solution of (S)-1-(5-hydroxyhexyl)-7-benzyl-8-(N-BOC-aminomethyl)-3-methylxanthine (0.6 g, 1.24 mmol) in ethanol (60 ml) was added 10% palladium on carbon catalyst (0.5 g). The mixture was treated with hydrogen gas (50 psi) on a Parr shaker for 18 hours. Removal of the catalyst by filtration and evaporation of the solvent under reduced pressure provides (S)-1-(5-hydroxyhexyl)-8-(N-BOC-aminomethyl)-3-methylxanthine (0.4 g, 82% yield) as a white solid.

To a solution of (S)-1-(5-hydroxyhexyl)-8-(N-BOC-aminomethyl)-3-methylxanthine (0.4 g, 1.0 mmol) and 4-dimethylaminopyridine (0.61 g, 5.0 mmol) in chloroform (15 ml) was added methanesulfonic anhydride (0.35 g, 2.0 mmol). After stirring at room temperature overnight, the solvent was evaporated under reduced pressure. A mixture of ethyl acetate and water (1:1) (100 ml) was added. The organic phase was washed with aqueous potassium hydrogen sulfate solution (0.1 N) to pH=2–3, with water (2×15 ml), with saturated aqueous sodium chloride solution (15 ml), dried over magnesium sulfate, and concentrated under reduced pressure to afford (S)-1-(5-methanesulfonyloxyhexyl)-8-(N-BOC-aminomethyl)-3-methylxanthine (0.47 g, 100% yield) as a white solid.

A suspension of (S)-1-(5-methanesulfonyloxyhexyl)-8-(N-BOC-aminomethyl)-3-methylxanthine (0.47 g, 1.0 mmol) and potassium cyanide (0.39 g, 6.0 mmol) in dimethylsulfoxide (8.0 ml) was stirred at 60° C. overnight. The reaction was quenched by addition of water (30 ml) and extracted with ethyl acetate (3×15 ml). The combined extracts were washed with water (2×15 ml), saturated aqueous sodium chloride solution (15 ml), dried over magnesium sulfate, and concentrated under reduced pressure. The crude product was purified by flash chromatography on silica gel eluting with 15% methanol-ethyl acetate to give (R)-1-(5-cyanohexyl)-8-(N-BOC-aminomethyl)-3-methylxanthine (0.25 g, 62% yield) as an oil.

To a 50% solution of trifluoroacetic acid in dichloromethane (15 ml) was added (R)-1-(5-cyanohexyl)-8-(N-BOC-aminomethyl)-3-methylxanthine (0.21 g, 0.52 mmol). After stirring at room temperature for 3 hours, the solvent and excess reagent were evaporated under reduced pressure. The residue was treated with ammonia-methanol solution (2.0 M, 10 ml) and stirred for 1 hour. After concentration under reduced pressure, the crude product was purified by flash chromatography on silica gel eluting with ammonium hydroxide (37% in water)-methanol-ethyl acetate mixture (1:10:5) to provide (R)-8-aminomethyl-1-(5-cyanohexyl)-3-methylxanthine (0.06 g, 38% yield) as a white solid.

Example 27

Synthesis of (R)-1-(5-Dimethylaminohexyl)-8-aminomethyl-3-methylxanthine (CT30280)

A suspension of the (S)-1-(5-methanesulfonyloxyhexyl)-8-(N-BOC-aminomethyl)-3-methylanthine (prepared as described for CT30289) (0.82 g, 1.80 mmol) and sodium azide (0.56 g, 8.6 mmol) in dimethylsulfoxide (5.0 ml) was stirred at 60° C. overnight. The reaction was quenched by addition of water (20 ml) and extracted with ethyl acetate (3×15 ml). The organic phase was washed with water (2×15 ml), with saturated aqueous sodium chloride solution (15 ml), dried over magnesium sulfate, and concentrated under reduced pressure to afford (R)-1-(5-azidohexyl)-8-(N-BOC-aminomethyl)-3-methylxanthine (0.7 g, 90% yield) as a white solid.

To a solution of (R)-1-(5-azidohexyl)-8-(N-BOC-aminomethyl)-3-methylxanthine (0.7 g, 1.6 mmol) in ethanol (40 ml) was added 10% palladium on carbon catalyst (0.3 g). The mixture was treated with hydrogen gas (50 psi) on a Parr shaker for 18 hours. Removal of the catalyst by filtration and evaporation of the solvent under reduced pressure provided (R)-1-(5-aminohexyl)-8-(N-BOC-aminomethyl)-3-methylxanthine (0.5 g, 77% yield) as a white solid.

To a solution of (R)-1-(5-aminohexyl)-8-(N-BOC-aminomethyl)-3-methylxanthine (0.4 g, 1.0 mmol) in methanol (10 ml) was added formaldehyde (37% in water) (0.4 ml) followed by sodium cyanoborohydride (0.1 g, 1.5 mmol). After stirring at room temperature for 1 hour, the solvent was evaporated under reduced pressure. The crude product was purified by flash chromatography on silica gel eluting with ammonium hydroxide (37% in water)-methanol-ethyl acetate mixture (1:5:10) to give (R)-1-(5-dimethylaminohexyl)-8-(N-BOC-aminomethyl)-3-methylxanthine (0.20 g, 47% yield) as an oil.

To a 50% solution of trifluoroacetic acid in dichloromethane (15 ml) was added (R)-1-(5-dimethylaminohexyl)-8-(N-BOC-aminomethyl)-3-methylxanthine (0.16 g, 0.38 mmol). After stirring at room temperature for 3 hours, the solvent and excess reagent were evaporated under reduced pressure. The residue was treated with ammonia-methanol solution (2.0 M, 10 ml) and stirred for 1 hour. Concentration under reduced pressure gave the crude product which was purified by flash chromatography on silica gel eluting with ammonium hydroxide (37% in water)-methanol-ethyl acetate (2:10:1). (R)-1-(5-Dimethylaminohexyl)-8-aminomethyl-3-methylxanthine (0.062 g, 50% yield) was obtained as an oil.

Example 28

Synthesis of (R)-1-(5-Dimethylaminohexyl)-8-N-methylaminomethyl-3-methylxanthine (CT 30274)

To a solution of (S)-1-(5-hydroxyhexyl)-7-benzyl-8-chloromethyl-3-methylxanthine (prepared as described for the synthesis of CT 30289) (2.3 g, 5.68 mmol) in methanol (50 ml) was added methylamine (40% in water, 50 ml). After stirring at room temperature for 2 hours, the solvent and excess reagent were evaporated under reduced pressure. A solution of triethylamine and ethanol (1:4) (100 ml) was added and then evaporated under reduced pressure to give (S)-1-(5-hydroxyhexyl)-7-benzyl-8-methylaminomethyl-3-methylxanthine as a white powder.

To a solution of (S)-1-(5-hydroxyhexyl)-7-benzyl-8-methylaminoethyl-3-methylxanthine in methanol (35 ml) was added triethylamine (1.44 g, 14.2 mmol) followed by di-tert-butyl dicarbonate (1.85 g, 8.5 mmol). After stirring at room temperature overnight, the mixture was concentrated under reduced pressure. The residue was treated with water (50 ml) and extracted with ethyl acetate (3×50 ml). The combined extracts were washed with water (2×25 ml), saturated aqueous sodium chloride solution (25 ml), dried over magnesium sulfate, and concentrated under reduced pressure. The crude product was purified by flash chromatography on silica gel eluting with ethyl acetate-hexane (1:1) to provide (S)-1-(5-hydroxyhexyl)-7-benzyl-8-(N-BOC-methylaminomethyl)-3-methylxanthine (2.1 g, 76% yield) as a white solid.

(R)-1-(5-Dimethylaminohexyl)-8-N-methylaminomethyl-3-methylxanthine (CT 30274) was synthesized from (S)-1-(5-hydroxyhexyl)-7-benzyl-8-(N-BOC-methylaminomethyl)-3-methylxanthine according to the method above for the synthesis of (R)-1-(5-dimethylaminohexyl)-8-aminomethyl-3-methylxanthine (CT30280) from (S)-1-(5-hydroxyhexyl)-7-benzyl-8-(N-BOC-aminomethyl)-3-methylxanthine.

Example 29

7-substituted (R)-1-(5-hydroxyhexyl)-3-methylxanthine Libraries a) Brominated polystyrene was synthesized using a method described in Farrall, M. J., Frechet, M. J. *J. Org. Chem.*, 1976, 41, 3877–82. Thallium trifluoroacetate (700 mg, 1.3 mmol) was added to a suspension of polystyrene resin (10 g) in carbon tetrachloride (150 ml). After stirring in the dark for 30 minutes, a solution of bromine (6.8 g, 42 mmol) in carbon tetrachloride (10 ml) was added slowly. After stirring at room temperature in the dark for 1 hour, the reaction mixture was heated to reflux for 90 minutes. Filtration followed by washing of the solid with carbon tetrachloride, acetone, acetone-water (2:1), acetone, benzene and methanol (20 ml each) and drying under vacuum provided brominated polystyrene (13.6 g).

b) Chlorosilylated polystyrene was synthesized using a method analogous to that described in Farrall, M. J., Frechet, M. *J. Org. Chem.*, 1976, 41, 3877–82. After stirring a suspension of brominated polystyrene (8 g) in anhydrous tetrahydrofuran (90 ml) for 30 minutes, a solution of 2.7 M n-butyllithium in heptane (24 ml, 64 mmol). After stirring at 60° C. for 3 hours, the reaction mixture was cooled to room temperature and the supernant was removed by decantation. After cooling to −45° C., anhydrous tetrahydrofuran (30 ml) was added followed by dichlorodiisopropylsilane (11.85 g, 64 mmol). The reaction mixture was warmed to room temperature and shaken for 12 hours. Filtration followed by washing of solid with dry tetrahydrofuran (30 ml) under positive pressure of argon and drying under vacuum afforded chlorosilylated polystyrene (9.24 g).

c) To a stirring suspension of 7-benzyl-3-methylxanthine (25.6 g, 100 mmol) (which had been prepared as described for CT22404 of Example 18) in dimethylsulfoxide (200 ml) was added 95% sodium hydride (3.2 g, 133 mmol) in portions over 10 minutes. After stirring for 30 minutes, (R)-5-acetoxy-1-chlorohexane (19.63 g, 110 mmol) was added neat. After heating at 70–80° C. for 6 hours, the reaction mixture was quenched by addition of water (500 ml) and extracted with ethyl acetate (3×150 ml). The combined extracts were washed with water (150 ml), saturated aqueous sodium chloride solution (150 ml) and dried over magnesium sulfate. Evaporation of the solvent under reduced pressure gave a residue which was purified by flash chromatography on silica gel eluting with 20% hexane/ethyl according to give (R)-1-(5-acetoxyhexyl)-7-benzyl-3-methylxanthine (33.7 g).

d) Potassium carbonate (30 g) was added to a solution of (R)-1-(5-acetoxyhexyl)-7-benzyl-3-methylxanthine (33.7 g, 84.7 mmol) in methanol (400 ml) and refluxed for 12 hours. After concentration under reduced pressure, the residue was partitioned between ethyl acetate (500 ml) and water (300 ml). The organic layer was washed with water (100 ml), dried over anhydrous magnesium sulfate, and concentrated under reduced pressure to provide (R)-7-benzyl-1-(5-hydroxyhexyl)-3-methylxanthine (27 g).

e) A mixture of (R)-7-benzyl-1-(5-hydroxyhexyl)-3-methylxanthine (33.7 g, 84.7 mmol), methanol (60 ml), acetic acid (60 ml), and 10% palladium on carbon (6 g) was treated with hydrogen gas (40 psi) on a Parr shaker. After 14 hours, the mixture was filtered and the filtrate was concentrated under reduced pressure. The residue was purified by flash chromatography on silica gel eluting with 10% methanol/ethyl acetate to provide (R)-1-(5-hydroxyhexyl)-3-methylxanthine (15 g).

f) Chlorosilylated polystyrene (3.51 g) was shaken with a solution of (R)-1-(5-hydroxyhexyl)-3-methylxanthine (6.15 g, 23.1 mmol) and imidazole (2.1 g, 30.8 mmol) in dichloromethane-dimethylformamide (3:1) (40 ml) for 48 hours. Filtration followed by washing of the solid with dimethylformamide, dichloromethane and ethyl acetate (5×10 ml of each) and drying under vacuum provided resin loaded (R)-1-(5-hydroxyhexyl)-3-methylxanthine (4.556 g). The filtrate was concentrated under reduced pressure and the residue was purified by flash chromatography on silica gel eluting with 10% methanol/ethyl acetate to recover unreacted (R)-1-(5-hydroxyhexyl)-3-methylxanthine (3.76 g).

g) Resin loaded (R)-1-(5-hydroxyhexyl)-3-methylxanthine (2 g) was suspended in a solution of 1,2-dichloroethane-dimethylformamide (4:3, 175 ml) so that a homogeneous suspension is formed. The homogeneous suspension was evenly distributed to 80 wells (2.2 ml per well) of a 96-well filter plate. The solvent was removed by filtration, the resin in each well was washed with dichloromethane (1.25 ml per well). A solution of diethyl azodicarboxylate (4.38 g, 25 mmol) in dichloromethane (25 ml) was added slowly to a solution of triphenylphosphine (6.77 g, 25.8 mmol) in tetrahydrofuran (20 ml) at 0–5° C. This solution was equally distributed to the 80 wells. 1 M solutions of 80 different alcohols in tetrahydrofuran (0.27 ml per well, 0.27 mmol) were added (one alcohol per well). The plate was sealed and shaken on an orbital shaker for 72 hours. After filtration, the resin in each well was washed with dichloromethane (5×1 ml). The products were cleaved from the resin by treatment with a solution of trifluoroacetic acid-methanol-dichloroethane (2:1:1, 0.5 ml per well). After shaking for 2 hours, filtration into a 96-well collection plate, washing of the resin with 20% methanol-dichloroethane (2×0.5 ml per well), and concentration of the contents of the collection plate under reduced pressure provided a library of eighty 7-substituted (R)-1-(5-hydroxyhexyl)-3-methylxanthines. The purity of each product was evaluated by thin-layer chromatography (TLC).

Example 30

Synthesis of 7-substituted (S)-1-(5-hydroxyhexyl)-3-methylxanthine Libraries a) Diethyl azodicarboxylate (14.63 g, 84 mmol) was added dropwise to a solution of (R)-7-benzyl-1-(5-hydroxyhexyl)-3-methylxanthine (as prepared in Example 29) (20 g, 56 mmol), 4-nitrobenzoic acid (14 g, 84 mmol) and triphenylphosphine (22 g, 84 mmol) in tetrahydrofuran (200 ml). After stirring for 30 minutes, the reaction mixture was concentrated under reduced pressure. The residue was purified by flash chromatography on silica gel eluting with 30% ethyl acetate-hexane to provide (S)-7-benzyl-1-(5-(4-nitrobenzoyloxy)hexyl)-3-methylxanthine (25 g).

b) (S)-7-benzyl-1(5-(4-nitrobenzoyloxy)hexyl)-3-methylxanthine (25 g, 49.5 mmol) was added to a solution for sodium hydroxide (3.36 g, 84 mmol) in methanol (200 ml). After stirring for 2 hours, the pH was adjusted to 4 by addition of 1 N hydrochloric acid solution. After concentrating under reduced pressure, the residue was partitioned between water (150 ml) and ethyl acetate (300 ml). The organic layer was washed with saturated aqueous sodium chloride solution (150 ml), dried over anhydrous magnesium sulfate and concentrated under reduced pressure. The residue was purified by flash chromatography on silica gel eluting with 20% hexane-ethyl acetate to provide (S)-7-benzyl-1-(5-hydroxyhexyl)-3-methylxanthine (14 g). c) A mixture of (S)-7-benzyl-1-(5-hydroxyhexyl)-3-methylxanthine (14 g, 39 mmol), acetic acid (100 ml), methanol (50 ml), and 10% palladium on carbon (5 g) was treated with hydrogen gels (40 psi) for 14 hours. The mixture was filtered and the filtrate was concentrated under reduced pressure. The residue was purified by flash chromatography on silica gel eluting with 10% methanol-ethyl acetate to give (S)-1-(5-hydroxyhexyl)-3-methylxanthine (6.5 g).

d) 7-Substituted (S)-1-(5-hydroxyhexyl)-3-methylxanthine libraries were synthesized from (S)-1-(5-hydroxyhexyl)-3-methylxanthine according to the method described in Example 29 for the synthesis of 7-substituted (R)-1-(5-hydroxyhexyl)-3-methylxanthine libraries from (R)-1-(5-hydroxyhexyl)-3-methylxanthine.

Example 31

Synthesis of 3-substitut d (R)-1-(5-hydroxyhexyl)-7-methylxanthine Libraries a) Potassium hydroxide (1.0 g, 17.8 mmol) was added to a solution of (R)-1-(5-acetoxyhexyl)-7-methylxanthine (prepared as described for CT12460) (3.8 g, 12.3 mmol) in methanol-water (1:1, 100 ml). After stirring for 3 hours, the pH of the solution was adjusted to 7 by the slow addition of 1 N hydrochloric acid. The solution was concentrated under reduced pressure and the residue was purified by flash chromatography on silica gel eluting with 15% methanol-ethyl acetate to provide (R)-1-(5-hydroxyhexyl)-7-methylxanthine (2.5 g).

b) 3-Substituted (R)-1-(5-hydroxyhexyl)-7-methylxanthine libraries were synthesized from (R)-1-(5-hydroxyhexyl)-7-methylxanthine according to the method described in Example 29 for the synthesis of 7-substituted (R)-1-(5-hydroxyhexyl)-3-methylxanthine libraries from (R)-1-(5-hydroxyhexyl)-3-methylxanthine.

Example 32

Synthesis of 3-substituted (S)-1-(5-hydroxyhexyl)-7-methylxanthine Libraries a) (S)-1-(5-hydroxyhexyl)-7-methylxanthine was synthesized from (R)-1-(5-hydroxyhexyl)-7-methylxanthine according to the method described in Example 30 for the synthesis of (S)-7-benzyl-1-(5-hydroxyhexyl)-3-methylxanthine from (R)-7-benzyl-1-(5-hydroxyhexyl)-3-methylxanthine.

b) 3-Substituted (S)-1-(5-hydroxyhexyl)-7-methylxanthine libraries were synthesized from (S)-1-(5-hydroxyhexyl)-7-methylxanthine according to the method described in Example 30 for the synthesis of 7-substituted (S)-1-(5-hydroxyhexyl)-3-methylxanthine libraries from (S)-1-(5-hydroxyhexyl)-3-methylxanthine.

Example 33

Synthesis of (R)-1-(5-hydroxhexyl)-7-ethoxymethyl-8-amino-3-methylxanthine Libraries a) To a solution of (R)-1-(5-acetoxyhexyl)-8-bromo-7-ethoxymethyl-3-methylxanthine (prepared as described for CT12440) (3.8 g, 8.5 mmol ) in methanol (150 ml) was added a solution of hydrogen chloride in ether (1.0 M, 20 ml). The reaction mixture was stirred at room temperature for 24 hours. Evaporation of the solvent under reduced pressure provided (R)-1-(5-hydroxyhexyl)-8-bromo-3-methylxanthine (2.9 g, 98% yield) as a white solid.

b) To a stirring suspension of (R)-1-(5-hydroxyhexyl)-8-bromo-3-methylxanthine (2.9 g, 8.4 mmol) and potassium carbonate (1.50 g, 10.5 mmol) in dimethylformamide (70 ml) was added chloromethyl ethyl ether (0.83 g), 8.8 mmol). After stirring overnight at room temperature, the mixture was poured into ice cold water (200 ml) and was stirred at 0–5° C. for 1 hour. The precipitate was filtered, rinsed with water (5×25 ml) and dried under vacuum to provide (R)-1-(5-hydroxyhexyl)-8-bromo-7-ethoxymethyl-3-methylxanthine (2.5 g, 74% yield) as a white solid.

c) To a stirring solution of (R)-1-(5-hydroxyhexyl)-8-bromo-7-ethoxymetyl-3-methylxanthine (2.5 g, 6.2 mmol), 4-dimethylaminopyridine (0.38 g, 3.3 mmol) and triethylamine (1.25 g, 12.4 mmol) in chloroform (40 ml) was added succinic anhydride (0.93 g, 9.3 mmol). After stirring overnight at room temperature, the mixture was quenched with ice cold water (100 ml) and stirred at 0–5° C. for 1 hour. Potassium hydrogensulfate solution (0.5 N) was added until pH=2–3. The organic phase was separated and washed with saturated aqueous sodium chloride solution (2×35 ml), dried over magnesium sulfate and concentrated under reduced pressure to provide (R)-1-(5-hydroxyhexyl)-8-bromo-7-ethoxymethyl-3-methylxanthine monosuccinate ester (3.0 g, 96% yield) as an oil.

d) To a suspension of (R)-1-(5-hydroxyhexyl)-8-bromo-7-ethoxymethyl-3-methylxanthine monosuccinate ester (3.0 g, 6.0 mmol), 4-dimethylaminopyridine (0.24 g, 2.1 mmol) and Argo-Gel-NH$_2$ resin (5.0 g, 2.1 mmol) in chloroform (70 ml) was added 1,3-diisopropylcarbodiimide (0.76 g, 6.0 mmol). The reaction mixture was shaken at room temperature for 24 hours. After filtration, the resin was rinsed with chloroform (3×50 ml), chloroform-dimethylformamide (1:1, 3×50 ml), dimethylformamide (2×50 ml), chloroform-dimethylformamide (1:1, 3×50 ml) and chloroform (4×50 ml). After drying under reduced pressure, resin bound (R)-1-(5-hydroxyhexyl)-8bromo-7-ethoxymethyl-3-methylxanthine (succinate-linked) (6.0 g) was obtained.

e) Resin bound (R)-1-(5-hydroxyhexyl)-8-bromo-7-ethoxymethyl-3-methylxanthine (succinate-linked) obtained above was evenly distributed to 80 wells of a 96-well teflon filter block (Charybdis). 80 different amines in dimethylsulfoxide (10 equiv., 1.0 M) were added to the wells (1 per well). The block was sealed and shaken in an incubator-shaker at 60° C. for 48 hours. After filtration, the resin in each well was rinsed with dimethylsulfoxide (3×0.25 ml), chloroform-dimethylformamide (1:1, 3×0.25 ml), dimethylformamide (3×0.25 ml) and chloroform (3×0.25 ml). Products were cleaved from the resin by addition of ammonia in methanol (2.0 M, 0.65 ml per well). After shaking at room temperature for 48 hours, the resin in each well was filtered and the filtrates individually collected in 80 wells of a 96-well collection plate. Evaporation under reduced pressure provided an (R)-1-(5-hydroxyhexyl)-7-ethoxymethyl-8-amino-3-methylxanthine library.

Example 34

Synthesis of (R)-1-(5-hydroxyhexyl)-8-amino-3-methylxanthine Libraries (R)-1-(5-Hydroxyhexyl)-7-ethoxymethyl-8-amino-3-methylxanthine libraries synthesized as described in Example 33 were treated with a solution composed of concentrated hydrochloric acid and ethanol (1:4, 0.8 ml per well) and the block was heated in an oven at 80° C. for 12 hours. Remaining reagents and byproducts were evaporated under reduced pressure providing (R)-1-(5-hydroxyhexyl)-8-amino-3-methylxanthine libraries.

Example 35

Synthesis of (R)-1-(5-hydroxyhexyl)-8-aminomethyl-3,7-dimethylxanthine Libraries a) To a stirred suspension of (R)-3-(5-acetoxyhexyl)-6-amino-1-methyl-5-nitroso-uracil (prepared as described for CT12452) (23.35 g, 74.8 mmol) in water (230 ml) at 60° C. was added sodium hydrosulfide (61.7 g) in portions. After heating at 60° C. for additional 1 hour, the reaction mixture was cooled to 0–5° C. Chloroform (240 ml) was added followed by potassium carbonate (51.8 g), 37.5 mmol) in portions. The reaction mixture was stirred at 0–5° C. for additional 0.5 hour whereupon benzyloxyacetyl chloride (20.7 g, 112 mmol) was added dropwise. After stirring at 0–5° C. for an additional 1 hour, the mixture was extracted with 10% methanol-chloroform solution (1100 ml). The aqueous phase was further extracted with 10% methanol-chloroform solution (3×250 ml). The combined organic extracts were evaporated under reduced pressure to provide a beige solid which was dissolved in 10% aqueous sodium hydroxide solution (500 ml) and heated at reflux for 0.5 hour. After cooling to 0–5° C., the pH was adjusted to 2–3 by addition of concentrated hydrochloric acid and the mixture was extracted with ethyl acetate (5×250 ml). The combined extracts were washed with saturated aqueous sodium chloride solution (100 ml), dried over magnesium sulfate, and concentrated under reduced pressure to provide a crude product. Recrystallization (ethyl acetate-hexane) provided (R)-8-benzyloxymethyl-1-(5-hydroxyhexyl)-3-methylxanthine (22.0 g, 77% yield) as a white solid.

b) To a stirred solution of (R)-8-benzyloxymethyl-1-(5-hydroxyhexyl)-3-methylxanthine (19.9 g, 51.5 mmol), triethylamine (10.4 g, 103 mmol) and 4-dimethylaminopyridine (1.33 g, 11 mmol) in chloroform (130 ml) was added acetic anhydride (6.57 g, 64.4 mmol). After stirring for 3 hours at room temperature, the reaction mixture was quenched by addition of methanol (5 ml). The mixture was washed with aqueous potassium hydrogen sulfate solution (0.1 N) to pH 6–7, with water (2×50 ml) and with saturated aqueous sodium chloride solution (50 ml). After drying over magnesium sulfate, the organic solution was evaporated under reduced pressure to provide (R)-1-(5-acetoxyhexyl)-8-benzoxymethyl-3-methylxanthine (19.6 g, 88% yield) as white colored solid.

c) To a solution of (R)-1-(5-acetoxyhexyl)-8-benzoxymethyl-3-methylxanthine (4.0 g, 9.33 mmol) in acetic acid (40 ml) was added 10% palladium on carbon (0.52 g). The mixture was treated with hydrogen gas (50 psi) on a Parr shaker for 18 hours. After removing catalyst by filtration, evaporation of the solvent under reduced pressure provided (R)-1-(5-acetoxyhexyl)-8-hydroxymethyl-3-methylxanthine (2.8 g, 88% yield) as a white solid.

d) To a stirred suspension of (R)-1-(5-acetoxyhexyl)-8-hydroxymethyl-3-methylxanthine (6.35 g, 18.8 mmol) and potassium carbonate (5.2 g, 38 mmol) in dimethylformamide (55 ml) was added methyl iodide (4.0 g, 28.2 mmol). After stirring overnight at room temperature, the mixture was poured into ice cold water (250 ml) and stirred at 0–5° C. for 1 hour. The precipitate was filtered, rinsed with water (5×25 ml), and dried under vacuum to provide (R)-1-(5-acetoxyhexyl)-8-hydroxymethyl-3,7-dimethylxanthine (6.3 g, 95% yield) as a white solid.

e) To thionyl chloride (30 ml) stirred at 0–5° C. was added (R)-1-(5-acetoxyhexyl)-8-hydroxymethyl-3,7-dimethylxanthine (6.3 g, 17.9 mmol). After stirring overnight at room temperature, unreacted thionyl chloride and volatile byproducts were evaporated under reduced pressure. To the residual oil was added methanol (300 ml) followed by hydrogen chloride in ether (1.0 M, 20 ml). After stirring for 12 hours, volatile materials were evaporated under reduced pressure to provide (R)-1-(5-hydroxyhexyl)-8-chloromethyl-3,7-dimethylxanthine (5.6 g, 96% yield) as a white solid.

f) To a suspension of (R)-1-(5-hydroxyhexyl)-8-chloromethyl-3,7-dimethylxanthine (5.6 g, 17.0 mmol) and 3,4-dihydro-2H-pyran-2-ylmethoxymethyl polystyrene (DHP HM resin, Novabiochem) (3.6 g, 3.4 mmol) in dichloroethane (55 ml) and dimethylsulfoxide (20 ml) was added p-toluenesulfonic acid (0.90 g, 3.4 mmol). After shaking at 4° C. for 16 hours, the resin was filtered and rinsed with dimethylsulfoxide (3×50 ml), dichloromethane-dimethylsulfoxide (1:1) (3×50 ml), and dichloromethane (4×50 ml). Drying under reduced pressure provided resin bound (R)-1-(5-hydroxyhexyl)-8-chloromethyl-3,7-dimethylxanthine (4.65 g).g) Resin bound (R)-1-(5-hydroxyhexyl)-8-chloromethyl-3,7-dimethylxanthine (4.65 g) was distributed evenly to 80 wells of a 96-well teflon filter block (Charybdis). Solutions of 80 different amines in tetrahydrofuran (10 equiv., 1.0 M) were added to the wells (1 per well). The block was sealed and shaken in an incubation-shaker at 50° C. for 18 hours. After filtration, the resin in each well was rinsed with dimethylsulfoxide (5×0.6 ml), dichloromethane-dimethylsulfoxide (1:1, 10×0.6 ml), and dichloromethane (5×0.6 ml). Products were cleaved from the resin by addition of a solution composed of hydrogen chloride (4.0 M in dioxide), ethanol, and dichloroethane and (2:1:1, 0.8 ml per well). The block was shaken at room temperature for 18 hours. After filtration, the resin in each well was filtered and the filtrates individually collected in 80 wells of a 96-well collection plate. Evaporation under reduced pressure provided an (R)-1-(5-hydroxyhexyl)-8-aminomethyl-3,7-dimethylxanthine library.

Example 36

Effect on IL-12 Signalling

This example illustrates the inventive compounds' ability to suppress Th1 differentiation in vitro by blocking IL-12 signalling. Each of compounds A through Y were tested in an IL-12 dependent in vitro T-helper cell differentiation assay as described in LeGross et al., *J. Exp. Med.*, 172:921–929 (1990). Recombinant IL-12 was used to induce Th1 differentiation. Spenic T cells were purified utilizing the antibodies RA3-3A1/6.1 (anti-B220), J11d and MAR18.5 (anti-rat kappa chain) to deplete the B cells via complement mediated toxicity following the procedure set forth in Klaus et al., *J. Immunol.*, 149:1867–1875 (1992). Splenic T cells were stimulated at $5 \times 10^5$/ml with insoluble anti-CD3 alone (145-2C11, Pharmingen, San Diego, Calif.), or anti-CD3 and 5 U/ml IL-12, with and without each inventive compound. After seven days, equal numbers of viable cells were restimulated for 24 hours with anti-CD3 without the inventive compounds, and the supernatants were collected and assayed for IFN-γ production. IFN-γ and IL-4 levels were measured by Interest kits from Genzyme specific for IFN-γ and IL-4. The results are shown in Table 2 below.

Th1 differentiation was induced by culturing anti-CD3 stimulated T cells in the presence of exogenous IL-12. Under these conditions, Th1 differentiation was consistently enhanced as compared to T cells stimulated with anti-CD3 alone. It was observed that the presence of the tested compounds during T cell activation inhibited Th1 differentiation, which had been enhanced by the addition of exogenous IL-12. The values in the "$IC_{50}$ μM" column were determined by measuring the inhibition of IL-121 induced Th1 differentiation as defined by IFN-γ production upon secondary stimulation with anti-CD3 alone. None of the compounds affected the viability or recovery of T cells after one week of culture.

TABLE 2

| EX. | CMPD NO. | STRUCTURE | [$IC_{50}$; μM] |
| --- | --- | --- | --- |
| A | CT7549 | 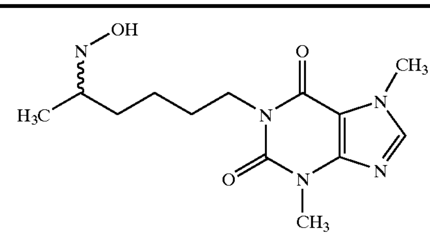 | 21 |
| B | CT11495 | 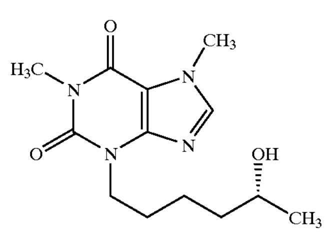 | 35 |
| C | CT11499 | 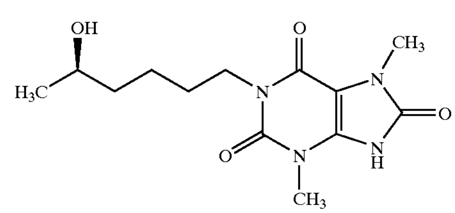 | 30 |

TABLE 2-continued

| EX. | CMPD NO. | STRUCTURE | [IC$_{50}$; µM] |
|---|---|---|---|
| D | CT12404 | (structure) | 28 |
| E | CT12407 | (structure) | 30 |
| F | CT12422 | (structure) | 19 |
| G | CT12440 | (structure) | 9 |
| H | CT12441 | (structure) | 19 |
| I | CT12447 | (structure) | 25 |

TABLE 2-continued

| EX. | CMPD NO. | STRUCTURE | [IC$_{50}$; μM] |
| --- | --- | --- | --- |
| J | CT12452 | (structure) | 35 |
| K | CT12458 | (structure) | 27 |
| L | CT12459 | (structure) | 17 |
| M | CT12461 | (structure) | 17 |
| N | CT12463 | (structure) | 31 |
| O | CT12464 | (structure) | 12 |
| P | CT12465 | (structure) | 15 |

TABLE 2-continued
| EX. | CMPD NO. | STRUCTURE | [IC$_{50}$; µM] |
|---|---|---|---|
| Q | CT12481 | 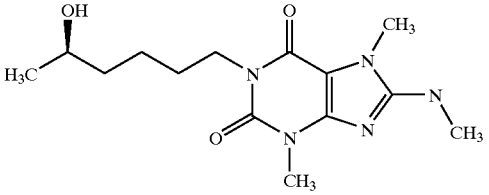 | 24.7 |
| R | CT12485 | 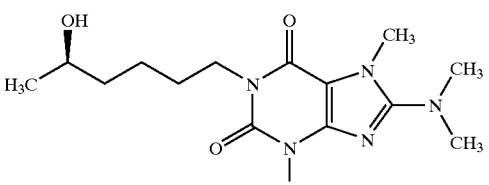 | 10 |
| S | CT12490 | 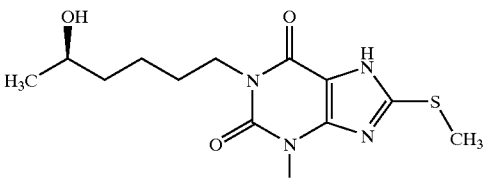 | 20 |
| T | CT17556 | 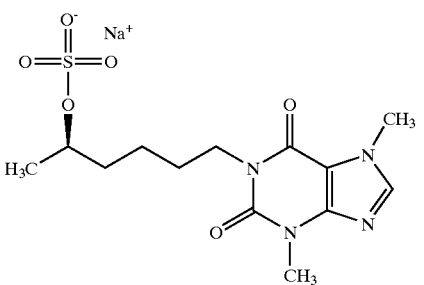 | 23.8 |
| U | CT17557 | 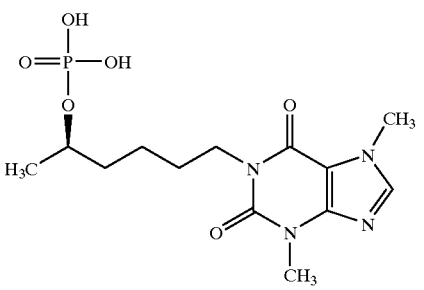 | 9 |
| V | CT22404 | 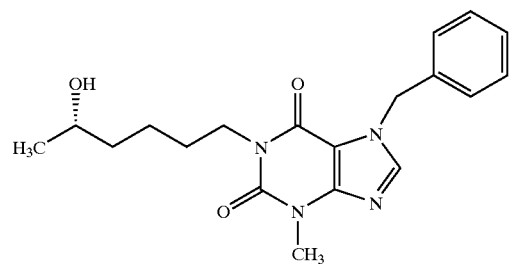 | 10 |

TABLE 2-continued

| EX. | CMPD NO. | STRUCTURE | [IC$_{50}$; μM] |
|---|---|---|---|
| W | CT22464 | 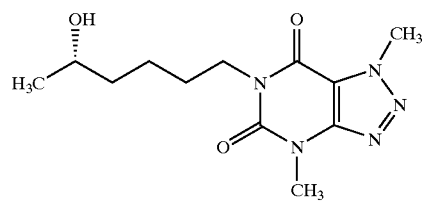 | 30 |
| X | CT22465 | 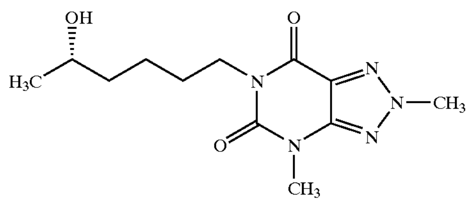 | 14 |
| Y | CT14577 | 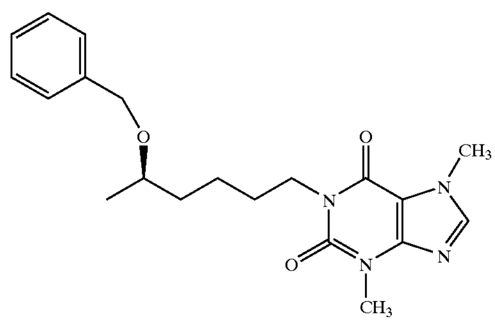 | 47 |
| Z | CT12460 | 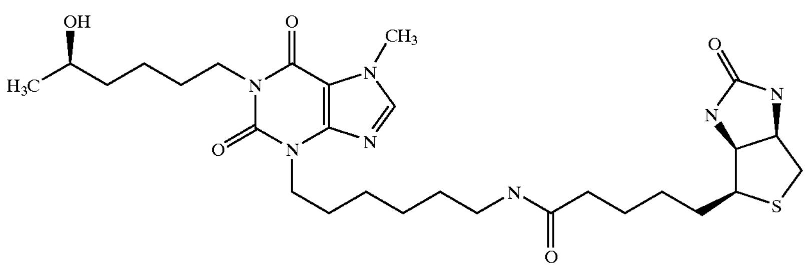 | 21.8 |

Example 37

Effect on IFN-γ Production Induced by IL-12

The ability of IL-12 to induce generation of Th1 cells is aided by IFN-γ, a cytokine which is known to be induced by IL-12 itself. (R)-3-(N-biotinyl-6-aminohexyl)-1-(5-hydroxyhexyl)-7-methylxanthine (CT12460) and (R)-3-(N-biotinyl-2-aminoethyl)-1-(5-hydroxyhexyl)-7-methylxanthine (CT13410) were tested in an interferon gamma (IFN-γ) induction assay as described in Kobayashi, M., et al., "Identification and Purification of Natural Killer Cell Stimulatory Factor (NKSF), A Cytokine with Multiple Biologic Effects on Human Lymphocytes," *J. Exp. Med.U.*, 170:827–845 (at 829, 830 and 836) (1989). See also, Wolf, S., et al., "Interluekin 12: A Key Modulator of Immune Function," *Stem Cells*, 12:154–168 (1994) and Trinchieri, supra. FIG. 1 shows that when CT12460 and CT13410 were added to a culture of a splenocytes, IL-12 induced IFN-γ secretion was inhibited. Thus, the data shows that CT12460 and CT13410 and both effective inhibitors of IL-12 signaling in vitro.

Example 38

Metabolic Stability

Compounds of the present invention were shown to be metabolically stable as determined in the microsomal metabolism assay generally described below. Compounds of the present invention and (R)-1-(5-Hydroxyhexyl)-3,7-dimethylxanthine ("lisofylline" or "LSF") (used as a control) were incubated with human or monkey microsomes and the loss of each was measured and compared.

The incubation solution consisted of 50 uM test compound, human or cynomolgus monkey microsomes and 2 mM nicotine adenine dinucleotide phosphate disodium salt (NADPH) in 100 mM phosphate buffer, pH 7.4. Microsome concentration was adjusted to give approximately 45% loss of LSF after 60 minutes incubation; average concentrations were 5 mg/ml protein or 1 mg/ml protein for human or monkey, respectively. Reaction components were placed in loosely capped glass tubes. incubations were carried out for 0 and 60 min in an orbital water bath shaker at 37° C. and were stopped by the addition of 1.2 volume methanol. For compounds that retain a chiral secondary alcohol, the incubations were stopped by mixing with 6 mL dichloromethane. Incubations were done in duplicate or triplicate. LSF was incubated in each assay batch as a reference compound.

In preparation for achiral chromatography, samples were supplemented with 1-(7-hydroxyheptyl)-3,7-dimethylxanthine (CT1545) (as a standard) to a final concentration of 20 ug/mL and centrifuged at 200 g for 10 min. The resultant supernatants were diluted 10 fold with 25 mM potassium phosphate, pH 3.0. Fifty ul of each sample was chromatographed on a C16 RP Amide column (Supelco), 4.6 mm×250 mm, 5 micron, at a column temperature of 35° C. The mobile phase was mixture of 25 mM potassium phosphate (A) and acetonitrile (B) delivered at 1.0 mL/min as a gradient, typically 10%B to 75%B over 15 min. Chromatograms were monitored at 273 nm or other lambda max.

Incubations stopped with dichloromethane were supplemented with 2.5 µg CT1545 and frozen. On thawing the organic phase was removed and dried under a N2 stream, then taken up in 250 µL hexane/isopropanol (90/10). Chromatography was carried out on a Daicel Chiralpak AD column, 4.6 mm×250 mm, 10 micron, held at 35° C. with a 25 µL injection volume and isocratic elution with hexane (+0.2% trichloroacetic acid)/isopropanol at 1.0 ml/min. Mobile phase proportions were adjusted to achieve baseline or near baseline resolution of enantiomers.

Analyte response observed as the ratio of the area of the test compound peak or of the LSF peak to the area of the internal standard. The % metabolism was calculated as: (ratio@60 min−ratio@0 min)ratio@60 min×100%. Metabolic stability was expressed as: metabolic index (MI)=% metabolism$_{test\ compound}$/% metabolism$_{LSF}$.

In this Example, NADPH, monobasic potassium phosphate, dibasic sodium phosphate and trichloroacetic acid were obtained from Sigma. Organic solvents were obtained from Burdick and Jackson. Water was distilled and deionized. Microsomes (In Vitro Technologies) were obtained as frozen suspensions at −70° C. and stored at that temperature until use. Human microsomes represented a pool of 15 individuals representing ca. 50/50 gender ratio and monkey microsomes were from a pool of two or more metals. HPLC columns were from Supelco or Daicel. HPLC chromatography was carried out on Shimadzu series 10 instruments.

Example 39

Adoptive Transfer EAE

Figure 2:
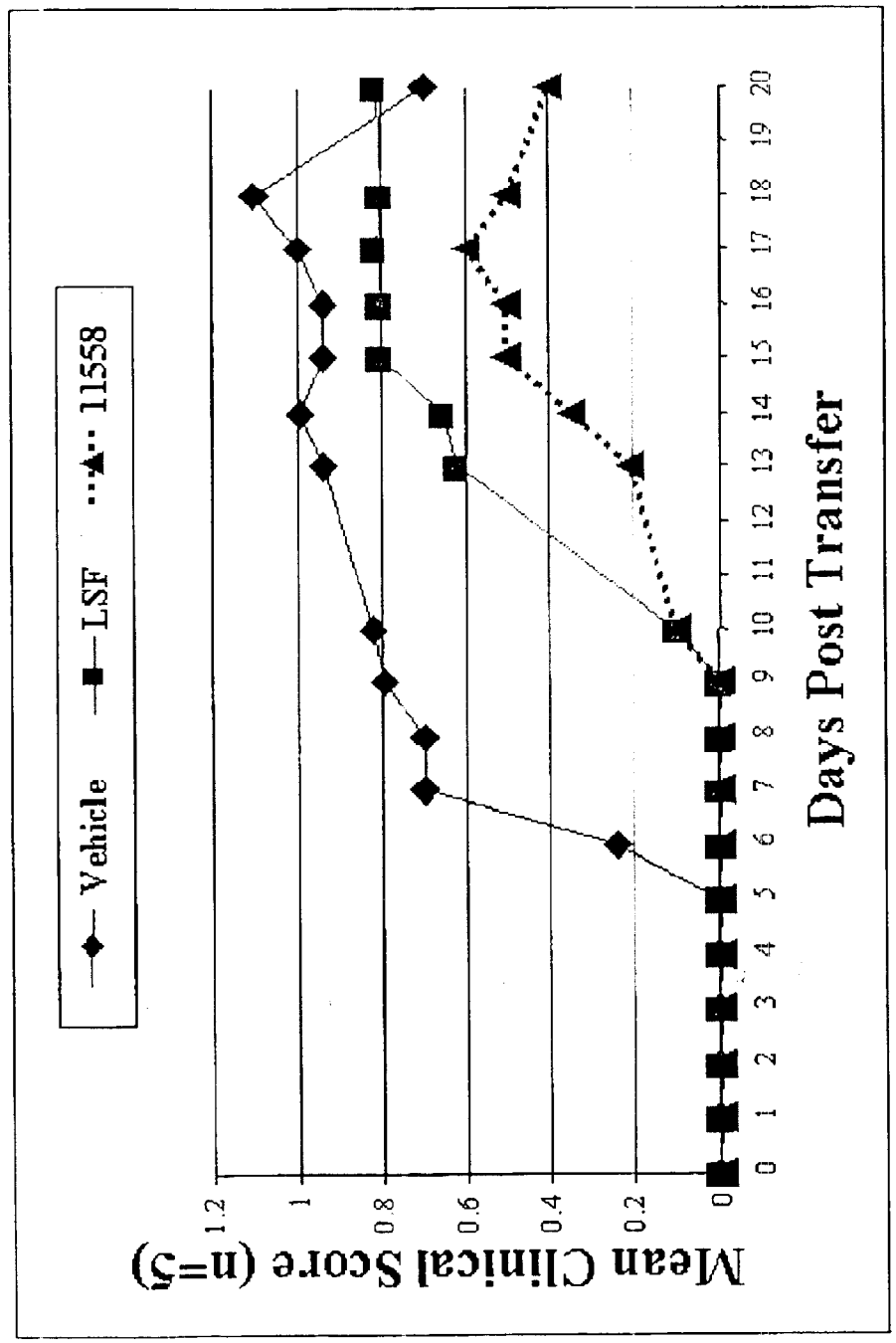
FIG. 2 shows the inhibitory effect of (R)-1-(5-N,N-dimethylaminohexyl)-3,7-dimethylxanthine (CT 11558) in an adoptive transfer experimental allergic encephalomyelitis (EAE) model.

An adoptive transfer experimental allergic encephalomyelitis (EAE) model was used, in which the splenic T cells from actively immunized mice were cultured for 4 days in antigen-containing (myelin basic protein) medium. The cells were then transferred to naive recipients, which were then evaluated for clinical changes in motor nerve function in the presence or absence of treatment with LSF or the compound of Example 22 (CT11558). Both compounds were administered on a bid schedule, by gavage, for the first 5 days. FIG. 2 shows that both compounds produced a significant delay in the onset and a decrease in the magnitude of observable clinical deficits as compared with animals receiving activated T cells and gavage with vehicle only.

Example 40

Graft-Versus-Host Disease (GVHD) Model

Figure 3:
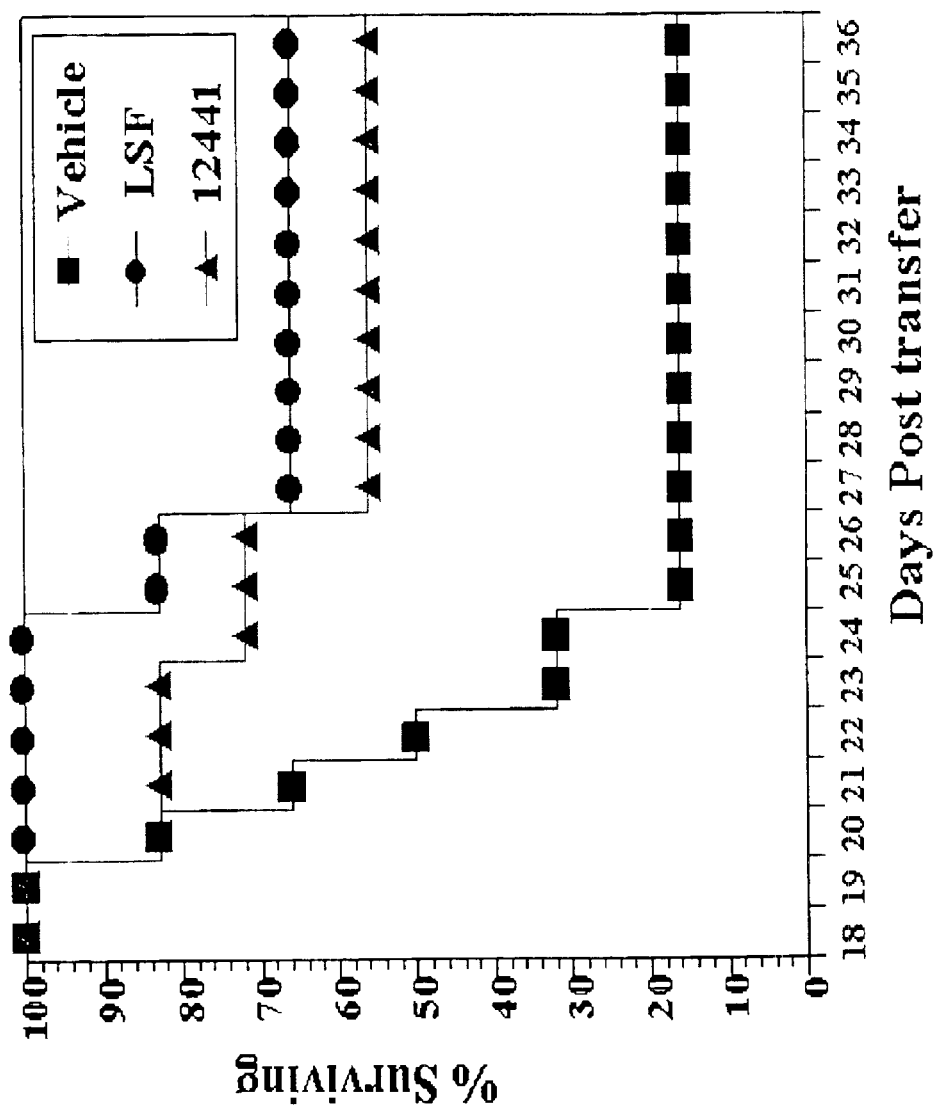
FIG. 3 shows the inhibitory effect of (R)-1-(5-hydroxyhexyl)-3-methyl-8-(N-methyl)aminomethylxanthine (CT 12441) against GVHD.

In a GVHD model, an irradiated F1 hybrid recipient population, bred across a parental major H2 mismatch, was infused with maternal cells activated in vitro with conconavalian A (Con A) and IL-12. LSF and the compound of Example 7 (CT12441) were compared with a vehicle control for efficacy. Both compounds were administered on a bid schedule, by gavage, for the first 5 days. FIG. 3 shows that both compounds produced a significant increase of survival, as compared with animals receiving the activated maternal T cells and gavage with the vehicle control only, as assessed over 36 days after adoptive transfer of cells.

Those skilled in the art will recognize, or be able to ascertain using no more than routine experimentation, many equivalents to the specific embodiments of the invention specifically described herein. Such equivalents are intended to be encompassed in the scope of the following claims.

What is claimed is:

1. A therapeutic compound, including resolved enantiomers, diastereomers, tautomers, salts and solvates thereof, having the following formula (I):

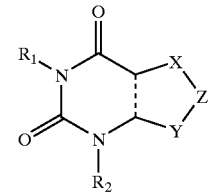

wherein:

X is N(R$_3$), Y is NH or N(CH$_3$) and Z is C(R$_4$), where R$_3$ is H, CH$_3$ or CH$_2$OCH$_2$CH$_3$, and R$_4$ is selected from the group consisting of C$_{(1-20)}$alkylamino, C$_{(1-20)}$ alkylaminoalkyl, C$_{(1-20)}$aminoalkyl, C$_{(1-20)}$ aminoalkoxyalkenyl, C$_{(1-20)}$aminoalkoxyalkenyl, C$_{(1-20)}$diaminoalkyl, C$_{(1-20)}$triaminoalkyl, C$_{(1-20)}$ tetraaminoalkyl, C$_{(5-15)}$aminotrialkoxyamino, C$_{(1-20)}$ alkylamido, C$_{(1-20)}$alkylamidoalkyl, C$_{(1-20)}$amidoalkyl, C$_{(1-20)}$acetamidoalkyl;

R$_1$ is —(CH$_2$)$_n$—CHOH—CH$_3$ which may be substituted with a member of the group consisting of acylamino and —NR$^a$R$^b$, wherein each of R$^a$ and R$^b$ may be the same or different and each is selected from the group consisting of hydrogen, optionally substituted alkyl, cycloalkyl, alkenyl, cycloalkenyl, alkynyl, aryl, heteroaryl and heterocyclic group; and n is 3–7; and R$_2$ is hydrogen or methyl and the dot line represent a single bond or double bond.

2. The therapeutic compound of claim 1 wherein R$_1$ is —(CH$_2$)$_n$—COOH—CH$_3$, X is N(CH$_3$), Y is NH, and R$_4$ is C$_{(1-20)}$alkylaminoalkyl.

3. The therapeutic compound of claim 1 wherein R$_1$ is —(CH$_2$)$_n$—CHOH—CH$_3$ which the hydroxy group is substituted with —NR$^a$R$^b$, wherein each of R$^a$ and R$^b$ may be the same or different and each is selected from the group consisting of hydrogen, optionally substituted alkyl, cycloalkyl, alkenyl, cycloalkenyl, alkynyl, aryl, heteroaryl and heterocyclic group, X is N(CH$_3$), and Y is NH.

4. A compound having the formula
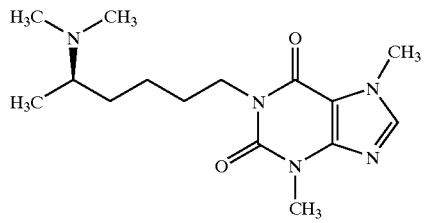
or a pharmaceutically acceptable salt thereof.
5. A compound having the formula
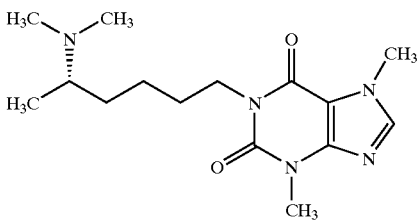
or a pharmaceutically acceptable salt thereof.
6. A pharmaceutical composition comprising the compound as defined in any of claims 4, 5 or 1–3, in admixture with a pharmaceutically acceptable carrier, adjuvant or vehicle.
* * * * *